(12) United States Patent
Rapoport

(10) Patent No.: US 10,524,690 B2
(45) Date of Patent: Jan. 7, 2020

(54) INSTALLABLE RF COIL ASSEMBLY

(71) Applicant: Aspect Imaging Ltd., Shoham (IL)

(72) Inventor: Uri Rapoport, Moshav Ben Shemen (IL)

(73) Assignee: ASPECT IMAGING LTD., Shoham (IL)

( * ) Notice: Subject to any disclaimer, the term of this patent is extended or adjusted under 35 U.S.C. 154(b) by 0 days.

(21) Appl. No.: 14/892,209

(22) PCT Filed: May 21, 2014

(86) PCT No.: PCT/IL2014/050451
§ 371 (c)(1),
(2) Date: Nov. 19, 2015

(87) PCT Pub. No.: WO2014/188425
PCT Pub. Date: Nov. 27, 2014

(65) Prior Publication Data
US 2016/0089055 A1 Mar. 31, 2016

Related U.S. Application Data

(60) Provisional application No. 61/994,903, filed on May 18, 2014.

(30) Foreign Application Priority Data

May 21, 2013 (IL) .......................................... 226488

(51) Int. Cl.
*A61B 5/055* (2006.01)
*G01R 33/30* (2006.01)
(Continued)

(52) U.S. Cl.
CPC .............. *A61B 5/0555* (2013.01); *A61F 7/00* (2013.01); *A61G 11/00* (2013.01); *A61G 11/002* (2013.01);
(Continued)

(58) Field of Classification Search
CPC .... A61B 2017/00911; A61B 2503/045; A61B 5/0555; A61F 7/00; A61G 11/00;
(Continued)

(56) References Cited

U.S. PATENT DOCUMENTS 1,900,342 A 3/1933 Hess
2,638,087 A 5/1953 Livsey
(Continued)

FOREIGN PATENT DOCUMENTS

CA 2815746 5/2012
CN 2448344 9/2001
(Continued)

OTHER PUBLICATIONS

International Search Report of PCT/IL2014/050451, dated May 21, 2014.
(Continued)

*Primary Examiner* — Ruth S Smith
(74) *Attorney, Agent, or Firm* — Loeb & Loeb LLP

(57) ABSTRACT

A maneuverable RF coil assembly, useful for being maneuvered at both positions: (i) over at least a portion of a neonate immobilized within a cradle at time of MR imaging; and (ii) below or aside the cradle when it is not required for imaging. The maneuverable RF coil assembly comprises at least one RF coil and maneuvering mechanism. The maneuvering mechanism comprises both: (i) a linear reciprocating mechanism for approaching or otherwise drawing away at least one coil to and from the neonate; and (ii) tilting mechanism for placing at least one coil away from the neonate.

13 Claims, 12 Drawing Sheets

(51) Int. Cl.

| | |
|---|---|
| *A61G 11/00* | (2006.01) |
| *A61F 7/00* | (2006.01) |
| *G01R 33/38* | (2006.01) |
| *G01R 33/28* | (2006.01) |
| *G01R 33/34* | (2006.01) |
| *A61G 13/02* | (2006.01) |
| *A61G 13/10* | (2006.01) |
| *A61B 17/00* | (2006.01) |

(52) U.S. Cl.
CPC ........... *G01R 33/288* (2013.01); *G01R 33/30* (2013.01); *G01R 33/34* (2013.01); *G01R 33/3806* (2013.01); *A61B 2017/00911* (2013.01); *A61B 2503/045* (2013.01); *A61G 11/005* (2013.01); *A61G 13/02* (2013.01); *A61G 13/104* (2013.01); *A61M 2202/0208* (2013.01)

(58) Field of Classification Search
CPC .... A61G 11/002; A61G 11/005; A61G 13/02; A61G 13/104; A61M 2202/0208; G01R 33/288; G01R 33/30; G01R 33/34; G01R 33/3806
See application file for complete search history.

(56) References Cited

U.S. PATENT DOCUMENTS

| | | | |
|---|---|---|---|
| 2,708,927 A | 5/1955 | Dixon et al. | |
| 3,012,836 A | 12/1961 | Smith et al. | |
| 3,315,671 A | 4/1967 | Creelman | |
| 3,470,866 A | 10/1969 | Gittelson | |
| 3,655,178 A | 4/1972 | Vezina | |
| 3,710,791 A | 1/1973 | Deaton | |
| 3,920,000 A | 11/1975 | Atherton et al. | |
| 4,161,172 A | 7/1979 | Pickering | |
| 4,509,505 A | 4/1985 | Mercey et al. | |
| 4,567,894 A | 2/1986 | Bergman | |
| 4,712,263 A | 12/1987 | Pronzinski | |
| 4,750,474 A | 6/1988 | Dukhan et al. | |
| 4,936,824 A | 6/1990 | Koch et al. | |
| 5,028,872 A | 7/1991 | Nakabayashi | |
| 5,059,906 A * | 10/1991 | Yamanaka | G01R 33/341 324/318 |
| 5,100,375 A | 3/1992 | Koch | |
| 5,402,543 A | 4/1995 | Dietrich et al. | |
| 5,446,934 A | 9/1995 | Frazier | |
| 5,509,159 A | 4/1996 | Du-Bois | |
| 5,534,669 A | 7/1996 | Schroeder et al. | |
| 5,759,149 A | 6/1998 | Goldberg et al. | |
| 5,797,833 A | 8/1998 | Kobayashi et al. | |
| 5,800,335 A | 9/1998 | Koch et al. | |
| 5,817,003 A | 10/1998 | Moll et al. | |
| 5,917,324 A * | 6/1999 | Leussler | G01R 33/365 324/318 |
| 5,943,716 A | 8/1999 | Chu | |
| 5,971,913 A | 10/1999 | Newkirk et al. | |
| 6,036,634 A | 3/2000 | Goldberg et al. | |
| 6,155,970 A | 12/2000 | Dykes et al. | |
| 6,231,499 B1 | 5/2001 | Jones | |
| D446,675 S | 8/2001 | Straub | |
| 6,317,618 B1 | 11/2001 | Livni et al. | |
| 6,409,654 B1 | 6/2002 | McClain et al. | |
| 6,433,548 B1 * | 8/2002 | Furuta | G01R 33/34053 324/318 |
| 6,471,634 B1 | 10/2002 | Dykes et al. | |
| 6,511,414 B1 | 1/2003 | Hamsund | |
| 6,611,702 B2 | 8/2003 | Rohling et al. | |
| 6,641,521 B2 | 11/2003 | Kolarovic | |
| 6,666,816 B2 | 12/2003 | Mountain | |
| RE38,453 E | 3/2004 | Lessard et al. | |
| 6,776,527 B1 | 8/2004 | Tybinkowski et al. | |
| 6,860,272 B2 | 3/2005 | Carter et al. | |
| 6,992,486 B2 | 1/2006 | Srinivasan | |
| 7,255,671 B2 | 8/2007 | Boone et al. | |
| 7,278,962 B2 | 10/2007 | Lonneker-Lammers | |
| D567,948 S | 4/2008 | Tierney et al. | |
| 7,482,558 B2 | 1/2009 | Koch | |
| 7,599,728 B2 | 10/2009 | Feenan | |
| 7,719,279 B2 | 5/2010 | Rapoport | |
| 7,784,121 B2 | 8/2010 | Ahlman | |
| 8,147,396 B2 | 4/2012 | Srinivasan | |
| 8,194,866 B2 | 6/2012 | Smith | |
| 8,217,653 B2 | 7/2012 | Vaughan | |
| 8,390,288 B2 | 3/2013 | Grasesslin et al. | |
| 9,974,705 B2 | 5/2018 | Rapoport | |
| 2001/0049465 A1 | 12/2001 | Goldberg et al. | |
| 2002/0072648 A1 | 6/2002 | Dykes et al. | |
| 2002/0123681 A1 * | 9/2002 | Zuk | A61B 5/055 600/410 |
| 2002/0143233 A1 | 10/2002 | Donnelly et al. | |
| 2002/0173696 A1 | 11/2002 | Kolarovic et al. | |
| 2002/0173717 A1 | 11/2002 | Rohling et al. | |
| 2003/0088175 A1 | 5/2003 | Branch et al. | |
| 2004/0030241 A1 | 2/2004 | Green et al. | |
| 2004/0034273 A1 | 2/2004 | Boris | |
| 2004/0133064 A1 | 7/2004 | Castillon Levano et al. | |
| 2004/0186341 A1 | 9/2004 | McDermott | |
| 2004/0236174 A1 | 11/2004 | Boone et al. | |
| 2004/0236175 A1 | 11/2004 | Boone et al. | |
| 2005/0004422 A1 | 1/2005 | Caspary et al. | |
| 2005/0020906 A1 | 1/2005 | Seijger et al. | |
| 2005/0038314 A1 | 2/2005 | Falk | |
| 2005/0113668 A1 * | 5/2005 | Srinivasan | A61B 5/416 600/411 |
| 2006/0079730 A1 | 4/2006 | Getsla | |
| 2007/0232894 A1 | 10/2007 | Feenan | |
| 2008/0163425 A1 | 7/2008 | White | |
| 2009/0044335 A1 | 2/2009 | Brewin et al. | |
| 2009/0209846 A1 | 8/2009 | Bammer | |
| 2009/0237077 A1 | 9/2009 | Vaughan | |
| 2010/0004502 A1 | 1/2010 | Honma et al. | |
| 2010/0010599 A1 | 1/2010 | Chen et al. | |
| 2010/0168502 A1 | 7/2010 | Delaporte et al. | |
| 2010/0172468 A1 | 7/2010 | Gregerson | |
| 2010/0315085 A1 * | 12/2010 | Brown | A61B 5/0555 324/309 |
| 2011/0048424 A1 | 3/2011 | Radko | |
| 2011/0113555 A1 | 5/2011 | Smith | |
| 2011/0125010 A1 | 5/2011 | Vaquero Lopez et al. | |
| 2011/0160521 A1 | 6/2011 | Khodak et al. | |
| 2012/0071274 A1 | 3/2012 | Rapoport | |
| 2012/0078034 A1 | 3/2012 | Falk et al. | |
| 2012/0126814 A1 | 5/2012 | Fischer et al. | |
| 2012/0140899 A1 | 6/2012 | Bailey et al. | |
| 2013/0025062 A1 | 1/2013 | Esch | |
| 2013/0109956 A1 | 5/2013 | Rapoport | |
| 2013/0150656 A1 | 6/2013 | Falk et al. | |
| 2013/0204074 A1 | 8/2013 | Belval et al. | |
| 2013/0204617 A1 | 8/2013 | Kuo et al. | |
| 2013/0267765 A1 | 10/2013 | Rapoport | |
| 2013/0334439 A1 | 12/2013 | Etters | |
| 2014/0003614 A1 | 1/2014 | Levitov et al. | |
| 2014/0051976 A1 | 2/2014 | Rapoport et al. | |
| 2014/0055136 A1 | 2/2014 | Leussler et al. | |
| 2014/0078301 A1 | 3/2014 | Fazzi et al. | |
| 2014/0098934 A1 | 4/2014 | Kondo | |
| 2014/0099010 A1 | 4/2014 | Rapoport | |
| 2014/0117989 A1 | 5/2014 | Rapoport | |
| 2014/0354279 A1 | 12/2014 | Dumoulin et al. | |
| 2014/0357981 A1 | 12/2014 | Dumoulin | |
| 2014/0364722 A1 | 12/2014 | Dumoulin | |
| 2015/0137812 A1 | 5/2015 | Rapoport | |
| 2015/0141799 A1 | 5/2015 | Rapoport et al. | |
| 2016/0030264 A1 | 2/2016 | Lehmann et al. | |
| 2016/0081582 A1 | 3/2016 | Rapoport | |

FOREIGN PATENT DOCUMENTS

| | | |
|---|---|---|
| CN | 102551719 A | 7/2012 |
| DE | 19617739 | 6/1997 |
| EP | 1132072 | 9/2001 |

(56) References Cited

FOREIGN PATENT DOCUMENTS

| | | |
|---|---|---|
| EP | 2581071 | 4/2013 |
| IL | 226488 | 5/2013 |
| JP | 2004531313 | 10/2004 |
| JP | 2005514078 | 5/2005 |
| JP | 2007252741 | 10/2007 |
| JP | 2010178857 | 8/2010 |
| JP | 2016539683 | 12/2016 |
| WO | WO/1998/048756 | 11/1998 |
| WO | WO9921526 | 5/1999 |
| WO | WO2008137003 | 11/2008 |
| WO | WO2010054457 | 5/2010 |
| WO | WO2011109761 | 9/2011 |
| WO | WO 2012/143825 A1 | 10/2012 |
| WO | WO2013/115847 | 8/2013 |
| WO | WO/2014/188425 | 11/2014 |

OTHER PUBLICATIONS

U.S. Appl. No. 61/905,221, filed Nov. 17, 2013, Rapoport.
U.S. Appl. No. 61/899,233, filed Nov. 3, 2013, Rapoport.
U.S. Appl. No. 61/940,514, filed Feb. 17, 2014, Rapoport.
International Search Report for PCT Application No. PCT/IL2014/50450 dated Sep. 16, 2014.
International Preliminary Report on Patentability for PCT Application No. PCT/IL2014/50450 dated May 8, 2015.
International Search Report for PCT Application No. PCT/IL2014/50452 dated Sep. 19, 2014.
Antonucci, et al., The infant incubator in the neonatal intensive care unit: unresolved issues and future developments, J. Perinat. Med. 37(2009), 587-598.
Baby Pod II Infant Transport Device, Advance Healthcare Technology, brochure, pp. 1-6.
Baby Pod II Operation and Maintenance Manual, revision 5, Jan. 2011, pp. 1-11.
Ferris et al., The design of neonatal incubators: a systems-oriented, human centered approach, J. Perinatology, 2013, 33, S24-S31.
Kitterman et al., Catheterization of umbilical vessels in newborn infants, Pediatric Clinics of North America, vol. 17, No. 4, Nov. 1970, 895-912.
Paley et al., An MR-compatible neonatal incubator, The British Journal of Radiology, 85, 2012, 952-958.
American National Standard, Medical Electrical Equipment—Parts 2-19: Particular requirements tor the basic safety and essential performance of infant incubators, Association for the advancement of medical instrumentation, ANSI/AAI/IEC 60601-2-19:2009, pp. 1-19.
Jenkins, S., ScanPod, BabyPod—Products—ScanPod, 2002-2011 Advance Healthcare Technology, ltd., internet website http://babypod.com:80/products/scanpod.php.
Science Daily, Inside the preemie brain, Incubator enables MRI scans on premeeies for preventing birth asphyxia, Dec. 1, 2005, pp. 1-2, Web address: http://web.archive.org/web/20130303154220/http://www.sciencedaily.com/videos/2005/1211-inside_the_preemie_brain.htm
Thermaxx Jackets, 5 most common thermal insulation materials, pp. 1-4, internet: https://www.thermaxxjackets.com/5-most-common-thermal-insulation-materials/.
Kim et al., Air transparent soundproof window, AIP Advances 4, 117123 (2014), published online, https://doi.org/10.1063/1.4902155.
Knutson, Allysa Jennie, Acceptable noise levels for neonates in the neonatal intensive care unit, A Capstone Project submitted in partial fulfillment of the requirements for the degree of: Doctor of Audiology, Washington University School of Medicine Program in Audiology and Communication Sciences, May 17, 2013, pp. 1-59.
Liu, Lichuan et al., Development and Applications of Active Noise Control System for Infant Incubators, Proceedings of the 2009 IEEE International Conference on Systems, Man, and Cybernetics San Antonio, TX, USA—Oct. 2009, pp. 1-6.
Mahil et al., Hybrid Swarm Algorithm for the Suppression of Incubator Interference in Premature Infants ECG, Research Journal of Applied Sciences, Engineering and Technology 6(16): 2931-2935, 2013.
Marik et al., Neonatal incubators: A toxic sound environment for the preterm infant?, Pediatr Crit Care Med 2012 vol. 13, No. 6, pp. 1-6.
Ranganna et al., Reducing noise on the neonatal unit, Infant 2011, vol. 7, Issue 1, pp. 25-28.

* cited by examiner

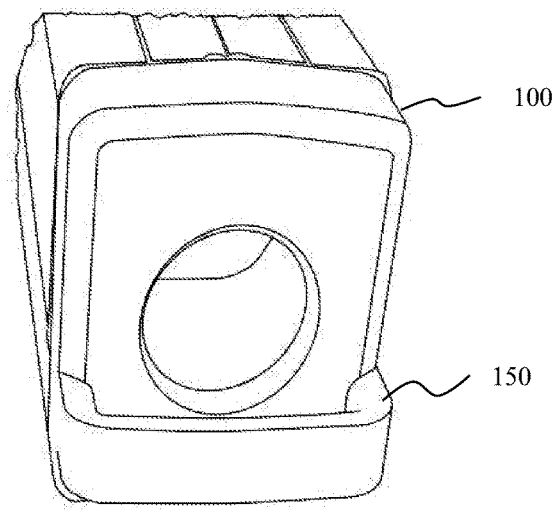
Fig. 2A
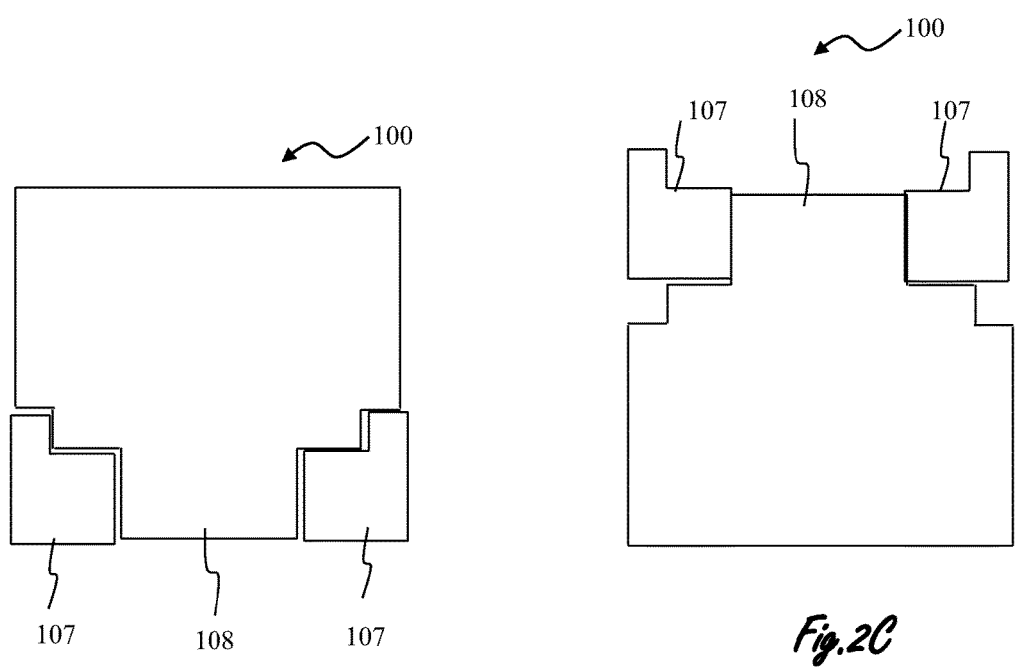
Fig. 2B
Fig. 2C

INSTALLABLE RF COIL ASSEMBLY

REFERENCE TO RELATED APPLICATIONS

IL Pat. Appl. 226488, filed 21 May 2013, titled: "A CRADLE FOR NEONATES", of which is hereby incorporated by reference in its entirety.

U.S. Provisional Patent Application 61/940,514, filed 17 Feb. 2014, titled: "AN INCUBATOR DEPLOYABLE MULTI-FUNCTIONAL PANEL", of which is hereby incorporated by reference in its entirety.

U.S. Pat. No. 7,719,279 B2, filed 27 May 2008 titled: "SELF-FASTENING CAGE SURROUNDING A MAGNETIC RESONANCE DEVICE AND METHODS THEREOF", of which is hereby incorporated by reference in its entirety.

U.S. Pat. No. 8,147,396 B2, filed 24 Nov. 2004 titled: "NEONATE IMAGING SUB SYSTEM", of which is hereby incorporated herein as a reference in its entirety.

U.S. Pat. No. 8,217,653 B2, filed 20 Feb. 2009 titled: "MULTI-CHANNEL RF COIL SYSTEM WITH MULTI-CHANNEL RF COIL TRANSCEIVER DETECTING MORE THAN ONE FREQUENCY AT THE SAME TIME FOR MAGNETIC RESONANCE IMAGING SYSTEMS AND METHODS", of which is hereby incorporated herein as a reference in its entirety.

US Pat. Appl. 20140055136 A1, filed 13 Apr. 2012 titled: "MULTICHANNEL RF VOLUME RESONATOR FOR MRI", of which is hereby incorporated herein as a reference in its entirety.

U.S. Pat. No. 8,390,288 B2, filed 24 Apr. 2008, titled: "METHOD AND RF TRANSMITTER ARRANGEMENT FOR GENERATING RF FIELDS", of which is hereby incorporated herein as a reference in its entirety.

FIELD OF THE INVENTION

The present invention generally relates to the field of magnetic resonance imaging (MRI), and more particularly to an installable RF coil assembly and methods thereof.

BACKGROUND OF THE INVENTION

MRI technology utilizes magnetism and radio frequency to create three-dimensional sections or layered images of body organs or tissue for medical diagnosis and research. These images greatly improve the ability of doctors to distinguish abnormal from healthy tissues. MRI can also be used to observe and measure dynamic physiological changes inside a patient without cutting into or penetrating the body. Conventional MRI devices consist of a closed tube into which the patient is inserted for the purpose of the examination. To produce an image, an MRI device uses a powerful magnet to generate a magnetic field. When a patient lies within this field, the nuclei of atoms within the body align themselves with the magnetic field. Radio waves are then pulsed through the body, causing the nuclei to change their alignment with respect to the axis of the magnetic lines of force. As they return to their previous state after each pulse, they produce faint, distinctive radio signals; the rate at which they emit signals and the frequency of the signals depend on the type of atom, the temperature, the chemical environment, position, and other factors. These signals are detected by coils around the body and processed by a computer to produce images of internal structures. Radiofrequency coils are a major part of the radiofrequency (RF) system in the magnetic resonance imaging hardware. They consist of two electromagnetic coils, the transmitter and receiver coils generating and receiving electromagnetic fields. The receiver coil picks up the RF electromagnetic radiation produced by nuclear relaxation inside the subject There are two major types of RF coils: volume coils and surface coils. Volume coils are configured to provide a homogeneous RF excitation across a large volume. Most clinical MRI scanners include a built in volume coil to perform whole-body imaging, and smaller volume coils have been constructed for the head and other extremities. These coils require a great deal of RF power because of their size, so they are often driven in quadrature in order to reduce by two the RF power requirements. Further, volume coils are undesirable when scanning a small area because they receive noise from the entire volume, not just the region of interest.

Surface coils are designed to provide a very high RF sensitivity over a small region of interest. These coils are usually placed directly over the anatomy of interest. The surface coils make good receivers as they detect noise only from the area of interest, but they provide low RF homogeneity if used for transmission.

U.S. Pat. No. 8,217,653 B2, filed 20 Feb. 2009 titled: "MULTI-CHANNEL RF COIL SYSTEM WITH MULTI-CHANNEL RF COIL TRANSCEIVER DETECTING MORE THAN ONE FREQUENCY AT THE SAME TIME FOR MAGNETIC RESONANCE IMAGING SYSTEMS AND METHODS", discloses an RF coil system for magnetic resonance applications includes a multi-channel RF coil transceiver and a multi-channel RF coil. The RF coil system is structured for reconfiguration between a plurality of operational modes.

US Pat. application 20140055136 A1, filed 13 Apr. 2012 titled "MULTICHANNEL RF VOLUME RESONATOR FOR MRI", discloses an RF volume resonator system comprising a multi-port RF volume resonator, like e.g. a TEM volume coil or TEM resonator, or a birdcage coil, all of those especially in the form of a local coil like a head coil, or a whole body coil, and a plurality of transmit and/or receive channels for operating the multi-port RF volume resonator for transmitting RF excitation signals and/or for receiving MR relaxation signals into/from an examination object or a part thereof.

U.S. Pat. No. 8,390,288 B2, filed 24 Apr. 2008, titled: "METHOD AND RF TRANSMITTER ARRANGEMENT FOR GENERATING RF FIELDS", discloses a multi-channel RF transmitter arrangement comprising a plurality of RF transmitter elements like RE antennas, antenna elements, coils or coil elements, for generating an RF field, especially for use in a magnetic resonance imaging system for exciting nuclear magnetic resonances, and a method for generating such an RF field wherein the RF transmitter elements are segmented in a plurality of segments at least along the direction of one or more of the main magnetic field of the MRI system, the z-direction or the longitudinal direction.

With the increasing number of premature births and good surviving prognosis for premature neonates born at an early gestation age as 24 weeks the need for neonates imaging techniques, such as magnetic resonance imaging, that are noninvasive and do not involve ionizing radiation for their function.

When considering magnetic resonance imaging of neonates several parameters and precautions must be considered. New born and ill babies are usually kept in an incubator especially designed for maintaining constant environmental conditions such as temperature and humidity fitting for life supporting the baby. In addition in the incubator, functioning as an intensive care unit, provides the baby with connections to various medical devices and monitors to facilitate and overview breathing, feeding, fluid exchange and cardiac activity. Babies and neonates are also sensitive to excess light, noise, vibration and handling, and so these must be minimized to benefit recovery. Any transfer or movement of the baby may require the transfer or reconnection of attached medical devices, posing an additional stress on the baby. Further, any changes in location of the neonate may expose him to infection from an unprotected environment. The neonate must be kept in a life supporting environment, usually connected to life supporting equipment and monitoring devices, in order to maintain respiratory and cardiovascular functions, body temperature, and fluid and electrolyte homeostasis.

Since MRI imaging utilizes a strong magnet, care must be taken to insure that all elements and equipment in the vicinity of the MRI are 'MRI safe', meaning that they are not magnetic, not conductive, and not RF reactive. Many accidents were reported when metallic items were pulled in by the force of the magnetic field and harmed a patient during imaging. Another important parameter is to insure that the permeability of materials surrounding the neonate (for example the incubator material) to magnetic fields and radio frequency waves, is such that it does not disturb the image received.

Other risks may be peripheral nerve stimulation, exposure to a loud noise (up to 120 dB), generated by the rapid switching of the magnetic field gradients, or overheating may occur due to absorption of the energy that is utilized to generate the magnetic spin. This risk is especially enhanced considering the neonate's high ratio of surface area to body volume, and their immature body temperature regulation. Thus, neonates should be kept in an MRI-safe incubator providing a life supporting internal environment, and further buffering the conditions of the external environment such as noise, light, temperature, humidity, and etc.

Another risk involves an unintentional shut-down of a superconducting electromagnet ("quench"), resulting in the rapid boiling of liquid helium from the device. The rapidly expanding helium if released into the scanner room may cause displacement of the oxygen and present a risk of asphyxiation. In order to minimize risks and maintain homogenous conditions, a constant low temperature is kept in the MRI room. Further, to limit complications, the neonate should be kept in a device enabling easy access and rapid evacuation if needed.

Magnetic resonance devices are usually placed in dedicated especially designed RF shielded rooms, necessitating the transfer of neonates in need of a scan to a remote location. It is a long felt need to transport between a premature neonate intensive-care ward and an MRI imaging facility, without decoupling and disconnecting the premature neonate from life-support systems, and executing the imaging process with as little handling of the neonate as possible.

The known MRI compatible incubators, such as those manufactured by Advanced Imaging Research (Cleveland, Ohio), that are equipped with RF coils require the transfer of the neonate from a standard intensive care incubator into the MRI compatible incubator. In these arrangements, the RF coils are stationary in position after installation, and do not enable temporary position shifting for accessing the neonate. Another commercially available magnetic resonance compatible incubator is the Lammers Medical Technology GmbH (LMT), in which the head coil is available only as an accessory completely detachable from the incubator. This accessory requires the movement of the neonate in order to be installed. Further the LMT MRI compatible incubator needs to be lifted from the trolley and inserted into the open bore.

The RF coils known in the art cannot be installed on an MRI compatible incubator such that the RF coil can be easily manipulated in at least two vectors, between two positions, without moving the neonate in order to install the coil, position it, or for the imaging process.

There is a long felt and an unmet need to provide an MRI-compatible neonate's cradle, cart, and/or MRI-cart-cradle assembly comprising a maneuverable RF coil and methods for both (i) applying an RF coil over a neonate immobilized within his/her cradle and (ii) conveniently removing the RF coil from the neonate and safely placing it when it is not required for imaging.

SUMMARY OF THE INVENTION

The present invention provides a maneuverable RF coil assembly (MRCA), useful for being maneuvered at both positions: (i) over at least a portion of a neonate immobilized within a cradle at time of MR imaging; and (ii) below or aside the cradle when it is not required for imaging, comprising at least one RF coil and maneuvering mechanism; wherein the maneuvering mechanism comprises both: (i) a linear reciprocating mechanism for approaching or otherwise drawing away at least one coil to and from the neonate; and (ii) tilting mechanism for placing at least one coil away from the neonate.

It is another object of the current invention to disclose the MRCA defined in any of the above, wherein the RF coil maneuvering mechanism is configured to enable a plurality of consecutively maneuverable movement vectors.

It is another object of the current invention to disclose the MRCA defined in any of the above, wherein the maneuvering mechanism is configured to provide a plurality of positions for the RF coil adjacent to the neonate.

It is another object of the current invention to disclose the MRCA defined in any of the above, wherein the RF coil is configured to close an opening of an incubator when in at least one position.

It is another object of the current invention to disclose the MRCA defined in any of the above, wherein at least one of the following holds true: (a) the assembly comprises a handle configured for maneuvering the RF coil assembly by a handler; (b) the maneuvering mechanism is selected from a group consisting of: automated, manual, semi-automated, remote controlled, and any combination thereof; (c) the assembly comprises a least one latch configured to secure at least one position of the RF coil assembly; (d) the RF coil assembly comprises at least one sensor configured to sense a selected from a group consisting of: structural integrity of the RF coil, structural integrity of the maneuvering mechanism, position of RF coil, proximity of the neonate to the RF coil, RF signal received, RF signal transmitted, and any combination thereof; and, (e) the RF coil assembly is reversibly detachable from the cradle.

It is another object of the current invention to disclose the MRCA defined in any of the above, wherein at least one of the following holds true: (a) the RF coil assembly comprises a plurality of RF coils; (b) the RF coil is configured to connect to at least a second RF coil; and, (c) the RF coil is connected to at least a second RF coil by a maneuverable connection.

It is another object of the current invention to disclose the MRCA defined in any of the above, wherein at least one of the following holds true: (a) the cradle is supported by a MRI safe cart; (b) the cradle is supported by a MRI safe cart, at least a portion thereof is insertable to a selected from a group consisting of: into an MRD bore, into a transport device, into a treatment device, into a storage device and any combination thereof; and, (c) the RF coil assembly, in connection with the cradle is supported by an MRI safe cart, is configured to be at least partially insertable into an MRD bore.

It is another object of the current invention to disclose the MRCA defined in any of the above, wherein the RF assembly and cradle are sized and shaped to be at least partially accommodated within an MRD bore.

It is another object of the current invention to disclose the MRCA defined in any of the above, wherein at least one of the following holds true: (a) the RF coil is selected from a group consisting of: solenoid, planar, volume, surface, quadrature, and any combination thereof; (b) the RF coil is a multi-tuned RF coil; and, (c) the RF coil assembly comprises a multi-channel RF coil; further wherein the RF coil assembly is reconfigurable between pluralities of operational modes.

It is another object of the current invention to disclose the MRCA defined in any of the above, wherein the assembly is sized and shaped to accommodate at least a portion of the neonate.

It is another object of the current invention to disclose the MRCA defined in any of the above, wherein the cradle comprises an emergency release mechanism configured for immediate release of the neonate from the cradle.

It is another object of the current invention to disclose the MRCA defined in any of the above, wherein the RF coil comprises an emergency release mechanism configured for immediate release of the RF coil from the cradle.

It is another object of the current invention to disclose the MRCA defined in any of the above, wherein the cradle comprises life support equipment for the neonate.

It is another object of the current invention to disclose the MRCA defined in any of the above, wherein the cradle comprises means for maintaining the position of the neonate.

It is another object of the current invention to disclose the MRCA defined in any of the above, wherein the cradle comprises an envelope surrounding an internal environment in which the neonate is accommodated.

It is another object of the current invention to disclose the MRCA defined in any of the above, wherein the maneuverable mechanism is configured to allow movement of the RF coil assembly within the internal environment, external to the internal environment or both.

It is another object of the current invention to disclose the MRCA defined in any of the above, wherein the RF coil is configured to have at least one position forming a closed environment incubator.

It is another object of the current invention to disclose the MRCA defined in any of the above, wherein the cradle is selected from a group consisting of: an incubator, a deployed incubator, a transport incubator, a treatment table, a countertop, an operating table, a bed, a baby cradle, a basket, a mattress, a stretcher, a gurney, and any combination thereof.

It is another object of the current invention to disclose the MRCA defined in any of the above, wherein the cradle comprises a selected from a group consisting of: at least one sensor, at least one indicator, at least one medical equipment tubing placement, at least one opening fitted for the insertion of a handlers hand, at least one opening for the passage of life supporting equipment, and any combination thereof.

It is another object of the current invention to disclose the MRCA defined in any of the above, wherein the cradle comprises a user interface configured to monitor or control a selected from a group consisting of: life supporting equipment, MRI operation, position of RF coil, RF coil maneuvering mechanism, opening or closing the cradle, and any combination thereof.

It is another object of the current invention to disclose the MRCA defined in any of the above, wherein the maneuverable mechanism comprises means selected from a group consisting of: sliding mechanism, pivot point mechanism, hinge, telescopic mechanism, hydraulic mechanism, turning mechanism, and any combination thereof.

It is another object of the current invention to disclose the MRCA defined in any of the above, wherein at least a portion of the assembly and cradle are made of a material selected from a group consisting of: a MRI safe material, at least partially transparent material, a sterilizable material, a fire retardant material, and any combination thereof.

It is another object of the current invention to disclose the MRCA defined in any of the above, wherein at least a portion of the RF coil is integrated into MRI-safe material.

It is another object of the current invention to disclose the MRCA defined in any of the above, wherein at least a portion of the cart is made of MRI safe material.

It is another object of the current invention to disclose the MRCA defined in any of the above, wherein the cart comprises means for maneuvering the cradle providing movement selected from a group consisting of: rotational, tilt, vertical shift, horizontal shift, and any combination thereof.

It is another object of the current invention to disclose the MRCA defined in any of the above, wherein the RF coil assembly comprises a hinge mechanism configured to enable maneuvering of the RF coil in an axis perpendicular to the linearly reciprocating axis.

It is another object of the current invention to disclose the MRCA defined in any of the above, wherein the RF coil is a transmitting coil, a receiving coil, or both.

It is another object of the current invention to disclose the MRCA defined in any of the above, wherein the maneuvering mechanism is configured to accept different RF coil assemblies as modular pieces.

It is another object of the current invention to disclose the MRCA defined in any of the above, wherein the maneuverable mechanism is configured to accept more than one RF coil assembly, and maneuver the assemblies in a manner selected from a group consisting of: all together, each separately, one following the other, maintaining a predetermined spatial interaction between the assemblies, coordinated movement configured to best fit neonate, movement configured to respond to feedback from MR signal received of the neonate, and any combination thereof. The present invention provides a multi-functional maneuvering mechanism (MMM) for maneuvering an RF coil assembly to and from at least two positions: (i) over at least a portion of a neonate immobilized within a cradle at time of MR imaging; and (ii) below or aside the cradle when it is not required for imaging, comprising at least one RF coil and maneuvering mechanism; wherein the multi-functional maneuvering mechanism comprises (i) at least one first linear reciprocating mechanism for approaching or otherwise drawing away at least one coil to and from the neonate; and (ii) at least one second tilting mechanism for placing at least one coil away from the neonate.

It is another object of the current invention to disclose the MMM defined in any of the above, wherein the RF coil maneuvering mechanism is configured to enable a plurality of consecutively maneuverable movement vectors.

It is another object of the current invention to disclose the MMM defined in any of the above, wherein the maneuvering mechanism is configured to provide a plurality of positions for the RF coil adjacent to the neonate.

It is another object of the current invention to disclose the MMM defined in any of the above, wherein the RF coil is configured to close an opening of an incubator when in at least one position.

It is another object of the current invention to disclose the MMM defined in any of the above, wherein at least one of the following holds true: (a) the assembly comprises a handle configured for maneuvering the RF coil assembly by a handler; (b) the maneuvering mechanism is selected from a group consisting of: automated, manual, semi-automated, remote controlled, and any combination thereof; (c) the assembly comprises a least one latch configured to secure at least one position of the RF coil assembly; (d) the RF coil assembly comprises at least one sensor configured to sense a selected from a group consisting of: structural integrity of the RF coil, structural integrity of the maneuvering mechanism, position of RF coil, proximity of the neonate to the coil, RF signal received, RF signal transmitted, and any combination thereof; and, (e) the RF coil assembly is reversibly detachable from the cradle.

It is another object of the current invention to disclose the MMM defined in any of the above, wherein at least one of the following holds true: (a) the RF coil assembly comprises a plurality of RF coils; (b) the RF coil is configured to connect to at least a second RF coil; and, (c) the RF coil is connected to at least a second RF coil by a maneuverable connection.

It is another object of the current invention to disclose the MMM defined in any of the above, wherein at least one of the following holds true: (a) the cradle is supported by a MRI safe cart; (b) the cradle is supported by a MRI safe cart, at least a portion thereof is insertable to a selected from a group consisting of: into an MRD bore, into a transport device, into a treatment device, into a storage device and any combination thereof; and, (c) the RF coil assembly, in connection with the cradle is supported by an MRI safe cart, is configured to be at least partially insertable into an MRD bore.

It is another object of the current invention to disclose the MMM defined in any of the above, wherein the RF assembly and cradle are sized and shaped to be at least partially accommodated within an MRD bore.

It is another object of the current invention to disclose the MMM defined in any of the above, wherein at least one of the following holds true: (a) the RF coil is selected from a group consisting of: solenoid, planar, volume, surface, quadrature, and any combination thereof; (b) the RF coil is a multi-tuned RF coil; and, (c) the RF coil assembly comprises a multi-channel RF coil; further wherein the RF coil assembly is reconfigurable between pluralities of operational modes.

It is another object of the current invention to disclose the MMM defined in any of the above, wherein the assembly is sized and shaped to accommodate at least a portion of the neonate.

It is another object of the current invention to disclose the MMM defined in any of the above, wherein the cradle comprises an emergency release mechanism configured for immediate release of the neonate from the cradle.

It is another object of the current invention to disclose the MMM defined in any of the above, wherein the RF coil comprises an emergency release mechanism configured for immediate release of the RF coil from the cradle.

It is another object of the current invention to disclose the MMM defined in any of the above, wherein the cradle comprises life support equipment for the neonate.

It is another object of the current invention to disclose the MMM defined in any of the above, wherein the cradle comprises means for maintaining the position of the neonate.

It is another object of the current invention to disclose the MMM defined in any of the above, wherein the cradle comprises an envelope surrounding an internal environment in which the neonate is accommodated.

It is another object of the current invention to disclose the MMM defined in any of the above, wherein the maneuverable mechanism is configured to allow movement of the RF coil assembly within the internal environment, external to the internal environment or both.

It is another object of the current invention to disclose the MMM defined in any of the above, wherein the RF coil is configured to have at least one position forming a close environment incubator.

It is another object of the current invention to disclose the MMM defined in any of the above, wherein the cradle is selected from a group consisting of: an incubator, a deployed incubator, a transport incubator, a treatment table, a countertop, an operating table, a bed, a baby cradle, a basket, a mattress, a stretcher, a gurney, and any combination thereof.

It is another object of the current invention to disclose the MMM defined in any of the above, wherein the cradle comprises a selected from a group consisting of: at least one sensor, at least one indicator, at least one medical equipment tubing placement, at least one opening fitted for the insertion of a handlers hand, at least one opening for the passage of life supporting equipment, and any combination thereof.

It is another object of the current invention to disclose the MMM defined in any of the above, wherein the cradle comprises a user interface configured to monitor or control a selected from a group consisting of: life supporting equipment, MRI operation, position of RF coil, RF coil maneuvering mechanism, opening or closing the cradle, and any combination thereof.

It is another object of the current invention to disclose the MMM defined in any of the above, wherein the maneuverable mechanism comprises means selected from a group consisting of: sliding mechanism, pivot point mechanism, hinge, telescopic mechanism, hydraulic mechanism, turning mechanism, and any combination thereof.

It is another object of the current invention to disclose the MMM defined in any of the above, wherein at least a portion of the assembly and cradle are made of a material selected from a group consisting of: a MRI safe material, at least partially transparent material, a sterilizable material, a fire retardant material, and any combination thereof.

It is another object of the current invention to disclose the MMM defined in any of the above, wherein the RF coil is connected to at least a second RF coil by a maneuverable connection.

It is another object of the current invention to disclose the MMM defined in any of the above, wherein at least a portion of the RF coil is integrated into MRI-safe material.

It is another object of the current invention to disclose the MMM defined in any of the above, wherein the cart comprises means for maneuvering the cradle providing movement selected from a group consisting of: rotational, tilt, vertical shift, horizontal shift, and any combination thereof.

It is another object of the current invention to disclose the MMM defined in any of the above, wherein the RF coil assembly comprises a hinge mechanism configured to enable maneuvering of the RF coil in an axis perpendicular to the linearly reciprocating axis.

It is another object of the current invention to disclose the MMM defined in any of the above, wherein the RF coil is a transmitting coil, a receiving coil, or both.

It is another object of the current invention to disclose the MMM defined in any of the above, wherein the maneuvering mechanism is configured to accept different RF coil assemblies as modular pieces.

It is another object of the current invention to disclose the MMM defined in any of the above, wherein the maneuverable mechanism is configured to accept more than one RF coil assembly, and maneuver the assemblies in a manner selected from a group consisting of: all together, each separately, one following the other, maintaining a predetermined spatial interaction between the assemblies, coordinated movement configured to best fit neonate, movement configured to respond to feedback from MR signal received of the neonate, and any combination thereof.

The present invention provides a method of maneuvering an RF coil, comprising at least two different steps: a step of (i) linearly reciprocating an RF coil assembly for approaching or otherwise drawing away at least one coil to and from a neonate to be MR imaged; and then (ii) tilting the RF coil assembly for placing at least one coil away from the neonate when the neonate is not MR imaged.

It is another object of the current invention to disclose the method defined in any of the above, additionally comprising a step of selecting the assembly sized and shaped to accommodate at least a portion of the neonate.

It is another object of the current invention to disclose the method defined in any of the above, additionally comprising a step of connecting the cradle to the RF coil by a maneuverable mechanism thereby enabling the RF coil to be positioned in a plurality of positions adjacent to the neonate.

It is another object of the current invention to disclose the method defined in any of the above, additionally comprising a step of selecting the cradle having an emergency release mechanism, and configuring the mechanism to immediately release the neonate from the cradle when in need.

It is another object of the current invention to disclose the method defined in any of the above, additionally comprising a step of selecting the RF coil having an emergency release mechanism, and configuring the mechanism for immediately releasing the RF coil from the cradle.

It is another object of the current invention to disclose the method defined in any of the above, additionally comprising a step of connecting neonate life support equipment to the cradle, the neonate or both.

It is another object of the current invention to disclose the method defined in any of the above, additionally comprising a step of selecting the cradle having means for maintaining the position of the neonate and utilizing the means for maintaining the body position of the neonate.

It is another object of the current invention to disclose the method defined in any of the above, additionally comprising a step of selecting the cradle having an envelope surrounding an internal environment in which the neonate is accommodated.

It is another object of the current invention to disclose the method defined in any of the above, additionally comprising a step of selecting the maneuverable mechanism configured to allow movement of the RF coil assembly within the internal environment, external to the internal environment or both.

It is another object of the current invention to disclose the method defined in any of the above, additionally comprising a step of moving the RF coil assembly within the internal environment, external to the internal environment or both.

It is another object of the current invention to disclose the method defined in any of the above, additionally comprising a step of selecting the RF coil configured to have at least one position forming a close environment incubator.

It is another object of the current invention to disclose the method defined in any of the above, additionally comprising a step of selecting the cradle from a group consisting of: an incubator, a deployed incubator, a transport incubator, a treatment table, a countertop, an operating table, a bed, a baby cradle, a basket, a mattress, a stretcher, a gurney, and any combination thereof.

It is another object of the current invention to disclose the method defined in any of the above, additionally comprising a step of selecting the RF coil configured for closing an opening of an incubator when in at least one position.

It is another object of the current invention to disclose the method defined in any of the above, additionally comprising a step of selecting the cradle having a selected from a group consisting of: at least one sensor, at least one indicator, at least one medical equipment tubing placement, at least one opening fitted for the insertion of a handlers hand, at least one opening for the passage of life supporting equipment, and any combination thereof.

It is another object of the current invention to disclose the method defined in any of the above, additionally comprising a step of selecting the cradle having a user interface configured for monitoring or controlling a selected from a group consisting of: life supporting equipment, MRI operation, position of RF coil, RF coil maneuvering mechanism, opening or closing the cradle, and any combination thereof.

It is another object of the current invention to disclose the method defined in any of the above, additionally comprising at least one of the following steps: (a) monitoring a selected from a group consisting of: life supporting equipment, MRI operation, position of RF coil, RF coil maneuvering mechanism, opening or closing the cradle, and any combination thereof or, (b) controlling a selected from a group consisting of: life supporting equipment, MRI operation, position of RF coil, RF coil maneuvering mechanism, opening or closing the cradle, and any combination thereof.

It is another object of the current invention to disclose the method defined in any of the above, additionally comprising a step of selecting the RF coil having at least one sensor configured to sense a selected from a group consisting of: structural integrity of the RF coil, structural integrity of the maneuvering mechanism, position of RF coil, proximity of the neonate to the coil, RF signal received, RF signal transmitted, and any combination thereof.

It is another object of the current invention to disclose the method defined in any of the above, additionally comprising a step of selecting the sensor connected to at least one indicator, and receiving an indication from the sensor.

It is another object of the current invention to disclose the method defined in any of the above, additionally comprising a step of selecting the assembly having a handle configured for operation by a handler, and maneuvering the handle, thereby maneuvering a selected from a group consisting of: the RF coil, the cradle, neonate restraining means, neonate mattress, a cart connected to the cradle, and any combination thereof.

It is another object of the current invention to disclose the method defined in any of the above, additionally comprising a step of selecting the maneuvering mechanism from a group consisting of: automated, manual, semi-automated, remote controlled, and any combination thereof, and operating the mechanism.

It is another object of the current invention to disclose the method defined in any of the above, additionally comprising a step of selecting the maneuverable mechanism having maneuverable means selected from a group consisting of: sliding mechanism, pivot point mechanism, hinge, telescopic mechanism, hydraulic mechanism, turning mechanism, and any combination thereof.

It is another object of the current invention to disclose the method defined in any of the above, additionally comprising a step of selecting a cradle in connection with an RF assembly having at least a portion of the assembly and/or cradle are made of a material selected from a group consisting of: a MRI safe material, at least partially transparent material, a sterilizable material, a fire retardant material, and any combination thereof.

It is another object of the current invention to disclose the method defined in any of the above, additionally comprising a step of selecting the RF coil assembly having a least one latch configured to secure at least one position of the RF coil assembly, and securing or releasing the RF coil assembly.

It is another object of the current invention to disclose the method defined in any of the above, additionally comprising a step of reversibly detaching the RF coil from the cradle.

It is another object of the current invention to disclose the method defined in any of the above, additionally comprising a step of selecting the RF coil configured to connect to at least a second RF coil, and connecting at least a second RF coil.

It is another object of the current invention to disclose the method defined in any of the above, additionally comprising a step of selecting the RF coil connected to at least a second RF coil by a maneuverable connection, and maneuvering the RF coil relative to at least a second RF coil.

It is another object of the current invention to disclose the method defined in any of the above, additionally comprising a step of selecting the RF coil of which at least a portion of is integrated into MRI-safe material.

It is another object of the current invention to disclose the method defined in any of the above, additionally comprising a step of supporting the cradle in connection with an RF coil assembly by a cart.

It is another object of the current invention to disclose the method defined in any of the above, additionally comprising a step of selecting the cart in which at least a portion of is made of MRI safe material.

It is another object of the current invention to disclose the method defined in any of the above, additionally comprising a step of selecting the cart in which at least a portion of is insertable to a selected from a group consisting of: into an MRD bore, into a transport device, into a treatment device, into a storage device, and any combination thereof.

It is another object of the current invention to disclose the method defined in any of the above, additionally comprising a step of selecting the cart having means for maneuvering the cradle providing movement selected from a group consisting of: rotational, tilt, vertical shift, horizontal shift, and any combination thereof, and maneuvering the cradle.

It is another object of the current invention to disclose the method defined in any of the above, additionally comprising a step of selecting the RF assembly, in connection with the cradle and the cart configured to be at least partially insertable into an MRD bore.

It is another object of the current invention to disclose the method defined in any of the above, additionally comprising a step of selecting the RF assembly and cradle sized and shaped to be at least partially accommodated within an MRD bore.

It is another object of the current invention to disclose the method defined in any of the above, additionally comprising a step of selecting the RF coil assembly having a hinge mechanism, thereby enabling maneuvering of the RF coil in an axis perpendicular to the linearly reciprocating axis.

It is another object of the current invention to disclose the method defined in any of the above, additionally comprising a step of selecting the RF coil assembly having a plurality of RF coils.

It is another object of the current invention to disclose the method defined in any of the above, additionally comprising a step of transmitting, receiving, or both with the RF coil.

It is another object of the current invention to disclose the method defined in any of the above, additionally comprising a step of selecting the RF coil from a group consisting of: solenoid, planar, volume, surface, quadrature, and any combination thereof.

It is another object of the current invention to disclose the method defined in any of the above, additionally comprising a step of selecting the RF coil configured to be a multiply tuned RF coil.

It is another object of the current invention to disclose the method defined in any of the above, additionally comprising a step of selecting the RF coil comprising a multi-channel RF coil, and reconfiguring the RF coil between pluralities of operational modes.

It is another object of the current invention to disclose the method defined in any of the above, additionally comprising a step of selecting the maneuvering mechanism is configured to accept different RF coil assemblies as modular pieces, and connecting at least one modular RF coil assembly.

It is another object of the current invention to disclose the method defined in any of the above, additionally comprising a step of selecting the maneuverable mechanism configured to accept more than one RF coil assembly, and maneuvering the assemblies in a manner selected from a group consisting of: all together, each separately, one following the other, maintaining a predetermined spatial interaction between the assemblies, coordinated movement configured to best fit neonate, movement configured to respond to feedback from MR signal received of the neonate, and any combination thereof.

The present invention provides a method for both (i) applying at least one RF coil over at least a portion of a neonate immobilized within a cradle and (ii) conveniently removing the RF coil from the neonate and safely placing it when it is not required for imaging; comprising at least two different steps of maneuvering an RF coil: a step of (i) linearly reciprocating an RF coil assembly for approaching or otherwise drawing away at least one coil to and from a neonate to be MR imaged; and then (ii) tilting the RF coil assembly for placing at least one coil away from the neonate when the neonate is not MR imaged.

It is another object of the current invention to disclose the method defined in any of the above, additionally comprising a step of selecting the assembly is sized and shaped to accommodate at least a portion of the neonate.

It is another object of the current invention to disclose the method defined in any of the above, additionally comprising a step of connecting the cradle to the RF coil by a maneuverable mechanism thereby enabling the RF coil to be positioned in a plurality of positions adjacent to the neonate.

It is another object of the current invention to disclose the method defined in any of the above, additionally comprising a step of selecting the cradle having an emergency release mechanism, and configuring the mechanism to immediately release the neonate from the cradle when in need.

It is another object of the current invention to disclose the method defined in any of the above, additionally comprising a step of selecting the RF coil having an emergency release mechanism, and configuring the mechanism for immediately releasing the RF coil from the cradle.

It is another object of the current invention to disclose the method defined in any of the above, additionally comprising a step of connecting neonate life support equipment to the cradle, the neonate or both.

It is another object of the current invention to disclose the method defined in any of the above, additionally comprising a step of selecting the cradle having means for maintaining the position of the neonate and utilizing the means for maintaining the body position of the neonate.

It is another object of the current invention to disclose the method defined in any of the above, additionally comprising a step of selecting the cradle having an envelope surrounding an internal environment in which the neonate is accommodated.

It is another object of the current invention to disclose the method defined in any of the above, additionally comprising a step of selecting the maneuverable mechanism configured to allow movement of the RF coil assembly within the internal environment, external to the internal environment or both.

It is another object of the current invention to disclose the method defined in any of the above, additionally comprising a step of moving the RF coil assembly within the internal environment, external to the internal environment or both.

It is another object of the current invention to disclose the method defined in any of the above, additionally comprising a step of selecting the RF coil configured to have at least one position forming a close environment incubator.

It is another object of the current invention to disclose the method defined in any of the above, additionally comprising a step of selecting the cradle from a group consisting of: an incubator, a deployed incubator, a transport incubator, a treatment table, a countertop, an operating table, a bed, a baby cradle, a basket, a mattress, a stretcher, a gurney, and any combination thereof.

It is another object of the current invention to disclose the method defined in any of the above, additionally comprising a step of selecting the RF coil configured for closing an opening of an incubator when in at least one position.

It is another object of the current invention to disclose the method defined in any of the above, additionally comprising a step of selecting the cradle having a selected from a group consisting of: at least one sensor, at least one indicator, at least one medical equipment tubing placement, at least one opening fitted for the insertion of a handlers hand, at least one opening for the passage of life supporting equipment, and any combination thereof.

It is another object of the current invention to disclose the method defined in any of the above, additionally comprising a step of selecting the cradle having a user interface configured for monitoring or controlling a selected from a group consisting of: life supporting equipment, MRI operation, position of RF coil, RF coil maneuvering mechanism, opening or closing the cradle, and any combination thereof.

It is another object of the current invention to disclose the method defined in any of the above, additionally comprising at least one of the following steps: (a) monitoring a selected from a group consisting of: life supporting equipment, MRI operation, position of RF coil, RF coil maneuvering mechanism, opening or closing the cradle, and any combination thereof or, (b) controlling a selected from a group consisting of: life supporting equipment, MRI operation, position of RF coil, RF coil maneuvering mechanism, opening or closing the cradle, and any combination thereof.

It is another object of the current invention to disclose the method defined in any of the above, additionally comprising a step of selecting the RF coil having at least one sensor configured to sense a selected from a group consisting of: structural integrity of the RF coil, structural integrity of the maneuvering mechanism, position of RF coil, proximity of the neonate to the coil, RF signal received, RF signal transmitted, and any combination thereof.

It is another object of the current invention to disclose the method defined in any of the above, additionally comprising a step of selecting the sensor connected to at least one indicator, and receiving an indication from the sensor.

It is another object of the current invention to disclose the method defined in any of the above, additionally comprising a step of selecting the assembly having a handle configured for operation by a handler, and maneuvering the handle, thereby maneuvering a selected from a group consisting of: the RF coil, the cradle, neonate restraining means, neonate mattress, a cart connected to the cradle, and any combination thereof.

It is another object of the current invention to disclose the method defined in any of the above, additionally comprising a step of selecting the maneuvering mechanism from a group consisting of: automated, manual, semi-automated, remote controlled, and any combination thereof, and operating the mechanism.

It is another object of the current invention to disclose the method defined in any of the above, additionally comprising a step of selecting the maneuverable mechanism having maneuverable means selected from a group consisting of: sliding mechanism, pivot point mechanism, hinge, telescopic mechanism, hydraulic mechanism, turning mechanism, and any combination thereof.

It is another object of the current invention to disclose the method defined in any of the above, additionally comprising a step of selecting a cradle in connection with an RF assembly having at least a portion of the assembly and/or cradle are made of a material selected from a group consisting of: a MRI safe material, at least partially transparent material, a sterilizable material, a fire retardant material, and any combination thereof.

It is another object of the current invention to disclose the method defined in any of the above, additionally comprising a step of selecting the RF coil assembly having a least one latch configured to secure at least one position of the RF coil assembly, and securing or releasing the RF coil assembly.

It is another object of the current invention to disclose the method defined in any of the above, additionally comprising a step of reversibly detaching the RF coil from the cradle.

It is another object of the current invention to disclose the method defined in any of the above, additionally comprising a step of selecting the RF coil configured to connect to at least a second RF coil, and connecting at least a second RF coil.

It is another object of the current invention to disclose the method defined in any of the above, additionally comprising a step of selecting the RF coil connected to at least a second RF coil by a maneuverable connection, and maneuvering the RF coil relative to at least a second RF coil.

It is another object of the current invention to disclose the method defined in any of the above, additionally comprising a step of selecting the RF coil of which at least a portion of is integrated into MRI-safe material.

It is another object of the current invention to disclose the method defined in any of the above, additionally comprising a step of supporting the cradle in connection with an RF coil assembly by a cart.

It is another object of the current invention to disclose the method defined in any of the above, additionally comprising a step of selecting the cart in which at least a portion of is made of MRI safe material.

It is another object of the current invention to disclose the method defined in any of the above, additionally comprising a step of selecting the cart in which at least a portion of is insertable to a selected from a group consisting of: into an MRD bore, into a transport device, into a treatment device, into a storage device, and any combination thereof.

It is another object of the current invention to disclose the method defined in any of the above, additionally comprising a step of selecting the cart having means for maneuvering the cradle providing movement selected from a group consisting of: rotational, tilt, vertical shift, horizontal shift, and any combination thereof, and maneuvering the cradle.

It is another object of the current invention to disclose the method defined in any of the above, additionally comprising a step of selecting the RF assembly, in connection with the cradle and the cart configured to be at least partially insertable into an MRD bore.

It is another object of the current invention to disclose the method defined in any of the above, additionally comprising a step of selecting the RF assembly and cradle sized and shaped to be at least partially accommodated within an MRD bore.

It is another object of the current invention to disclose the method defined in any of the above, additionally comprising a step of selecting the RF coil assembly having a hinge mechanism, thereby enabling maneuvering of the RF coil in an axis perpendicular to the linearly reciprocating axis.

It is another object of the current invention to disclose the method defined in any of the above, additionally comprising a step of selecting the RF coil assembly having a plurality of RF coils.

It is another object of the current invention to disclose the method defined in any of the above, additionally comprising a step of transmitting, receiving, or both with the RF coil.

It is another object of the current invention to disclose the method defined in any of the above, additionally comprising a step of selecting the RF coil from a group consisting of: solenoid, planar, volume, surface, quadrature, and any combination thereof.

It is another object of the current invention to disclose the method defined in any of the above, additionally comprising a step of selecting the RF coil configured to be a multiply tuned RF coil.

It is another object of the current invention to disclose the method defined in any of the above, additionally comprising a step of selecting the RF coil comprising a multi-channel RF coil, and reconfiguring the RF coil between pluralities of operational modes.

It is another object of the current invention to disclose the method defined in any of the above, additionally comprising a step of selecting the maneuvering mechanism is configured to accept different RF coil assemblies as modular pieces, and connecting at least one modular RF coil assembly.

It is another object of the current invention to disclose the method defined in any of the above, additionally comprising a step of selecting the maneuverable mechanism configured to accept more than one RF coil assembly, and maneuvering the assemblies in a manner selected from a group consisting of: all together, each separately, one following the other, maintaining a predetermined spatial interaction between the assemblies, coordinated movement configured to best fit neonate, movement configured to respond to feedback from MR signal received of the neonate, and any combination thereof.

It is another object of the current invention to disclose a maneuverable RF coil assembly (MRCA), useful for being maneuvered at both positions: (i) over at least a portion of a neonate immobilized within a cradle at time of MR imaging; and (ii) below or aside the cradle when it is not required for imaging, comprising at least one RF coil and maneuvering mechanism; wherein the maneuvering mechanism comprises both: (i) a linear reciprocating mechanism for approaching or otherwise drawing away at least one coil to and from the neonate; and (ii) tilting mechanism for placing at least one coil away from the neonate; further wherein the RF coil maneuvering mechanism is configured to enable a plurality of consecutively maneuverable movement vectors.

It is another object of the current invention to disclose a maneuverable RF coil assembly (MRCA), useful for being maneuvered at both positions: (i) over at least a portion of a neonate immobilized within a cradle at time of MR imaging; and (ii) below or aside the cradle when it is not required for imaging, comprising at least one RF coil and maneuvering mechanism; wherein the maneuvering mechanism comprises both: (i) a linear reciprocating mechanism for approaching or otherwise drawing away at least one coil to and from the neonate; and (ii) tilting mechanism for placing at least one coil away from the neonate; further wherein the maneuvering mechanism is configured to provide a plurality of positions for the RF coil adjacent to the neonate, when placed at the position of over at least a portion of a neonate.

It is another object of the current invention to disclose a maneuverable RF coil assembly (MRCA), useful for being maneuvered to at least both positions: (i) over at least a portion of a neonate immobilized within a cradle at time of MR imaging; and (ii) below or aside the cradle when it is not required for imaging, comprising at least one RF coil and maneuvering mechanism; wherein the maneuvering mechanism comprises both: (i) a linear reciprocating mechanism for approaching or otherwise drawing away at least one coil to and from the neonate; and (ii) tilting mechanism for placing at least one coil away from the neonate, further wherein the RF coil is configured to close an opening of an incubator when in at least one position.

It is another object of the current invention to disclose a maneuverable RF coil assembly (MRCA), useful for being maneuvered at both positions: (i) over at least a portion of a neonate immobilized within a cradle at time of MR imaging; and (ii) below or aside the cradle when it is not required for imaging, comprising at least one RF coil and maneuvering mechanism; wherein the maneuvering mechanism comprises both: (i) a linear reciprocating mechanism for approaching or otherwise drawing away at least one coil to and from the neonate; and (ii) tilting mechanism for placing at least one coil away from the neonate; further wherein the maneuvering mechanism is configured to provide a plurality of positions for the RF coil adjacent to the neonate, when placed at the position of over at least a portion of a neonate; and further wherein the RF coil is configured to close an opening of an incubator when in at least one position.

It is another object of the current invention to disclose a maneuverable RF coil assembly (MRCA), useful for being maneuvered to at least two positions: (i) over at least a portion of a neonate immobilized within a cradle at time of MR imaging; and (ii) below or aside the cradle when it is not required for imaging, comprising at least one RF coil and maneuvering mechanism; wherein the maneuvering mechanism comprises at least both: (i) a linear reciprocating mechanism for approaching or otherwise drawing away at least one coil to and from the neonate; and (ii) a tilting mechanism for placing at least one coil away from the neonate.

It is another object of the current invention to disclose a maneuverable RF coil assembly (MRCA), useful for being maneuvered at both positions: (i) over at least a portion of a neonate immobilized within a cradle at time of MR imaging; and (ii) below or aside the cradle when it is not required for imaging, comprising at least one RF coil and maneuvering mechanism; wherein the maneuvering mechanism comprises both: (i) a linear reciprocating mechanism for approaching or otherwise drawing away at least one coil to and from the neonate; and (ii) tilting mechanism for placing at least one coil away from the neonate; further wherein the maneuvering mechanism is selected from a group consisting of: automated, manual, semi-automated, remote controlled, and any combination thereof; further wherein the RF coil assembly comprises at least one sensor configured to sense a selected from a group consisting of: structural integrity of the RF coil, structural integrity of the maneuvering mechanism, position of RF coil, proximity of the neonate to the RF coil, RF signal received, RF signal transmitted, and any combination thereof, and relay the sensed information as a signal configured to operate at least the maneuvering mechanism.

It is another object of the current invention to disclose a maneuverable RF coil assembly (MRCA), useful for being maneuvered at both positions: (i) over at least a portion of a neonate immobilized within a cradle at time of MR imaging; and (ii) below or aside the cradle when it is not required for imaging, comprising at least one RF coil and maneuvering mechanism; wherein the maneuvering mechanism comprises both: (i) a linear reciprocating mechanism for approaching or otherwise drawing away at least one coil to and from the neonate; and (ii) tilting mechanism for placing at least one coil away from the neonate; further wherein the maneuvering mechanism is selected from a group consisting of: automated, manual, semi-automated, remote controlled, and any combination thereof.

It is another object of the current invention to disclose a maneuverable RF coil assembly (MRCA), useful for being maneuvered at both positions: (i) over at least a portion of a neonate immobilized within a cradle at time of MR imaging; and (ii) below or aside the cradle when it is not required for imaging, comprising at least one RF coil and maneuvering mechanism; wherein the maneuvering mechanism comprises both: (i) a linear reciprocating mechanism for approaching or otherwise drawing away at least one coil to and from the neonate; and (ii) tilting mechanism for placing at least one coil away from the neonate, further wherein the RF coil assembly is reversibly detachable from the cradle.

It is another object of the current invention to disclose a maneuverable RF coil assembly (MRCA), useful for being maneuvered at both positions: (i) over at least a portion of a neonate immobilized within a cradle at time of MR imaging; and (ii) below or aside the cradle when it is not required for imaging, comprising at least one RF coil and maneuvering mechanism; wherein the maneuvering mechanism comprises both: (i) a linear reciprocating mechanism for approaching or otherwise drawing away at least one coil to and from the neonate; and (ii) tilting mechanism for placing at least one coil away from the neonate; further wherein the RF coil assembly comprises at least one sensor configured to sense a selected from a group consisting of: structural integrity of the RF coil, structural integrity of the maneuvering mechanism, position of RF coil, proximity of the neonate to the RF coil, RF signal received, RF signal transmitted, and any combination thereof; further wherein the sensor is configured to relay the sensed information as a signal configured to operate a selected from a group consisting of: at least one indicator, a CPU, a user interface, a monitor, a lighting system, an engine, an MRD operating system, the maneuvering mechanism, and any combination thereof.

It is another object of the current invention to disclose a maneuverable RF coil assembly (MRCA), useful for being maneuvered at both positions: (i) over at least a portion of a neonate immobilized within a cradle at time of MR imaging; and (ii) below or aside the cradle when it is not required for imaging, comprising at least one RF coil and maneuvering mechanism; wherein the maneuvering mechanism comprises both: (i) a linear reciprocating mechanism for approaching or otherwise drawing away at least one coil to and from the neonate; and (ii) tilting mechanism for placing at least one coil away from the neonate; further wherein the RF coil assembly comprises a plurality of RF coils; further wherein the RF coil is configured to connect to at least a second RF coil; and, further wherein the RF coil is connected to at least a second RF coil by a maneuverable connection.

It is another object of the current invention to disclose a maneuverable RF coil assembly (MRCA), useful for being maneuvered at both positions: (i) over at least a portion of a neonate immobilized within a cradle at time of MR imaging; and (ii) below or aside the cradle when it is not required for imaging, comprising at least one RF coil and maneuvering mechanism; wherein the maneuvering mechanism comprises both: (i) a linear reciprocating mechanism for approaching or otherwise drawing away at least one coil to and from the neonate; and (ii) tilting mechanism for placing at least one coil away from the neonate; further wherein the RF coil assembly comprises a plurality of RF coils; and, further wherein further the RF coil assembly, in connection with the cradle and supported by an MRI safe cart, is configured to be at least partially insertable into an MRD bore.

It is another object of the current invention to disclose a maneuverable RF coil assembly (MRCA), useful for being maneuvered at both positions: (i) over at least a portion of a neonate immobilized within a cradle at time of MR imaging; and (ii) below or aside the cradle when it is not required for imaging, comprising at least one RF coil and maneuvering mechanism; wherein the maneuvering mechanism comprises both: (i) a linear reciprocating mechanism for approaching or otherwise drawing away at least one coil to and from the neonate; and (ii) tilting mechanism for placing at least one coil away from the neonate; further wherein the cradle is supported by a MRI safe cart, at least a portion thereof is insertable into a selected from a group consisting of: an MRD bore, a transport device, a treatment device, a storage device and any combination thereof.

It is another object of the current invention to disclose a maneuverable RF coil assembly (MRCA), useful for being maneuvered at both positions: (i) over at least a portion of a neonate immobilized within a cradle at time of MR imaging; and (ii) below or aside the cradle when it is not required for imaging, comprising at least one RF coil and maneuvering mechanism; wherein the maneuvering mechanism comprises both: (i) a linear reciprocating mechanism for approaching or otherwise drawing away at least one coil to and from the neonate; and (ii) tilting mechanism for placing at least one coil away from the neonate; further wherein the maneuvering mechanism is configured to provide a plurality of positions for the RF coil adjacent to the neonate, when placed at the position of over at least a portion of a neonate further wherein the RF coil is configured to close an opening of an incubator when in at least one position; and, further wherein the cradle is supported by a MRI safe cart, at least a portion thereof is insertable into a selected from a group consisting of: an MRD bore, a transport device, a treatment device, a storage device and any combination thereof.

It is another object of the current invention to disclose a maneuverable RF coil assembly (MRCA), useful for being maneuvered to at least both positions: (i) over at least a portion of a neonate immobilized within a cradle at time of MR imaging; and (ii) below or aside the cradle when it is not required for imaging, comprising at least one RF coil and maneuvering mechanism; wherein the maneuvering mechanism comprises both: (i) a linear reciprocating mechanism for approaching or otherwise drawing away at least one coil to and from the neonate; and (ii) tilting mechanism for placing at least one coil away from the neonate; further wherein the RF assembly and cradle are sized and shaped to be at least partially accommodated within an MRD bore.

It is another object of the current invention to disclose a maneuverable RF coil assembly (MRCA), useful for being maneuvered to at least both positions: (i) over at least a portion of a neonate immobilized within a cradle at time of MR imaging; and (ii) below or aside the cradle when it is not required for imaging, comprising at least one RF coil and maneuvering mechanism; wherein the maneuvering mechanism comprises both: (i) a linear reciprocating mechanism for approaching or otherwise drawing away at least one coil to and from the neonate; and (ii) tilting mechanism for placing at least one coil away from the neonate; further wherein the RF assembly and cradle are sized and shaped to be at least partially accommodated within an MRD bore; and, further wherein the RF coil is configured to close an opening of an incubator when in at least one position.

It is another object of the current invention to disclose a maneuverable RF coil assembly (MRCA), useful for being maneuvered to at least both positions: (i) over at least a portion of a neonate immobilized within a cradle at time of MR imaging; and (ii) below or aside the cradle when it is not required for imaging, comprising at least one RF coil and maneuvering mechanism; wherein the maneuvering mechanism comprises both: (i) a linear reciprocating mechanism for approaching or otherwise drawing away at least one coil to and from the neonate; and (ii) tilting mechanism for placing at least one coil away from the neonate; further wherein the RF assembly and cradle are sized and shaped to be at least partially accommodated within an MRD bore; further wherein the RF coil maneuvering mechanism is configured to enable a plurality of consecutively maneuverable movement vectors.

It is another object of the current invention to disclose a maneuverable RF coil assembly (MRCA), useful for being maneuvered at both positions: (i) over at least a portion of a neonate immobilized within a cradle at time of MR imaging; and (ii) below or aside the cradle when it is not required for imaging, comprising at least one RF coil and maneuvering mechanism; wherein the maneuvering mechanism comprises both: (i) a linear reciprocating mechanism for approaching or otherwise drawing away at least one coil to and from the neonate; and (ii) tilting mechanism for placing at least one coil away from the neonate; further wherein the RF coil is selected from a group consisting of: solenoid, planar, volume, surface, quadrature, and any combination thereof.

It is another object of the current invention to disclose a maneuverable RF coil assembly (MRCA), useful for being maneuvered at both positions: (i) over at least a portion of a neonate immobilized within a cradle at time of MR imaging; and (ii) below or aside the cradle when it is not required for imaging, comprising at least one RF coil and maneuvering mechanism; wherein the maneuvering mechanism comprises both: (i) a linear reciprocating mechanism for approaching or otherwise drawing away at least one coil to and from the neonate; and (ii) tilting mechanism for placing at least one coil away from the neonate; further wherein the RF coil is a multi-tuned RF coil.

It is another object of the current invention to disclose a maneuverable RF coil assembly (MRCA), useful for being maneuvered at both positions: (i) over at least a portion of a neonate immobilized within a cradle at time of MR imaging; and (ii) below or aside the cradle when it is not required for imaging, comprising at least one RF coil and maneuvering mechanism; wherein the maneuvering mechanism comprises both: (i) a linear reciprocating mechanism for approaching or otherwise drawing away at least one coil to and from the neonate; and (ii) tilting mechanism for placing at least one coil away from the neonate; further wherein the RF coil assembly comprises a multi-channel RF coil; further wherein the RF coil assembly is reconfigurable between pluralities of operational modes.

It is another object of the current invention to disclose a maneuverable RF coil assembly (MRCA), useful for being maneuvered at both positions: (i) over at least a portion of a neonate immobilized within a cradle at time of MR imaging; and (ii) below or aside the cradle when it is not required for imaging, comprising at least one RF coil and maneuvering mechanism; wherein the maneuvering mechanism comprises both: (i) a linear reciprocating mechanism for approaching or otherwise drawing away at least one coil to and from the neonate; and (ii) tilting mechanism for placing at least one coil away from the neonate; further wherein the RF coil assembly comprises a multi-channel RF coil; further wherein the RF coil assembly is reconfigurable between pluralities of operational modes; further wherein the RF assembly and cradle are sized and shaped to be at least partially accommodated within an MRD bore.

It is another object of the current invention to disclose a multi-functional maneuvering mechanism (MMM) for maneuvering an RF coil assembly to and from at least two positions: (i) over at least a portion of a neonate immobilized within a cradle at time of MR imaging; and (ii) below or aside the cradle when it is not required for imaging, comprising at least one RF coil and maneuvering mechanism; wherein the multi-functional maneuvering mechanism comprises (i) at least one first linear reciprocating mechanism for approaching or otherwise drawing away at least one coil to and from the neonate; and (ii) at least one second tilting mechanism for placing at least one coil away from the neonate; further wherein the RF coil maneuvering mechanism is configured to enable a plurality of consecutively maneuverable movement vectors.

It is another object of the current invention to disclose a multi-functional maneuvering mechanism (MMM) for maneuvering an RF coil assembly to and from at least two positions: (i) over at least a portion of a neonate immobilized within a cradle at time of MR imaging; and (ii) below or aside the cradle when it is not required for imaging, comprising at least one RF coil and maneuvering mechanism; wherein the multi-functional maneuvering mechanism comprises (i) at least one first linear reciprocating mechanism for approaching or otherwise drawing away at least one coil to and from the neonate; and (ii) at least one second tilting mechanism for placing at least one coil away from the neonate; further wherein the maneuvering mechanism is configured to provide a plurality of positions for the RF coil adjacent to the neonate, when placed at the position of over at least a portion of a neonate.

It is another object of the current invention to disclose a multi-functional maneuvering mechanism (MMM) for maneuvering an RF coil assembly to and from at least two positions: (i) over at least a portion of a neonate immobilized within a cradle at time of MR imaging; and (ii) below or aside the cradle when it is not required for imaging, comprising at least one RF coil and maneuvering mechanism; wherein the multi-functional maneuvering mechanism comprises (i) at least one first linear reciprocating mechanism for approaching or otherwise drawing away at least one coil to and from the neonate; and (ii) at least one second tilting mechanism for placing at least one coil away from the neonate; further wherein the RF coil is configured to close an opening of an incubator when in at least one position.

It is another object of the current invention to disclose a multi-functional maneuvering mechanism (MMM) for maneuvering an RF coil assembly to and from at least two positions: (i) over at least a portion of a neonate immobilized within a cradle at time of MR imaging; and (ii) below or aside the cradle when it is not required for imaging, comprising at least one RF coil and maneuvering mechanism; wherein the multi-functional maneuvering mechanism comprises (i) at least one first linear reciprocating mechanism for approaching or otherwise drawing away at least one coil to and from the neonate; and (ii) at least one second tilting mechanism for placing at least one coil away from the neonate; further wherein the maneuvering mechanism is configured to provide a plurality of positions for the RF coil adjacent to the neonate, when placed at the position of over at least a portion of a neonate; and further wherein the RF coil is configured to close an opening of an incubator when in at least one position.

It is another object of the current invention to disclose a multi-functional maneuvering mechanism (MMM) for maneuvering an RF coil assembly to and from at least two positions: (i) over at least a portion of a neonate immobilized within a cradle at time of MR imaging; and (ii) below or aside the cradle when it is not required for imaging, comprising at least one RF coil and maneuvering mechanism; wherein the multi-functional maneuvering mechanism comprises (i) at least one first linear reciprocating mechanism for approaching or otherwise drawing away at least one coil to and from the neonate; and (ii) at least one second tilting mechanism for placing at least one coil away from the neonate; further wherein the assembly comprises a handle configured for maneuvering the RF coil assembly by a handler.

It is another object of the current invention to disclose a multi-functional maneuvering mechanism (MMM) for maneuvering an RF coil assembly to and from at least two positions: (i) over at least a portion of a neonate immobilized within a cradle at time of MR imaging; and (ii) below or aside the cradle when it is not required for imaging, comprising at least one RF coil and maneuvering mechanism; wherein the multi-functional maneuvering mechanism comprises (i) at least one first linear reciprocating mechanism for approaching or otherwise drawing away at least one coil to and from the neonate; and (ii) at least one second tilting mechanism for placing at least one coil away from the neonate; further wherein the maneuvering mechanism is selected from a group consisting of: automated, manual, semi-automated, remote controlled, and any combination thereof; further wherein the RF coil assembly comprises at least one sensor configured to sense a selected from a group consisting of: structural integrity of the RF coil, structural integrity of the maneuvering mechanism, position of RF coil, proximity of the neonate to the RF coil, RF signal received, RF signal transmitted, and any combination thereof, and relay the sensed information as a signal operating at least the maneuvering mechanism.

It is another object of the current invention to disclose a multi-functional maneuvering mechanism (MMM) for maneuvering an RF coil assembly to and from at least two positions: (i) over at least a portion of a neonate immobilized within a cradle at time of MR imaging; and (ii) below or aside the cradle when it is not required for imaging, comprising at least one RF coil and maneuvering mechanism; wherein the multi-functional maneuvering mechanism comprises (i) at least one first linear reciprocating mechanism for approaching or otherwise drawing away at least one coil to and from the neonate; and (ii) at least one second tilting mechanism for placing at least one coil away from the neonate; further wherein the maneuvering mechanism is selected from a group consisting of: automated, manual, semi-automated, remote controlled, and any combination thereof.

It is another object of the current invention to disclose a multi-functional maneuvering mechanism (MMM) for maneuvering an RF coil assembly to and from at least two positions: (i) over at least a portion of a neonate immobilized within a cradle at time of MR imaging; and (ii) below or aside the cradle when it is not required for imaging, comprising at least one RF coil and maneuvering mechanism; wherein the multi-functional maneuvering mechanism comprises (i) at least one first linear reciprocating mechanism for approaching or otherwise drawing away at least one coil to and from the neonate; and (ii) at least one second tilting mechanism for placing at least one coil away from the neonate; further wherein the RF coil assembly is reversibly detachable from the cradle.

It is another object of the current invention to disclose a multi-functional maneuvering mechanism (MMM) for maneuvering an RF coil assembly to and from at least two positions: (i) over at least a portion of a neonate immobilized within a cradle at time of MR imaging; and (ii) below or aside the cradle when it is not required for imaging, comprising at least one RF coil and maneuvering mechanism; wherein the multi-functional maneuvering mechanism comprises (i) at least one first linear reciprocating mechanism for approaching or otherwise drawing away at least one coil to and from the neonate; and (ii) at least one second tilting mechanism for placing at least one coil away from the neonate; further wherein the RF coil assembly comprises at least one sensor configured to sense a selected from a group consisting of: structural integrity of the RF coil, structural integrity of the maneuvering mechanism, position of RF coil, proximity of the neonate to the RF coil, RF signal received, RF signal transmitted, and any combination thereof; further wherein the sensor is configured to relay the sensed information as a signal operating a selected from a group consisting of: at least one indicator, a CPU, a user interface, a monitor, a lighting system, an engine, an MRD operating system, the maneuvering mechanism, and any combination thereof.

It is another object of the current invention to disclose a multi-functional maneuvering mechanism (MMM) for maneuvering an RF coil assembly to and from at least two positions: (i) over at least a portion of a neonate immobilized within a cradle at time of MR imaging; and (ii) below or aside the cradle when it is not required for imaging, comprising at least one RF coil and maneuvering mechanism; wherein the multi-functional maneuvering mechanism comprises (i) at least one first linear reciprocating mechanism for approaching or otherwise drawing away at least one coil to and from the neonate; and (ii) at least one second tilting mechanism for placing at least one coil away from the neonate; further wherein the RF coil assembly comprises a plurality of RF coils; further wherein the RF coil is configured to connect to at least a second RF coil; and, further wherein the RF coil is connected to at least a second RF coil by a maneuverable connection.

It is another object of the current invention to disclose a multi-functional maneuvering mechanism (MMM) for maneuvering an RF coil assembly to and from at least two positions: (i) over at least a portion of a neonate immobilized within a cradle at time of MR imaging; and (ii) below or aside the cradle when it is not required for imaging, comprising at least one RF coil and maneuvering mechanism; wherein the multi-functional maneuvering mechanism comprises (i) at least one first linear reciprocating mechanism for approaching or otherwise drawing away at least one coil to and from the neonate; and (ii) at least one second tilting mechanism for placing at least one coil away from the neonate; further wherein the RF coil assembly comprises a plurality of RF coils; and, further wherein further the RF coil assembly, in connection with the cradle and supported by an MRI safe cart, is configured to be at least partially insertable into an MRD bore.

It is another object of the current invention to disclose a multi-functional maneuvering mechanism (MMM) for maneuvering an RF coil assembly to and from at least two positions: (i) over at least a portion of a neonate immobilized within a cradle at time of MR imaging; and (ii) below or aside the cradle when it is not required for imaging, comprising at least one RF coil and maneuvering mechanism; wherein the multi-functional maneuvering mechanism comprises (i) at least one first linear reciprocating mechanism for approaching or otherwise drawing away at least one coil to and from the neonate; and (ii) at least one second tilting mechanism for placing at least one coil away from the neonate; further wherein the cradle is supported by a MRI safe cart, at least a portion thereof is insertable into a selected from a group consisting of: an MRD bore, a transport device, a treatment device, a storage device and any combination thereof.

It is another object of the current invention to disclose a multi-functional maneuvering mechanism (MMM) for maneuvering an RF coil assembly to and from at least two positions: (i) over at least a portion of a neonate immobilized within a cradle at time of MR imaging; and (ii) below or aside the cradle when it is not required for imaging, comprising at least one RF coil and maneuvering mechanism; wherein the multi-functional maneuvering mechanism comprises (i) at least one first linear reciprocating mechanism for approaching or otherwise drawing away at least one coil to and from the neonate; and (ii) at least one second tilting mechanism for placing at least one coil away from the neonate; further wherein the maneuvering mechanism is configured to provide a plurality of positions for the RF coil adjacent to the neonate, when placed at the position of over at least a portion of a neonate further wherein the RF coil is configured to close an opening of an incubator when in at least one position; and, further wherein the cradle is supported by a MRI safe cart, at least a portion thereof is insertable into a selected from a group consisting of: an MRD bore, a transport device, a treatment device, a storage device and any combination thereof.

It is another object of the current invention to disclose a multi-functional maneuvering mechanism (MMM) for maneuvering an RF coil assembly to and from at least two positions: (i) over at least a portion of a neonate immobilized within a cradle at time of MR imaging; and (ii) below or aside the cradle when it is not required for imaging, comprising at least one RF coil and maneuvering mechanism; wherein the multi-functional maneuvering mechanism comprises (i) at least one first linear reciprocating mechanism for approaching or otherwise drawing away at least one coil to and from the neonate; and (ii) at least one second tilting mechanism for placing at least one coil away from the neonate; further wherein the RF assembly and cradle are sized and shaped to be at least partially accommodated within an MRD bore.

It is another object of the current invention to disclose a multi-functional maneuvering mechanism (MMM) for maneuvering an RF coil assembly to and from at least two positions: (i) over at least a portion of a neonate immobilized within a cradle at time of MR imaging; and (ii) below or aside the cradle when it is not required for imaging, comprising at least one RF coil and maneuvering mechanism; wherein the multi-functional maneuvering mechanism comprises (i) at least one first linear reciprocating mechanism for approaching or otherwise drawing away at least one coil to and from the neonate; and (ii) at least one second tilting mechanism for placing at least one coil away from the neonate; further wherein the RF assembly and cradle are sized and shaped to be at least partially accommodated within an MRD bore; and, further wherein the RF coil is configured to close an opening of an incubator when in at least one position.

It is another object of the current invention to disclose a multi-functional maneuvering mechanism (MMM) for maneuvering an RF coil assembly to and from at least two positions: (i) over at least a portion of a neonate immobilized within a cradle at time of MR imaging; and (ii) below or aside the cradle when it is not required for imaging, comprising at least one RF coil and maneuvering mechanism; wherein the multi-functional maneuvering mechanism comprises (i) at least one first linear reciprocating mechanism for approaching or otherwise drawing away at least one coil to and from the neonate; and (ii) at least one second tilting mechanism for placing at least one coil away from the neonate; further wherein the RF assembly and cradle are sized and shaped to be at least partially accommodated within an MRD bore; further wherein the RF coil maneuvering mechanism is configured to enable a plurality of consecutively maneuverable movement vectors.

It is another object of the current invention to disclose a multi-functional maneuvering mechanism (MMM) for maneuvering an RF coil assembly to and from at least two positions: (i) over at least a portion of a neonate immobilized within a cradle at time of MR imaging; and (ii) below or aside the cradle when it is not required for imaging, comprising at least one RF coil and maneuvering mechanism; wherein the multi-functional maneuvering mechanism comprises (i) at least one first linear reciprocating mechanism for approaching or otherwise drawing away at least one coil to and from the neonate; and (ii) at least one second tilting mechanism for placing at least one coil away from the neonate; further wherein the RF coil is selected from a group consisting of: solenoid, planar, volume, surface, quadrature, and any combination thereof.

It is another object of the current invention to disclose a multi-functional maneuvering mechanism (MMM) for maneuvering an RF coil assembly to and from at least two positions: (i) over at least a portion of a neonate immobilized within a cradle at time of MR imaging; and (ii) below or aside the cradle when it is not required for imaging, comprising at least one RF coil and maneuvering mechanism; wherein the multi-functional maneuvering mechanism comprises (i) at least one first linear reciprocating mechanism for approaching or otherwise drawing away at least one coil to and from the neonate; and (ii) at least one second tilting mechanism for placing at least one coil away from the neonate; further wherein the RF coil is a multi-tuned RF coil.

It is another object of the current invention to disclose a multi-functional maneuvering mechanism (MMM) for maneuvering an RF coil assembly to and from at least two positions: (i) over at least a portion of a neonate immobilized within a cradle at time of MR imaging; and (ii) below or aside the cradle when it is not required for imaging, comprising at least one RF coil and maneuvering mechanism; wherein the multi-functional maneuvering mechanism comprises (i) at least one first linear reciprocating mechanism for approaching or otherwise drawing away at least one coil to and from the neonate; and (ii) at least one second tilting mechanism for placing at least one coil away from the neonate; further wherein the RF coil assembly comprises a multi-channel RF coil; further wherein the RF coil assembly is reconfigurable between pluralities of operational modes.

It is another object of the current invention to disclose a multi-functional maneuvering mechanism (MMM) for maneuvering an RF coil assembly to and from at least two positions: (i) over at least a portion of a neonate immobilized within a cradle at time of MR imaging; and (ii) below or aside the cradle when it is not required for imaging, comprising at least one RF coil and maneuvering mechanism; wherein the multi-functional maneuvering mechanism comprises (i) at least one first linear reciprocating mechanism for approaching or otherwise drawing away at least one coil to and from the neonate; and (ii) at least one second tilting mechanism for placing at least one coil away from the neonate; further wherein the RF coil assembly comprises a multi-channel RF coil; further wherein the RF coil assembly is reconfigurable between pluralities of operational modes; further wherein the RF assembly and cradle are sized and shaped to be at least partially accommodated within an MRD bore.

It is another object of the current invention to disclose a multi-functional maneuvering mechanism (MMM) for maneuvering an RF coil assembly to and from at least two positions: (i) over at least a portion of a neonate immobilized within a cradle at time of MR imaging; and (ii) below or aside the cradle when it is not required for imaging, comprising at least one RF coil and maneuvering mechanism; wherein the multi-functional maneuvering mechanism comprises (i) at least one first linear reciprocating mechanism for approaching or otherwise drawing away at least one coil to and from the neonate; and (ii) at least one second tilting mechanism for placing at least one coil away from the neonate; further wherein the cradle comprises an envelope surrounding an internal environment in which the neonate is accommodated; further wherein the maneuverable mechanism is configured to allow movement of the RF coil assembly within the internal environment, external to the internal environment or both.

It is another object of the current invention to disclose a multi-functional maneuvering mechanism (MMM) for maneuvering an RF coil assembly to and from at least two positions: (i) over at least a portion of a neonate immobilized within a cradle at time of MR imaging; and (ii) below or aside the cradle when it is not required for imaging, comprising at least one RF coil and maneuvering mechanism; wherein the multi-functional maneuvering mechanism comprises (i) at least one first linear reciprocating mechanism for approaching or otherwise drawing away at least one coil to and from the neonate; and (ii) at least one second tilting mechanism for placing at least one coil away from the neonate; further wherein the cradle comprises an envelope surrounding an internal environment in which the neonate is accommodated; further wherein the maneuverable mechanism is configured to allow movement of the RF coil assembly within the internal environment, external to the internal environment or both; further wherein the RF coil maneuvering mechanism is configured to enable a plurality of consecutively maneuverable movement vectors.

It is another object of the current invention to disclose a multi-functional maneuvering mechanism (MMM) for maneuvering at least two RF coil assemblies to and from at least two positions: (i) at least one first RF coil assembly over at least a portion of a neonate immobilized within a cradle at time of MR imaging, at least one second RF coil assembly below or alongside the neonate within the cradle or external to the cradle; and (ii) aside the neonate or cradle when it is not required for imaging, comprising at least one RF coil and maneuvering mechanism; wherein the multi-functional maneuvering mechanism comprises (i) at least one first linear reciprocating mechanism for approaching or otherwise drawing away at least one coil to and from the neonate; and (ii) at least one second tilting mechanism for placing at least one coil away from the neonate.

BRIEF DESCRIPTION OF THE FIGURES

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The present invention may be practiced according to the claims without some or all of these specific details. For the purpose of clarity, technical material that is known in the technical fields related to the invention has not been described in detail so that the present invention is not unnecessarily obscured. In the accompanying drawing:

FIG. 2A is a schematic illustration of an installable RF coil in a perspective view;

FIG. 2B is a schematic illustration of an RF coil, in an upright position, in a back view, inserted between two tracks of a cradle;

FIG. 2C is a schematic illustration of an RF coil, in an upside down position, in a back view, inserted between two tracks of a cradle;

DETAILED DESCRIPTION OF THE PREFERRED EMBODIMENTS

Figure 1:
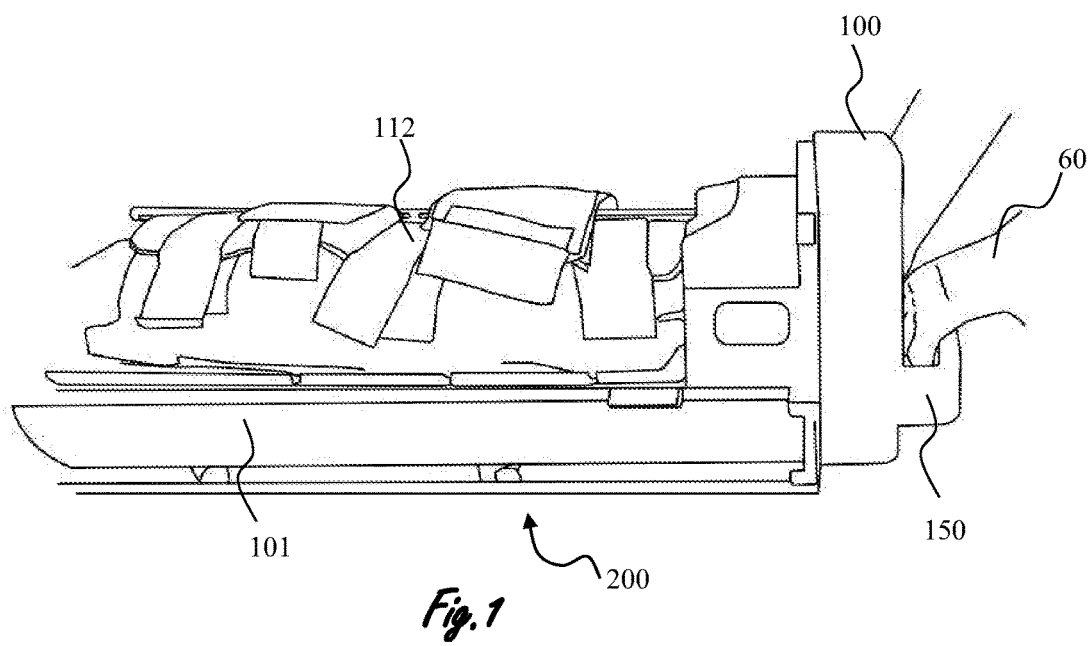
FIG. 1 is a schematic illustration of an installable RF coil connected to a cradle.

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The present invention may be practiced according to the claims without some or all of these specific details. For the purpose of clarity, technical material that is known in the technical fields related to the invention has not been described in detail so that the present invention is not unnecessarily obscured.

The essence of the present invention is to provide a maneuverable RF coil assembly, useful for magnetic resonance imaging of a neonate, and/or a multi-functional maneuvering mechanism for maneuvering an RF coil. The maneuverable RF coil assembly is maneverable at both positions: (i) over a neonate immobilized within a cradle at time of MR imaging; and (ii) below or aside the cradle when it is not required for imaging, comprising at least one RF coil and maneuvering mechanism; the maneuvering mechanism comprises both: (i) a linear reciprocating mechanism for approaching or otherwise drawing away at least one coil to and from the neonate; and (ii) tilting mechanism for placing at least one coil away from the neonate, and methods thereof.

Further the present invention provides an MRI system, an MRI compatible cart, and a cradle, each in connection with a maneuverable RF coil assembly and/or a multi-functional maneuvering mechanism for maneuvering an RF coil.

The maneuverable RF coil of the present invention will increase the safety of MRI as the patient will be connected to medical equipment whilst being imaged, without having to be disconnected or handled for better imaging. The current invention will increase the efficiency of magnetic resonance imaging as RF coils proximal to the patient/neonate increase the quality of the images obtained, with minimum interference to the patient, having maximal access to the patient when not imaged.

The term "about" refers hereinafter to 20% more or less than the defied value.

The term 'magnetic resonance imaging device' (MRD), specifically applies hereinafter to any Magnetic Resonance Imaging (MRI) device, any Nuclear Magnetic Resonance (NMR) spectroscope, any Electron Spin Resonance (ESR) spectroscope, any Nuclear Quadruple Resonance (NQR) or any combination thereof. The term, in this invention, also applies to any other analyzing and imaging instruments comprising a volume of interest, such as computerized tomography (CT), ultrasound (US) etc. The MRD hereby disclosed is optionally a portable MRI device, such as the ASPECT-MR Ltd commercially available devices, or a commercially available non-portable device. Additionally or alternatively, the MRD is self-fastening cage surrounding a magnetic resonance device as depicted in U.S. Pat. No. 7,719,279 B2, filed 27 May 2008 titled: "SELF-FASTENING CAGE SURROUNDING A MAGNETIC RESONANCE DEVICE AND METHODS THEREOF", of which is hereby incorporated by reference in its entirety.

The term "plurality" interchangeably refers hereinafter to an integer a, when a>1.

The term "external environment" refers hereinafter to the external space outside of an MRI scanner.

The term "neonate" interchangeably refers herein after to a term selected from: patient, baby, infant, toddler, child, adolescent, adult, elderly, etc.; further this term refers to person or animal, a whole entity or a portion thereof.

The term "neonate's body part" interchangeably refers herein after to any term representing a mammal body part such as: head, neck, chest area, back, backside, buttock, leg, feet, hand, arm, abdomen, shoulders, finger, pelvic, joint, knees, elbows, wrist, ankle, and any combination thereof.

The term "coil" interchangeably refers herein after to an element constructed of at least a single loop of an electrical conductive material (such as metallic wires or tubes) designed either to produce a magnetic field from current flowing through the wire, or detect a changing magnetic field by voltage induced in the wire.

The term "RF" or "radio frequency" interchangeably refers herein after to any frequency within the electromagnetic spectrum associated with radio wave propagation. The RF usually used in magnetic resonance study is in the megahertz (MHz) range. The RF range commonly used in electron spin resonance is in the gigahertz (GHz).

The term "RF coil" interchangeably refers herein after to any coil used for transmitting RF pulses and/or receiving MR signals used for magnetic resonance imaging. RF coils are known in the art to be used in magnetic resonance configurations such as "birdcage coil", "saddle coil", "solenoid coil", and the like.

The term "signal to noise ratio" or "SNR" interchangeably refers herein after to any description of the relative contribution to a detected signal originating from the true sought-after signal and random superimposed signals referred to as noise. To improve an image, hence to increase the signal to noise ratio, one can average several measurements of the signal, in expectance that the noise will be cancelled out. For this homogeneity of conditions such as temperature, neonate body posture and movement, magnetic and RF interruptions from the outside, and etc., is important between each scan. Other parameters that can improve the SNR are sampling larger volumes, increasing the strength of the magnetic field or implementing surface coils.

The term "surface coil" interchangeably refers herein after to any coil that does not surround the body, and is placed close to the surface of the body, used to restrict the region of the body contributing to the detected signal. This can improve the signal to noise ratio in areas close to the coil. A "magnetic resonance surface coil" interchangeably refers herein after to any surface coil that provides an effective selectivity for a defined area around the coil. A gradient surface coil can add a spatial selectivity.

The term "solenoid coil" interchangeably refers herein after to any coil that comprises helical winding (as in a long wind cylinder) of current-carrying wire that produces a magnetic field along the axis of the helix. The magnetic field within the coil in this configuration is known in the art to be relatively uniform.

The term "planar coils" interchangeably refers herein after to any RF coil that is used for vertical field magnetic resonance imaging.

The term "volume coil" interchangeably refers herein after to any coil that surrounds a portion of the body. The volume coil can be for example birdcage coils, TEM coils, and saddle coils.

The term "quadrature coil" interchangeably refers herein after to any coil that produces an RF field with circular polarization by providing RF feed points that are out of phase by 90 degrees. It is known in the art that when used as a receiver an increase in SNR can be achieved.

The term "multiply tuned coil" interchangeably refers herein after to any RF coil designed to operate at more than one resonance frequency (providing different operational modes), so that the MR of more than one kind of nucleus can be observed with the same coil.

The term "multi-channel RF coil" interchangeably refers herein after to any RF coil assembly designed to operate at more than one channel. Further this type is in connection with a multi-channel transceiver. The multi-channel RF coils are in an especially configured array. This type of RF array coil is composed of multiple surface coils which are overlapped in such a way that the mutual coupling is minimal. Typically used for "parallel imaging" to collect simultaneously different portions of the image in physical space or different data point that can be integrated to generate a picture. Parallel imaging speeds up imaging and can be configured to various coils and sensitivities. Parallel imaging can also be used by a multiple coils assembly to collect simultaneously different portions of the image in physical space, or different data points for the same space, which are later used for reconstructing the image.

The term "shim coils" interchangeably refers herein after to any RF coil, carrying a relatively small current, that provide auxiliary magnetic fields in order to compensate for in-homogeneities in the main magnetic field of the MRI machine.

The term "MRI-safe", interchangeably refers hereinafter to any device, part, element, component or implant that is completely non-magnetic, non-electrically conductive, and non-RF reactive, eliminating all of the primary potential threats during an MRI procedure.

The term "incubator" interchangeably refers hereinafter to a special unit specializing in the care of ill or premature newborn infants. This includes a stationary incubator, a moveable incubator, a transport incubator, a disposable incubator, a healthcare facility incubator, portable incubator, an intensive care incubator, an incubator intended for home use, an incubator for imaging a neonate, a treatment incubator, a modular incubator, an isolating incubator and any combination thereof. The neonatal incubator is a box-like enclosure in which an infant can be kept in a controlled environment for observation and care. The incubator usually includes observation means to the accommodated neonate, and openings for the passage of life support equipment, and the handler's hands. At least partially enclosed environment formed within the incubator is at least partially isolated from the external environment conditions such as noise, vibration, drift, temperature, light, gas concentrations, humidity, microorganisms, etc. This environment can be controlled by environment control systems such as temperature regulating, ventilating, humidifying, lighting, moving, noise reduction systems, vibration reducing systems, etc. An incubator is, in an embodiment, a deployable incubator as depicted in U.S. Provisional Patent Application 61/940,514, filed 17 Feb. 2014, titled "AN INCUBATOR DEPLOYABLE MULTI-FUNCTIONAL PANEL", of which is hereby incorporated by reference herein in its entirety. An incubator is, in an embodiment, a transport incubator as depicted in U.S. Provisional Patent Application 61/899,233, filed 3 Nov. 2013, titled "A PATIENT TRANSPORT INCUBATOR", of which is hereby incorporated by reference herein in its entirety.

The terms "cradle", "bed", "capsule", "tray", "upper tray", "countertop", "treatment table" and "incubator" will be interchangeably used herein after to define infant's support and intimate envelope.

The term "cart" interchangeably refers hereinafter to any transport device or any small vehicle pushed or pulled by manually, automatically or both. A cart usually comprises mobility providing elements such as one or a plurality of a wheel, roller, sliding blade, rotating belt, etc. Further, the cart can be such as rickshaw, ruck, wagon, barrow, buggy, dolly, carriage, float, cab, dray, gig, gurney, handcart, palanquin, pushcart, tumbrel, wheelbarrow, curricle, etc.

The term "tilting" or "tilt" interchangeably refers hereinafter to a motion such as rotating, moving around a pivot point, turning, swinging, leaning, bending, dipping, inclining, lurching, shifting, swaying, tipping, heeling, reclining, slopping, slouching, swaging, setting an angel, being lopsided, askew, off balance, bending, angling, slanting, twist, loop, tip, incurvate, deflect, verge, spiral, curl, arch, bow, swirl, or any combination of the above.

The term "hinge" interchangeably refers hereinafter to any maneuverable connection for rotational motion between the current invention parts, portions and modules, such as a flexible mechanism or material, joint, hook, thread, axis, juncture, fold, bend, elbow, knee, corner, fork, axis, pole, ball and socket, condyloid joint, mechanical device, fold hinge, joint, bearing, barrel hinge, pivot hinges, butt/mortise hinges, case hinges, continuous hinges, piano hinges, concealed hinges, cup hinge, euro hinge, butterfly hinges, parliament hinges, dovetail hinges, flag hinges, flag hinge, strap hinges, H hinges, HL hinges, counter-flap hinge, flush hinge, coach hinge, rising butt hinge, double action spring hinge, tee hinge, friction hinge, security hinge, cranked hinge, lift-off hinge, self-closing hinge, butt hinge, butler tray hinge, card table hinge, drop leaf table hinge, floating hinge, living hinge, and any combination thereof.

The term "pivot pin" interchangeably refers hereinafter to any maneuverable connection for rotational motion between the current invention parts, portions and modules at least partially around a pivot point.

The term "turning mechanism" interchangeably refers hereinafter to any maneuverable mechanism for a turning motion between the current invention parts, portions and modules around a fixed axis, such as a bearing, a faucet, a wheel, screwing motion, and etc.

The term "track" interchangeably refers hereinafter to such as a track, guide, path, groove, rail, line, route, duct, channel, passage, course, trail, lineament, lane, road, seam, length, axis, tract, pathway, course, highway, roadway, alley, artery, avenue, boulevard, clearing, cut, drag, thoroughfare, trajectory, walk, track way, belt, swath, glider, circuit, stretch, runway, caterpillar track, half-track, flat track, soft close track, pivoted sliding track, adjustable track, etc. Further this track maybe a physical or a virtual motion path along which a maneuverable portion is moved.

The term "sliding mechanism", interchangeably refers hereinafter to a mechanism in with a body is movable in a sliding motion along a track. A portion of the movable body is mounted on, suspended from, inserted to, threaded to, interweaved with, integrated to, fitted to, following, etc. a track. In reference to a physical track, the connection of the moveable portion to the track is directly by geometrical shape fit of on part with the other and/or via a third element such as wheels, rack wheels, ball bearings, rollers, rolling discs, lubricant, location guide, belts, pulleys etc. In reference to a virtual motion track, the movable portion is connected to a sliding motion providing mechanism such as telescopic arms, folding arms, arms, angled arms, etc. connected at a pivotal point, allowing for sliding movement along a predefined virtual path. In addition this sliding mechanism may enable straight sliding, curved sliding, folding slide, sliding around a corner, rolling door sliding, etc.

The term "automatic" in respect to the movement of a part, a portion and/or a module of the incubator, cart or MRD interchangeably refers herein after to a predefined movement having a start location and an end location. Further this movement could be derived from an engine, a self-sliding movement when a latching mechanism is released, pneumatic mechanism (compressed from the self-sliding movement), hydraulic cylinder, using a gear shift system, etc.

The term "manual" in respect to the movement of a part of the IRFA interchangeably refers herein after to any application of force by the handler aimed at moving at least a portion of the moving part. This force is generated by an action such as pushing, pulling, lifting, levering, turning, twisting, hitting, lowering, tilting, twisting, squeezing, touching, etc.

The term "sensor" interchangeably refers hereinafter to any device that receives a signal or stimulus (heat, pressure, light, motion, sound, humidity etc.) and responds to it in a distinctive manner. This manner can be such as inducing the action/inaction of other devices, inducing the action/inaction of indicators (visual, auditable or sensible), inducing the display of the input received by the sensor, inducing the data storage/analysis of input in a central processing unit, etc.

The term "indicator" interchangeably refers hereinafter to any device that conveys a signal or information to a person. The indicator can be audible, sensible, visual, and any combination thereof. The indicator can for example convey a signal in form of light, flashing light, flickering light, blinking light, change of spectrum of colors of light, sound in an audio frequency range of roughly 20 to 20,000 Hz, movement, position shifting, shaking, vibrating, quivering, and etc.

The term "life supporting equipment" interchangeably refers hereinafter to any element that provides an environmental condition, a medical condition or monitoring an environmental or medical condition thereof that assists in sustaining the life of a neonate or bettering their physical and physiological wellbeing. This element can be: (a) any medical equipment: all devices, tubes, connectors, wires, liquid carriers, needles, sensors, monitors, etc., that are used by medical personal in association with the patient. This equipment is such as bilirubin light, an IV (intravenous) pump, oxygen supplementation systems by head hood or nasal cannula, continuous positive airway pressure system, a feeding tube, an umbilical artery catheter, a fluid transport device, hemofiltration system, hemodialysis system, MRI contras solution injection, imaging the neonate, etc.; (b) medical measurement and observation systems (including sensors and/or monitors) of temperature, respiration, cardiac function, oxygenation, brain activity such as ECG (electrocardiography) monitor, blood pressure monitor, cardio-respiratory monitor, pulse oximeter; and (c) environmental control systems such as ventilator, air conditioner, humidifier, temperature regulator, climate control systems, noise muffling device, vibration muffling device, etc. and any combination thereof.

The term "medical equipment tubing" interchangeably refers hereinafter to all tubes, cables, connectors, wires, liquid carriers, gas carriers, electrical wires, monitoring cables, viewing cables, data cables, etc., that is used in connection to life support equipment, medical equipment or physical environment maintenance or monitoring.

The term "transparent material" interchangeably refers hereinafter to materials such as, poly-methyl methacrylate, thermoplastic polyurethane, polyethylene, polyethylene terephthalate, isophthalic acid modified polyethylene terephthalate, glycol modified polyethylene terephthalate, polypropylene, polystyrene, acrylic, polyacetate, cellulose acetate, polycarbonate, nylon, glass, polyvinyl chloride, etc. Further in some embodiments at least a portion of this material is imbedded with non-transparent materials for means of strength and/or conductivity such as metallic wires The term "connected" in reference to the current invention parts and modules, interchangeably refers hereinafter to any contact, relation, association, integration, interconnection, joining, inserting, sewing, welding, interweaving, placing, nesting, layering, etc., of the current invention parts and modules to each other and to a third party.

The term "emergency release mechanism", interchangeably refers hereinafter to a mechanism used in immediate need of extracting a neonate from the present invention assembly of installable RF coil and incubator.

The term "handler" interchangeably refers herein after to any person that is in contact with the present invention parts and modules such as medical personal, maintenance personal, parent, chaperon and technician.

The term "ergonomic" interchangeably refers hereinafter to the design of the present invention RFA and incubator to minimize discomfort of the neonate, handler or both.

The incubator is designed in a manner that fits the neonate's body and its cognitive needs and abilities. More specifically this term relates to the placement within the inner volume of the incubator to be fitting by means of size, shape, surface properties, sound transmission, light transmission, etc., to be appropriate for maximizing the well-being of the neonate. This term further relates to the human interface of the present invention designed for the handler, parts such as the user interface, open and close mechanisms, overall size and shape, handles, accessibility to the neonate, position maneuvering means, connections to other equipment, etc., are all designed in a manner that takes into consideration human factors.

The term "user interface" interchangeably refers hereinafter to at least one defined area in which the user (patient or handler) interacts with the cart, incubator or IRFA. This area harbors elements such as: passage for medical equipment, display, CPU, alarm system, monitoring system, power supply, open mechanism, close mechanism, visual indicators, auditory indicators, sensible indicators, handles, placements, etc. The user interface is designed for the handler, neonate or both.

The term "handle" interchangeably refers hereinafter to any element configured to be in contact with the handler in order to perform a task such as push, pull, open, twist, close, turn, tilt, press, move, slide, separate, unite, lock, squeeze, touch, lower, raise, and any combination thereof. This can be such as a knob, stem, arm, bail, crank, ear, grasp, haft, handgrip, helve, hilt, hold, holder, bar, stump, projection, hook, fin, flapper, grip, rod, wing, guide, brace, clamp, lever, counter lever, crossbar, The term "treatment device" interchangeably refers hereinafter to any device or assembly used for monitoring, operating, treating, transporting and/or imaging the patient, where a patient is placed in order to be treated, transported, monitored, imaged, and etc. This device can be such as an operating table, a mobile gurney, a stretcher, a treatment table, an imaging table (e.g. like in an x-ray room), a patient bed, and etc.

The term "restraining means" or "means for maintaining the position of the neonate" interchangeably refers hereinafter to any object designed and configured to hold the body position of the neonate, so as to restrict movement of the neonate. This can range from a substantially loose restraining mean limiting only the fall of the neonate from the apparatus or device he/she is connected to (e.g. the incubator, or any cart upper tray), to an almost completely restrictive mean providing complete immobilization of the neonate. Other options are various combinations of immobilizing at least one body part or limb of the neonate. It is important that these means are loose enough in their strictest form to enable breathing and blood flow of the patient neonate. The means are such as straps, immobilization suit, hugger, belt, restraint, flaps, cage, cushions and supports, ergonomic placement, concave shaped sponge like support, bars, and etc. Additionally or alternatively, these means are configured to have an open position in which a neonate can be inserted into, extracted from, or accessed fully, and a closed position immobilizing the patient. Additionally or alternatively these means can include a buckle, switch, snap, loop, latch, and any kind of an opening or closing mechanism.

According to one embodiment of the present invention a maneuverable RF coil assembly (MRCA), useful for being maneuvered at both positions: (i) over at least a portion of a neonate immobilized within a cradle at time of MR imaging; and (ii) below or aside the cradle when it is not required for imaging, comprising at least one RF coil and maneuvering mechanism; wherein the maneuvering mechanism comprises both: (i) a linear reciprocating mechanism for approaching or otherwise drawing away at least one coil to and from the neonate; and (ii) tilting mechanism for placing at least one coil away from the neonate.

According to another embodiment of the present invention, an MRCA as defined above is disclosed, wherein the assembly is sized and shaped to fit over at least a portion of the neonate.

According to another embodiment of the present invention, an MRCA as defined above is disclosed, wherein the assembly is sized and shaped to accommodate at least a portion of the neonate.

According to another embodiment of the present invention, an MRCA as defined above is disclosed, wherein the maneuvering mechanism is configured to provide a plurality of positions for the RF coil adjacent to the neonate.

According to another embodiment of the present invention, an MRCA as defined above is disclosed, wherein the RF coil maneuvering mechanism is configured to enable a plurality of consecutively maneuverable vectors.

According to another embodiment of the present invention, an MRCA as defined above is disclosed, wherein the cradle comprises an emergency release mechanism configured for immediate release of the neonate from the cradle.

According to another embodiment of the present invention, an MRCA as defined above is disclosed, wherein the RF coil comprises an emergency release mechanism configured for immediate release of the RF coil from the cradle.

According to another embodiment of the present invention, an MRCA as defined above is disclosed, wherein the cradle comprises life support equipment for the neonate.

According to another embodiment of the present invention, an MRCA as defined above is disclosed, wherein the cradle comprises means for maintaining the position of the neonate.

According to another embodiment of the present invention, an MRCA as defined above is disclosed, wherein the cradle comprises an envelope surrounding an internal environment in which the neonate is accommodated.

According to another embodiment of the present invention, an MRCA as defined above is disclosed, wherein the maneuverable mechanism is configured to allow movement of the RF coil assembly within the internal environment, external to the internal environment or both.

According to another embodiment of the present invention, an MRCA as defined above is disclosed, wherein the RF coil is configured to have at least one position forming a close environment incubator.

According to another embodiment of the present invention, an MRCA as defined above is disclosed, wherein the cradle is selected from a group consisting of: an incubator, a deployed incubator, a transport incubator, a treatment table, a countertop, an operating table, a bed, a baby cradle, a basket, a mattress, a stretcher, a gurney, and any combination thereof.

According to another embodiment of the present invention, an MRCA as defined above is disclosed, wherein the RF coil is configured to close an opening of an incubator when in at least one position.

According to another embodiment of the present invention, an MRCA as defined above is disclosed, wherein the cradle comprises a selected from a group consisting of: at least one sensor, at least one indicator, at least one medical equipment tubing placement, at least one opening fitted for the insertion of a handlers hand, at least one opening for the passage of life supporting equipment, and any combination thereof. Further, the sensor is connected to an indicator selected from a group consisting of: auditable, visual, sensual, and any combination thereof, and configured to transmit data thereto.

According to another embodiment of the present invention, an MRCA as defined above is disclosed, wherein the cradle comprises a user interface configured to monitor or control a selected from a group consisting of: life supporting equipment, MRI operation, position of RF coil, RF coil maneuvering mechanism, opening or closing the cradle, and any combination thereof.

According to another embodiment of the present invention, an MRCA as defined above is disclosed, wherein the RF coil assembly comprises at least one sensor configured to sense a selected from a group consisting of: structural integrity of the RF coil, structural integrity of the maneuvering mechanism, position of RF coil, proximity of the neonate to the coil, RF signal received, RF signal transmitted, and any combination thereof. Further, the sensor is connected to an indicator selected from a group consisting of: auditable, visual, sensual, and any combination thereof, and configured to transmit data thereto.

According to another embodiment of the present invention, an MRCA as defined above is disclosed, wherein the assembly comprises a handle configured for maneuvering the RF coil assembly by a handler.

According to another embodiment of the present invention, an MRCA as defined above is disclosed, wherein the maneuvering mechanism selected from a group consisting of: automated, manual, semi-automated, remote controlled, and any combination thereof.

According to another embodiment of the present invention, an MRCA as defined above is disclosed, wherein the maneuverable mechanism comprises means selected from a group consisting of: sliding mechanism, pivot point mechanism, hinge, telescopic mechanism, hydraulic mechanism, turning mechanism, and any combination thereof.

According to another embodiment of the present invention, an MRCA as defined above is disclosed, wherein at least a portion of the assembly and cradle are made of a material selected from a group consisting of: a MRI safe material, at least partially transparent material, a sterilizable material, a fire retardant material, and any combination thereof.

According to another embodiment of the present invention, an MRCA as defined above is disclosed, wherein the assembly comprises a least one latch configured to secure at least one position of the RF coil assembly.

According to another embodiment of the present invention, an MRCA as defined above is disclosed, wherein the RF coil is reversibly detachable from the cradle.

According to another embodiment of the present invention, an MRCA as defined above is disclosed, wherein the RF coil is configured to connect to at least a second RF coil.

According to another embodiment of the present invention, an MRCA as defined above is disclosed, wherein the RF coil is connected to at least a second RF coil by a maneuverable connection.

According to another embodiment of the present invention, an MRCA as defined above is disclosed, wherein at least a portion of the RF coil is integrated into MRI-safe material.

According to another embodiment of the present invention, an MRCA as defined above is disclosed, wherein the cradle is supported by a cart.

According to another embodiment of the present invention, an MRCA as defined above is disclosed, wherein at least a portion of the cart is made of MRI safe material.

According to another embodiment of the present invention, an MRCA as defined above is disclosed, wherein at least a portion of the cart is insertable to a selected from a group consisting of: into an MRD bore, into a transport device, into a treatment device, into a storage device and any combination thereof.

According to another embodiment of the present invention, an MRCA as defined above is disclosed, wherein the cart comprises means for maneuvering the cradle providing movement selected from a group consisting of: rotational, tilt, vertical shift, horizontal shift, and any combination thereof.

According to another embodiment of the present invention, an MRCA as defined above is disclosed, wherein the RF assembly, in connection with the cradle and cart is configured to be at least partially insertable into an MRD bore.

According to another embodiment of the present invention, an MRCA as defined above is disclosed, wherein the RF assembly and cradle are sized and shaped to be accommodated within an MRD bore.

According to another embodiment of the present invention, an MRCA as defined above is disclosed, wherein the RF coil assembly comprises a hinge mechanism configured to enable maneuvering of the RF coil in an axis perpendicular to the linearly reciprocating axis.

According to another embodiment of the present invention, an MRCA as defined above is disclosed, wherein the RF coil assembly comprises a plurality of RF coils.

According to another embodiment of the present invention, an MRCA as defined above is disclosed, wherein the RF coil is a transmitting coil, a receiving coil, or both.

According to another embodiment of the present invention, an MRCA as defined above is disclosed, wherein the RF coil is selected from a group consisting of: solenoid, planar, volume, surface, quadrature, and any combination thereof.

According to another embodiment of the present invention, an MRCA as defined above is disclosed, wherein the RF coil is a multiply tuned RF coil.

Additionally or alternatively, the RF coil assembly includes a multi-channel RF coil transceiver and a multi-channel RF coil assembly. Further, the RF coil system is structured for reconfiguration between a plurality of operational modes.

Additionally or alternatively, the multi-channel RF coil assembly is configured to enable parallel imaging.

According to another embodiment of the present invention, an MRCA as defined above is disclosed, wherein the MRCA comprises at least one shim coil.

According to another embodiment of the present invention, an MRCA as defined above is disclosed, wherein the maneuvering mechanism is configured to accept different RF coil assemblies as modular pieces.

According to another embodiment of the present invention, an MRCA as defined above is disclosed, wherein the maneuverable mechanism is configured to accept more than one RF coil assembly, and maneuver the assemblies in a manner selected from a group consisting of: all together, each separately, one following the other, maintaining a predetermined spatial interaction between the assemblies, coordinated movement configured to best fit neonate, movement configured to respond to feedback from MR signal received of the neonate, and any combination thereof.

According to one embodiment of the present invention, a multi-functional maneuvering mechanism (MMM), for maneuvering an RF coil assembly to and from at least two positions: (i) over a neonate immobilized within his/her cradle at time of MR imaging; and (ii) below or aside the cradle when it is not required for imaging, comprising at least one RF coil and maneuvering mechanism; wherein the multi-functional maneuvering mechanism comprises (i) at least one first linear reciprocating mechanism for approaching or otherwise drawing away at least one coil to and from the neonate; and (ii) at least one second tilting mechanism for placing at least one coil away from the neonate.

According to another embodiment of the present invention, an MMM as defined above is disclosed, wherein the assembly is sized and shaped to fit over at least a portion of the neonate.

According to another embodiment of the present invention, an MMM as defined above is disclosed, wherein the assembly is sized and shaped to accommodate at least a portion of the neonate.

According to another embodiment of the present invention, an MMM as defined above is disclosed, wherein the RF coil maneuvering mechanism is configured to enable a plurality of consecutively maneuverable vectors.

According to another embodiment of the present invention, an MMM as defined above is disclosed, wherein the maneuvering mechanism is configured to provide a plurality of positions for the RF coil adjacent to the neonate.

According to another embodiment of the present invention, an MMM as defined above is disclosed, wherein the cradle comprises an emergency release mechanism configured for immediate release of the neonate from the cradle.

According to another embodiment of the present invention, an MMM as defined above is disclosed, wherein the RF coil comprises an emergency release mechanism configured for immediate release of the RF coil from the cradle.

According to another embodiment of the present invention, an MMM as defined above is disclosed, wherein the cradle comprises life support equipment for the neonate.

According to another embodiment of the present invention, an MMM as defined above is disclosed, wherein the cradle comprises means for maintaining the position of the neonate.

According to another embodiment of the present invention, an MMM as defined above is disclosed, wherein the cradle comprises an envelope surrounding an internal environment in which the neonate is accommodated.

According to another embodiment of the present invention, an MMM as defined above is disclosed, wherein the maneuverable mechanism is configured to allow movement of the RF coil assembly within the internal environment, external to the internal environment or both.

According to another embodiment of the present invention, an MMM as defined above is disclosed, wherein the RF coil is configured to have at least one position forming a close environment incubator.

According to another embodiment of the present invention, an MMM as defined above is disclosed, wherein the cradle is selected from a group consisting of: an incubator, a deployed incubator, a transport incubator, a treatment table, a countertop, an operating table, a bed, a baby cradle, a basket, a mattress, a stretcher, a gurney, and any combination thereof.

According to another embodiment of the present invention, an MMM as defined above is disclosed, wherein the RF coil is configured to close an opening of an incubator when in at least one position.

According to another embodiment of the present invention, an MMM as defined above is disclosed, wherein the cradle comprises a selected from a group consisting of: at least one sensor, at least one indicator, at least one medical equipment tubing placement, at least one opening fitted for the insertion of a handlers hand, at least one opening for the passage of life supporting equipment, and any combination thereof. Further, the sensor is connected to an indicator selected from a group consisting of: auditable, visual, sensual, and any combination thereof, and configured to transmit data thereto.

According to another embodiment of the present invention, an MMM as defined above is disclosed, wherein the cradle comprises a user interface configured to monitor or control a selected from a group consisting of: life supporting equipment, MRI operation, position of RF coil, RF coil maneuvering mechanism, opening or closing the cradle, and any combination thereof.

According to another embodiment of the present invention, an MMM as defined above is disclosed, wherein the RF coil assembly comprises at least one sensor configured to sense a selected from a group consisting of: structural integrity of the RF coil, structural integrity of the maneuvering mechanism, position of RF coil, proximity of the neonate to the coil, RF signal received, RF signal transmitted, and any combination thereof. Further, the sensor is connected to an indicator selected from a group consisting of: auditable, visual, sensual, and any combination thereof, and configured to transmit data thereto.

According to another embodiment of the present invention, an MMM as defined above is disclosed, wherein the assembly comprises a handle configured for maneuvering the RF coil assembly by a handler.

According to another embodiment of the present invention, an MMM as defined above is disclosed, wherein the maneuvering mechanism selected from a group consisting of: automated, manual, semi-automated, remote controlled, and any combination thereof.

According to another embodiment of the present invention, an MMM as defined above is disclosed, wherein the maneuverable mechanism comprises means selected from a group consisting of: sliding mechanism, pivot point mechanism, hinge, telescopic mechanism, hydraulic mechanism, turning mechanism, and any combination thereof.

According to another embodiment of the present invention, an MMM as defined above is disclosed, wherein at least a portion of the assembly and cradle are made of a material selected from a group consisting of: a MRI safe material, at least partially transparent material, a sterilizable material, a fire retardant material, and any combination thereof.

According to another embodiment of the present invention, an MMM as defined above is disclosed, wherein the assembly comprises a least one latch configured to secure at least one position of the RF coil assembly.

According to another embodiment of the present invention, an MMM as defined above is disclosed, wherein the RF coil is reversibly detachable from the cradle.

According to another embodiment of the present invention, an MMM as defined above is disclosed, wherein the RF coil is configured to connect to at least a second RF coil.

According to another embodiment of the present invention, an MMM as defined above is disclosed, wherein the RF coil is connected to at least a second RF coil by a maneuverable connection.

According to another embodiment of the present invention, an MMM as defined above is disclosed, wherein at least a portion of the RF coil is integrated into MRI-safe material.

According to another embodiment of the present invention, an MMM as defined above is disclosed, wherein the cradle is supported by a cart.

According to another embodiment of the present invention, an MMM as defined above is disclosed, wherein at least a portion of the cart is made of MRI safe material.

According to another embodiment of the present invention, an MMM as defined above is disclosed, wherein at least a portion of the cart is insertable to a selected from a group consisting of: into an MRD bore, into a transport device, into a treatment device, into a storage device and any combination thereof.

According to another embodiment of the present invention, an MMM as defined above is disclosed, wherein the cart comprises means for maneuvering the cradle providing movement selected from a group consisting of: rotational, tilt, vertical shift, horizontal shift, and any combination thereof.

According to another embodiment of the present invention, an MMM as defined above is disclosed, wherein the RF assembly, in connection with the cradle and cart is configured to be at least partially insertable into an MRD bore.

According to another embodiment of the present invention, an MMM as defined above is disclosed, wherein the RF assembly and cradle are sized and shaped to be accommodated within an MRD bore.

According to another embodiment of the present invention, an MMM as defined above is disclosed, wherein the RF coil assembly comprises a hinge mechanism configured to enable maneuvering of the RF coil in an axis perpendicular to the linearly reciprocating axis.

According to another embodiment of the present invention, an MMM as defined above is disclosed, wherein the RF coil assembly comprises a plurality of RF coils.

According to another embodiment of the present invention, an MMM as defined above is disclosed, wherein the RF coil is a transmitting coil, a receiving coil, or both.

According to another embodiment of the present invention, an MMM as defined above is disclosed, wherein the RF coil is selected from a group consisting of: solenoid, planar, volume, surface, quadrature, and any combination thereof.

According to another embodiment of the present invention, an MMM as defined above is disclosed, wherein the RF coil is a multiply tuned RF coil.

Additionally or alternatively, the RF coil assembly includes a multi-channel RF coil transceiver and a multi-channel RF coil assembly. Further, the RF coil system is structured for reconfiguration between a plurality of operational modes.

Additionally or alternatively, the multi-channel RF coil assembly is configured to enable parallel imaging.

According to another embodiment of the present invention, an MMM as defined above is disclosed, wherein the RF coil assembly comprises at least one shim coil.

According to another embodiment of the present invention, an MMM as defined above is disclosed, wherein the maneuvering mechanism is configured to accept different RF coil assemblies as modular pieces.

According to another embodiment of the present invention, an MMM as defined above is disclosed, wherein the maneuverable mechanism is configured to accept more than one RF coil assembly, and maneuver the assemblies in a manner selected from a group consisting of: all together, each separately, one following the other, maintaining a predetermined spatial interaction between the assemblies, coordinated movement configured to best fit neonate, movement configured to respond to feedback from MR signal received of the neonate, and any combination thereof.

According to one embodiment of the present invention, a method of maneuvering an RF coil, comprising at least two different steps: a step of (i) linearly reciprocating an RF coil assembly for approaching or otherwise drawing away at least one coil to and from a neonate to be MR imaged; and then (ii) tilting the RF coil assembly for placing at least one coil away from the neonate when the neonate is not MR imaged.

According to another embodiment of the present invention, a method as defined above is disclosed, additionally comprising a step of selecting the assembly to be sized and shaped to fit over at least a portion of the neonate.

According to another embodiment of the present invention, a method as defined above is disclosed, additionally comprising a step of selecting the assembly is sized and shaped to accommodate at least a portion of the neonate.

According to another embodiment of the present invention, a method as defined above is disclosed, additionally comprising a step of connecting the cradle to the RF coil by a maneuverable mechanism thereby enabling the RF coil to be positioned in a plurality of positions adjacent to the neonate.

According to another embodiment of the present invention, a method as defined above is disclosed, additionally comprising a step of selecting the cradle having an emergency release mechanism, and configuring the mechanism to immediately release the neonate from the cradle when in need.

According to another embodiment of the present invention, a method as defined above is disclosed, additionally comprising a step of selecting the RF coil having an emergency release mechanism, and configuring the mechanism for immediately releasing the RF coil from the cradle.

According to another embodiment of the present invention, a method as defined above is disclosed, additionally comprising a step of connecting neonate life support equipment to the cradle, the neonate or both.

According to another embodiment of the present invention, a method as defined above is disclosed, additionally comprising a step of selecting the cradle having means for maintaining the position of the neonate and utilizing the means for maintaining the body position of the neonate.

According to another embodiment of the present invention, a method as defined above is disclosed, additionally comprising a step of selecting the cradle having an envelope surrounding an internal environment in which the neonate is accommodated.

According to another embodiment of the present invention, a method as defined above is disclosed, additionally comprising a step of selecting the maneuverable mechanism configured to allow movement of the RF coil assembly within the internal environment, external to the internal environment or both.

According to another embodiment of the present invention, a method as defined above is disclosed, additionally comprising a step of moving the RF coil assembly within the internal environment, external to the internal environment or both.

According to another embodiment of the present invention, a method as defined above is disclosed, additionally comprising a step of selecting the RF coil configured to have at least one position forming a close environment incubator.

According to another embodiment of the present invention, a method as defined above is disclosed, additionally comprising a step of selecting the cradle from a group consisting of: an incubator, a deployed incubator, a transport incubator, a treatment table, a countertop, an operating table, a bed, a baby cradle, a basket, a mattress, a stretcher, a gurney, and any combination thereof.

According to another embodiment of the present invention, a method as defined above is disclosed, additionally comprising a step of selecting the RF coil configured for closing an opening of an incubator when in at least one position.

According to another embodiment of the present invention, a method as defined above is disclosed, additionally comprising a step of selecting the cradle having a selected from a group consisting of: at least one sensor, at least one indicator, at least one medical equipment tubing placement, at least one opening fitted for the insertion of a handlers hand, at least one opening for the passage of life supporting equipment, and any combination thereof. Further, the sensor is connected to an indicator selected from a group consisting of: auditable, visual, sensual, and any combination thereof, and configured to transmit data thereto, thereby enabling the handler or patient to sense the input from the sensor.

According to another embodiment of the present invention, a method as defined above is disclosed, additionally comprising a step of selecting the cradle having a user interface configured for monitoring or controlling a selected from a group consisting of: life supporting equipment, MRI operation, position of RF coil, RF coil maneuvering mechanism, opening or closing the cradle, and any combination thereof.

According to another embodiment of the present invention, a method as defined above is disclosed, additionally comprising at least one of the following steps: (a) monitoring a selected from a group consisting of: life supporting equipment, MRI operation, position of RF coil, RF coil maneuvering mechanism, opening or closing the cradle, and any combination thereof; or, (b) controlling a selected from a group consisting of: life supporting equipment, MRI operation, position of RF coil, RF coil maneuvering mechanism, opening or closing the cradle, and any combination thereof.

According to another embodiment of the present invention, a method as defined above is disclosed, additionally comprising a step of selecting the RF coil assembly having at least one sensor configured to sense a selected from a group consisting of: structural integrity of the RF coil, structural integrity of the maneuvering mechanism, position of RF coil, proximity of the neonate to the coil, RF signal received, RF signal transmitted, and any combination thereof.

According to another embodiment of the present invention, a method as defined above is disclosed, additionally comprising a step of selecting the sensor connected to at least one indicator, and receiving an indication from the sensor.

According to another embodiment of the present invention, a method as defined above is disclosed, additionally comprising a step of selecting the assembly having a handle configured for operation by a handler, and maneuvering the handle, thereby maneuvering a selected from a group consisting of: the RF coil, the cradle, neonate restraining means, neonate mattress, a cart connected to the cradle, and any combination thereof.

According to another embodiment of the present invention, a method as defined above is disclosed, additionally comprising a step of selecting the maneuvering mechanism from a group consisting of: automated, manual, semi-automated, remote controlled, and any combination thereof, and operating the mechanism.

According to another embodiment of the present invention, a method as defined above is disclosed, additionally comprising a step of selecting the maneuverable mechanism having maneuverable means selected from a group consisting of: sliding mechanism, pivot point mechanism, hinge, telescopic mechanism, hydraulic mechanism, turning mechanism, and any combination thereof.

According to another embodiment of the present invention, a method as defined above is disclosed, additionally comprising a step of selecting a cradle in connection with an RF assembly having at least a portion of the assembly and/or cradle are made of a material selected from a group consisting of: a MRI safe material, at least partially transparent material, a sterilizable material, a fire retardant material, and any combination thereof.

According to another embodiment of the present invention, a method as defined above is disclosed, additionally comprising a step of selecting the RF coil assembly having a least one latch configured to secure at least one position of the RF coil assembly, and securing or releasing the RF coil assembly.

According to another embodiment of the present invention, a method as defined above is disclosed, additionally comprising a step of reversibly detaching the RF coil from the cradle.

According to another embodiment of the present invention, a method as defined above is disclosed, additionally comprising a step of selecting the RF coil configured to connect to at least a second RF coil, and connecting at least a second RF coil.

According to another embodiment of the present invention, a method as defined above is disclosed, additionally comprising a step of selecting the RF coil connected to at least a second RF coil by a maneuverable connection, and maneuvering the RF coil relative to at least a second RF coil.

According to another embodiment of the present invention, a method as defined above is disclosed, additionally comprising a step of selecting the RF coil of which at least a portion of is integrated into MRI-safe material.

According to another embodiment of the present invention, a method as defined above is disclosed, additionally comprising a step of supporting the cradle in connection with an RF coil assembly by a cart.

According to another embodiment of the present invention, a method as defined above is disclosed, additionally comprising a step of selecting the cart in which at least a portion of is made of MRI safe material.

According to another embodiment of the present invention, a method as defined above is disclosed, additionally comprising a step of selecting the cart in which at least a portion of is insertable to a selected from a group consisting of: into an MRD bore, into a transport device, into a treatment device, into a storage device, and any combination thereof.

According to another embodiment of the present invention, a method as defined above is disclosed, additionally comprising a step of selecting the cart having means for maneuvering the cradle providing movement selected from a group consisting of: rotational, tilt, vertical shift, horizontal shift, and any combination thereof, and maneuvering the cradle.

According to another embodiment of the present invention, a method as defined above is disclosed, additionally comprising a step of selecting the RF assembly, in connection with the cradle and the cart configured to be at least partially insertable into an MRD bore.

According to another embodiment of the present invention, a method as defined above is disclosed, additionally comprising a step of selecting the RF assembly and cradle are sized and shaped to be accommodated within an MRD bore.

According to another embodiment of the present invention, a method as defined above is disclosed, additionally comprising a step of selecting the RF coil assembly having a hinge mechanism, thereby enabling maneuvering of the RF coil in an axis perpendicular to the linearly reciprocating axis.

According to another embodiment of the present invention, a method as defined above is disclosed, additionally comprising a step of selecting the RF coil assembly having a plurality of RF coils.

According to another embodiment of the present invention, a method as defined above is disclosed, additionally comprising a step of transmitting, receiving, or both with the RF coil.

According to another embodiment of the present invention, a method as defined above is disclosed, additionally comprising a step of selecting the RF coil from a group consisting of: solenoid, planar, volume, surface, quadrature, and any combination thereof.

According to another embodiment of the present invention, a method as defined above is disclosed, additionally comprising a step of selecting the RF coil configured to be a multiply tuned RF coil, and reconfiguring the RF coil assembly between pluralities of operational modes.

According to another embodiment of the present invention, a method as defined above is disclosed, additionally comprising a step of selecting the maneuvering mechanism is configured to accept different RF coil assemblies as modular pieces, and connecting at least one modular RF coil assembly.

According to another embodiment of the present invention, a method as defined above is disclosed, additionally comprising a step of selecting the maneuvering mechanism configured to accept more than one RF coil assembly, and maneuvering the assemblies in a manner selected from a group consisting of: all together, each separately, one following the other, maintaining a predetermined spatial interaction between the assemblies, coordinated movement configured to best fit neonate, movement configured to respond to feedback from MR signal received of the neonate, and any combination thereof.

According to one embodiment of the present invention, an MRI-compatible neonate's cradle comprising a maneuverable RF coil; comprising a multi-functional maneuvering mechanism for maneuvering an RF coil assembly to and from at least two positions (i) over a neonate immobilized within his/her cradle at time of MR imaging; and (ii) below or aside the cradle when it is not required for imaging, comprising at least one RF coil and maneuvering mechanism; wherein the multi-functional maneuvering mechanism comprises (i) at least one first linear reciprocating mechanism for approaching or otherwise drawing away at least one coil to and from the neonate; and (ii) at least one second tilting mechanism for placing at least one coil away from the neonate.

According to one embodiment of the present invention, an MRI-compatible neonate's cradle comprising a maneuverable RF coil; the maneuverable RF coil assembly is useful for being maneuvered at both positions (i) over a neonate immobilized within his/her cradle at time of MR imaging; and (ii) below or aside the cradle when it is not required for imaging, comprising at least one RF coil and maneuvering mechanism; wherein the maneuvering mechanism comprises both (i) a linear reciprocating mechanism for approaching or otherwise drawing away at least one coil to and from the neonate; and (ii) tilting mechanism for placing at least one coil away from the neonate.

According to another embodiment of the present invention, an MRI-compatible cradle as defined above is disclosed, wherein the assembly is sized and shaped to fit over, accommodate, or both, at least a portion of the neonate.

According to another embodiment of the present invention, an MRI-compatible cradle as defined above is disclosed, wherein the maneuvering mechanism is configured to provide a plurality of positions for the RF coil adjacent to the neonate.

According to another embodiment of the present invention, an MRI-compatible cradle as defined above is disclosed, wherein the MRI system comprises an emergency release mechanism configured to immediately release a selected from a group consisting of: the neonate from the cradle, the RF coil from the cradle, the cradle form the MRD, the cart from the MRD, the neonate from the MRD, the cradle from the cart, the RF coil from the cart, the neonate from the cart, and any combination thereof. According to another embodiment of the present invention, MRI-compatible cradle as defined above is disclosed, wherein the cradle, the cart or both, comprise life support equipment for the neonate.

According to another embodiment of the present invention, an MRI-compatible cradle as defined above is disclosed, wherein the RF coil maneuvering mechanism is configured to enable a plurality of consecutively maneuverable vectors.

According to another embodiment of the present invention, an MRI-compatible cradle as defined above is disclosed, wherein the cradle, the cart or both comprise means for maintaining the position of the neonate.

According to another embodiment of the present invention, an MRI-compatible cradle as defined above is disclosed, wherein the cradle comprises an envelope surrounding an internal environment in which the neonate is accommodated.

According to another embodiment of the present invention, an MRI-compatible cradle as defined above is disclosed, wherein the maneuverable mechanism is configured to allow movement of the RF coil assembly within the internal environment, external to the internal environment or both.

According to another embodiment of the present invention, an MRI-compatible cradle as defined above is disclosed, wherein the RF coil is configured to have at least one position forming a close environment incubator.

According to another embodiment of the present invention, an MRI-compatible cradle as defined above is disclosed, wherein the cradle is selected from a group consisting of: an incubator, a deployed incubator, a transport incubator, a treatment table, a countertop, an operating table, a bed, a baby cradle, a basket, a mattress, a stretcher, a gurney, and any combination thereof.

According to another embodiment of the present invention, an MRI-compatible cradle as defined above is disclosed, wherein the RF coil is configured to close an opening of an incubator when in at least one position.

According to another embodiment of the present invention, an MRI-compatible cradle as defined above is disclosed, wherein the RF coil assembly is connected to at least a portion of a selected from a group consisting of: the cart, the incubator, the MRD, the cradle, and any combination thereof.

According to another embodiment of the invention, an MRI-compatible cradle as defined above is disclosed, wherein the RF coil connection is reversible.

According to another embodiment of the present invention, an MRI-compatible cradle as defined above is disclosed, wherein the cradle comprises a selected from a group consisting of: at least one sensor, at least one indicator, at least one medical equipment tubing placement, at least one opening fitted for the insertion of a handlers hand, at least one opening for the passage of life supporting equipment, and any combination thereof. Further, the sensor is connected to an indicator selected from a group consisting of: auditable, visual, sensual, and any combination thereof, and configured to transmit data thereto.

According to another embodiment of the present invention, an MRI-compatible cradle as defined above is disclosed, wherein the cradle comprises a user interface configured to monitor or control a selected from a group consisting of: life supporting equipment, MRI operation, position of RF coil, RF coil maneuvering mechanism, opening or closing the cradle, and any combination thereof.

According to another embodiment of the present invention, an MRI-compatible cradle as defined above is disclosed, wherein the RF coil assembly comprises at least one sensor configured to sense a selected from a group consisting of: structural integrity of the RF coil, structural integrity of the maneuvering mechanism, position of RF coil, proximity of the neonate to the coil, RF signal received, RF signal transmitted, and any combination thereof. Further, the sensor is connected to an indicator selected from a group consisting of: auditable, visual, sensual, and any combination thereof, and configured to transmit data thereto.

According to another embodiment of the present invention, an MRI-compatible cradle as defined above is disclosed, wherein the assembly comprises a handle configured for maneuvering the RF coil assembly by a handler.

According to another embodiment of the present invention, an MRI-compatible cradle as defined above is disclosed, wherein the maneuvering mechanism selected from a group consisting of: automated, manual, semi-automated, remote controlled, and any combination thereof.

According to another embodiment of the present invention, an MRI-compatible cradle as defined above is disclosed, wherein the maneuverable mechanism comprises means selected from a group consisting of: sliding mechanism, pivot point mechanism, hinge, telescopic mechanism, hydraulic mechanism, turning mechanism, and any combination thereof.

According to another embodiment of the present invention, an MRI-compatible cradle as defined above is disclosed, wherein at least a portion of the assembly, cradle, and cart are made of a material selected from a group consisting of: a MRI safe material, at least partially transparent material, a sterilizable material, a fire retardant material, and any combination thereof.

According to another embodiment of the present invention, an MRI-compatible cradle as defined above is disclosed, wherein the assembly comprises a least one latch configured to secure at least one position of the RF coil assembly.

According to another embodiment of the present invention, an MRI-compatible cradle as defined above is disclosed, wherein the RF coil is reversibly detachable from the cradle.

According to another embodiment of the present invention, an MRI-compatible cradle as defined above is disclosed, wherein the RF coil is configured to connect to at least a second RF coil.

According to another embodiment of the present invention, an MRI-compatible cradle as defined above is disclosed, wherein the RF coil is connected to at least a second RF coil by a maneuverable connection.

According to another embodiment of the present invention, an MRI-compatible cradle as defined above is disclosed, wherein at least a portion of the RF coil is integrated into MRI-safe material.

According to another embodiment of the present invention, an MRI-compatible cradle as defined above is disclosed, wherein the cradle is supported by a cart.

According to another embodiment of the present invention, an MRI-compatible cradle as defined above is disclosed, wherein at least a portion of the cart is made of MRI safe material.

According to another embodiment of the present invention, an MRI-compatible cradle as defined above is disclosed, wherein at least a portion of the cart is insertable to a selected from a group consisting of: into an MRD bore, into a transport device, into a treatment device, into a storage device and any combination thereof.

According to another embodiment of the present invention, an MRI-compatible cradle as defined above is disclosed, wherein the cart comprises means for maneuvering the cradle providing movement selected from a group consisting of: rotational, tilt, vertical shift, horizontal shift, and any combination thereof.

According to another embodiment of the present invention, an MRI-compatible cradle as defined above is disclosed, wherein the RF assembly, in connection with the cradle and cart is configured to be at least partially insertable into an MRD bore.

According to another embodiment of the present invention, an MRI-compatible cradle as defined above is disclosed, wherein the RF assembly and cradle are sized and shaped to be accommodated within an MRD bore.

According to another embodiment of the present invention, an MRI-compatible cradle as defined above is disclosed, wherein the RF coil assembly comprises a hinge mechanism configured to enable maneuvering of the RF coil in an axis perpendicular to the linearly reciprocating axis.

According to another embodiment of the present invention, an MRI-compatible cradle as defined above is disclosed, wherein the RF coil assembly comprises a plurality of RF coils.

According to another embodiment of the present invention, an MRI-compatible cradle as defined above is disclosed, wherein the RF coil is a transmitting coil, a receiving coil, or both.

According to another embodiment of the present invention, an MRI-compatible cradle as defined above is disclosed, wherein the RF coil is selected from a group consisting of: solenoid, planar, volume, surface, quadrature, and any combination thereof.

According to another embodiment of the present invention, an MRI-compatible cradle as defined above is disclosed, wherein the RF coil is a multiply tuned RF coil.

Additionally or alternatively, the RF coil assembly includes a multi-channel RF coil transceiver and a multi-channel RF coil assembly. Further, the RF coil system is structured for reconfiguration between a plurality of operational modes.

Additionally or alternatively, the multi-channel RF coil assembly is configured to enable parallel imaging.

According to another embodiment of the present invention, an MRI-compatible cradle as defined above is disclosed, wherein the RF coil assembly comprises at least one shim coil.

According to another embodiment of the present invention, an MRI-compatible cradle as defined above is disclosed, wherein the maneuvering mechanism is configured to accept different RF coil assemblies as modular pieces.

According to another embodiment of the present invention, an MRI-compatible cradle as defined above is disclosed, wherein the maneuverable mechanism is configured to accept more than one RF coil assembly, and maneuver the assemblies in a manner selected from a group consisting of: all together, each separately, one following the other, maintaining a predetermined spatial interaction between the assemblies, coordinated movement configured to best fit neonate, movement configured to respond to feedback from MR signal received of the neonate, and any combination thereof.

An MRI-compatible cart in connection with an MRI-compatible neonate's cradle comprising a maneuverable RF coil; wherein the cart and the MRI-compatible neonate's cradle are adapted by means of size and shape to both (i) accommodate the cradle within an MRD open bore whilst (ii) the cart is at least partially accommodated either within the MRD infrastructure or surround the same.

An MRI-compatible cart in connection with an MRI-compatible neonate's cradle, the cradle comprises or otherwise in connection with a maneuverable RF coil assembly is useful for being maneuvered at both positions (i) over a neonate immobilized within his/her cradle at time of MR imaging; and (ii) below or aside the cradle when it is not required for imaging, comprising at least one RF coil and maneuvering mechanism; wherein the maneuvering mechanism comprises both (i) a linear reciprocating mechanism for approaching or otherwise drawing away at least one coil to and from the neonate; and (ii) tilting mechanism for placing at least one coil away from the neonate.

An MRI-compatible cart in connection with an MRI-compatible neonate's cradle, the cradle comprises or otherwise in connection with a multi-functional maneuvering mechanism for maneuvering an RF coil assembly to and from at least two positions (i) over a neonate immobilized within his/her cradle at time of MR imaging; and (ii) below or aside the cradle when it is not required for imaging, comprising at least one RF coil and maneuvering mechanism; wherein the multi-functional maneuvering mechanism comprises (i) at least one first linear reciprocating mechanism for approaching or otherwise drawing away at least one coil to and from the neonate; and (ii) at least one second tilting mechanism for placing at least one coil away from the neonate.

According to another embodiment of the present invention, an MRI-compatible cart as defined above is disclosed, wherein the assembly is sized and shaped to fit over, accommodate, or both, at least a portion of the neonate.

According to another embodiment of the present invention, an MRI-compatible cart as defined above is disclosed, wherein the maneuvering mechanism is configured to provide a plurality of positions for the RF coil adjacent to the neonate.

According to another embodiment of the present invention, an MRI-compatible cart as defined above is disclosed, wherein the RF coil maneuvering mechanism is configured to enable a plurality of consecutively maneuverable vectors.

According to another embodiment of the present invention, an MRI-compatible cart as defined above is disclosed, wherein the MRI system comprises an emergency release mechanism configured to immediately release a selected from a group consisting of: the neonate from the cradle, the RF coil from the cradle, the cradle form the MRD, the cart from the MRD, the neonate from the MRD, the cradle from the cart, the RF coil from the cart, the neonate from the cart, and any combination thereof. According to another embodiment of the present invention, MRI-compatible cart as defined above is disclosed, wherein the cradle, the cart or both, comprise life support equipment for the neonate.

According to another embodiment of the present invention, an MRI-compatible cart as defined above is disclosed, wherein the cradle, the cart or both comprise means for maintaining the position of the neonate.

According to another embodiment of the present invention, an MRI-compatible cart as defined above is disclosed, wherein the cradle comprises an envelope surrounding an internal environment in which the neonate is accommodated.

According to another embodiment of the present invention, an MRI-compatible cart as defined above is disclosed, wherein the maneuverable mechanism is configured to allow movement of the RF coil assembly within the internal environment, external to the internal environment or both.

According to another embodiment of the present invention, an MRI-compatible cart as defined above is disclosed, wherein the RF coil is configured to have at least one position forming a close environment incubator.

According to another embodiment of the present invention, an MRI-compatible cart as defined above is disclosed, wherein the cradle is selected from a group consisting of: an incubator, a deployed incubator, a transport incubator, a treatment table, a countertop, an operating table, a bed, a baby cradle, a basket, a mattress, a stretcher, a gurney, and any combination thereof.

According to another embodiment of the present invention, an MRI-compatible cart as defined above is disclosed, wherein the RF coil is configured to close an opening of an incubator when in at least one position.

According to another embodiment of the present invention, an MRI-compatible cart as defined above is disclosed, wherein the RF coil assembly is connected to at least a portion of a selected from a group consisting of: the cart, the incubator, the MRD, the cradle, and any combination thereof.

According to another embodiment of the invention, an MRI-compatible cart as defined above is disclosed, wherein the RF coil connection is reversible.

According to another embodiment of the present invention, an MRI-compatible cart as defined above is disclosed, wherein the cradle comprises a selected from a group consisting of: at least one sensor, at least one indicator, at least one medical equipment tubing placement, at least one opening fitted for the insertion of a handlers hand, at least one opening for the passage of life supporting equipment, and any combination thereof. Further, the sensor is connected to an indicator selected from a group consisting of: auditable, visual, sensual, and any combination thereof, and configured to transmit data thereto.

According to another embodiment of the present invention, an MRI-compatible cart as defined above is disclosed, wherein the cradle comprises a user interface configured to monitor or control a selected from a group consisting of: life supporting equipment, MRI operation, position of RF coil, RF coil maneuvering mechanism, opening or closing the cradle, and any combination thereof.

According to another embodiment of the present invention, an MRI-compatible cart as defined above is disclosed, wherein the RF coil assembly comprises at least one sensor configured to sense a selected from a group consisting of: structural integrity of the RF coil, structural integrity of the maneuvering mechanism, position of RF coil, proximity of the neonate to the coil, RF signal received, RF signal transmitted, and any combination thereof. Further, the sensor is connected to an indicator selected from a group consisting of: auditable, visual, sensual, and any combination thereof, and configured to transmit data thereto.

According to another embodiment of the present invention, an MRI-compatible cart as defined above is disclosed, wherein the assembly comprises a handle configured for maneuvering the RF coil assembly by a handler.

According to another embodiment of the present invention, an MRI-compatible cart as defined above is disclosed, wherein the maneuvering mechanism selected from a group consisting of: automated, manual, semi-automated, remote controlled, and any combination thereof.

According to another embodiment of the present invention, an MRI-compatible cart as defined above is disclosed, wherein the maneuverable mechanism comprises means selected from a group consisting of: sliding mechanism, pivot point mechanism, hinge, telescopic mechanism, hydraulic mechanism, turning mechanism, and any combination thereof.

According to another embodiment of the present invention, an MRI-compatible cart as defined above is disclosed, wherein at least a portion of the assembly, cradle, and cart are made of a material selected from a group consisting of: a MRI safe material, at least partially transparent material, a sterilizable material, a fire retardant material, and any combination thereof.

According to another embodiment of the present invention, an MRI-compatible cart as defined above is disclosed, wherein the assembly comprises a least one latch configured to secure at least one position of the RF coil assembly.

According to another embodiment of the present invention, an MRI-compatible cart as defined above is disclosed, wherein the RF coil is reversibly detachable from the cradle.

According to another embodiment of the present invention, an MRI-compatible cart as defined above is disclosed, wherein the RF coil is configured to connect to at least a second RF coil.

According to another embodiment of the present invention, an MRI-compatible cart as defined above is disclosed, wherein the RF coil is connected to at least a second RF coil by a maneuverable connection.

According to another embodiment of the present invention, an MRI-compatible cart as defined above is disclosed, wherein at least a portion of the RF coil is integrated into MRI-safe material.

According to another embodiment of the present invention, an MRI-compatible cart as defined above is disclosed, wherein the cradle is supported by a cart.

According to another embodiment of the present invention, an MRI-compatible cart as defined above is disclosed, wherein at least a portion of the cart is made of MRI safe material.

According to another embodiment of the present invention, an MRI-compatible cart as defined above is disclosed, wherein at least a portion of the cart is insertable to a selected from a group consisting of: into an MRD bore, into a transport device, into a treatment device, into a storage device and any combination thereof.

According to another embodiment of the present invention, an MRI-compatible cart as defined above is disclosed, wherein the cart comprises means for maneuvering the cradle providing movement selected from a group consisting of: rotational, tilt, vertical shift, horizontal shift, and any combination thereof.

According to another embodiment of the present invention, an MRI-compatible cart as defined above is disclosed, wherein the RF assembly, in connection with the cradle and cart is configured to be at least partially insertable into an MRD bore.

According to another embodiment of the present invention, an MRI-compatible cart as defined above is disclosed, wherein the RF assembly and cradle are sized and shaped to be accommodated within an MRD bore.

According to another embodiment of the present invention, an MRI-compatible cart as defined above is disclosed, wherein the RF coil assembly comprises a hinge mechanism configured to enable maneuvering of the RF coil in an axis perpendicular to the linearly reciprocating axis.

According to another embodiment of the present invention, an MRI-compatible cart as defined above is disclosed, wherein the RF coil assembly comprises a plurality of RF coils.

According to another embodiment of the present invention, an MRI-compatible cart as defined above is disclosed, wherein the RF coil is a transmitting coil, a receiving coil, or both.

According to another embodiment of the present invention, an MRI-compatible cart as defined above is disclosed, wherein the RF coil is selected from a group consisting of: solenoid, planar, volume, surface, quadrature, and any combination thereof.

According to another embodiment of the present invention, an MRI-compatible cart as defined above is disclosed, wherein the RF coil is a multiply tuned RF coil.

Additionally or alternatively, the RF coil assembly includes a multi-channel RF coil transceiver and a multi-channel RF coil assembly. Further, the RF coil system is structured for reconfiguration between a plurality of operational modes.

Additionally or alternatively, the multi-channel RF coil assembly is configured to enable parallel imaging.

According to another embodiment of the present invention, an MRI-compatible cart as defined above is disclosed, wherein the RF coil assembly comprises at least one shim coil.

According to another embodiment of the present invention, an MRI-compatible cart as defined above is disclosed, wherein the maneuvering mechanism is configured to accept different RF coil assemblies as modular pieces.

According to another embodiment of the present invention, an MRI-compatible cart as defined above is disclosed, wherein the maneuverable mechanism is configured to accept more than one RF coil assembly, and maneuver the assemblies in a manner selected from a group consisting of: all together, each separately, one following the other, maintaining a predetermined spatial interaction between the assemblies, coordinated movement configured to best fit neonate, movement configured to respond to feedback from MR signal received of the neonate, and any combination thereof.

An MRI-system comprising an MRD, and a cart, insertably accommodated within or around the MRD's infrastructure, the cart comprising or otherwise being in connection with an MRI-compatible neonate's cradle comprising a maneuverable RF coil.

An MRI-system comprising an MRD, and a cart, insertably accommodated within or around the MRD's infrastructure, the cart comprising or otherwise being in connection with an MRI-compatible neonate's cradle and a RF coil assembly maneuvering mechanism; wherein at least one is true: (a) the maneuvering mechanism comprises both (i) a linear reciprocating mechanism for approaching or otherwise drawing away at least one coil to and from the neonate; and (ii) tilting mechanism for placing at least one coil away from the neonate; (b) the maneuvering mechanism is a multi-functional maneuvering mechanism comprises (i) at least one first linear reciprocating mechanism for approaching or otherwise drawing away at least one coil to and from the neonate; and (ii) at least one second tilting mechanism for placing at least one coil away from the neonate.

According to another embodiment of the present invention, an MRI system as defined above is disclosed, wherein the assembly is sized and shaped to fit over, accommodate, or both, at least a portion of the neonate.

According to another embodiment of the present invention, an MRI system as defined above is disclosed, wherein the maneuvering mechanism is configured to provide a plurality of positions for the RF coil adjacent to the neonate.

According to another embodiment of the present invention, an MRI system as defined above is disclosed, wherein the RF coil maneuvering mechanism is configured to enable a plurality of consecutively maneuverable vectors.

According to another embodiment of the present invention, an MRI system as defined above is disclosed, wherein the MRI system comprises an emergency release mechanism configured to immediately release a selected from a group consisting of: the neonate from the cradle, the RF coil from the cradle, the cradle form the MRD, the cart from the MRD, the neonate from the MRD, the cradle from the cart, the RF coil from the cart, the neonate from the cart, and any combination thereof.

According to another embodiment of the present invention, MRI system as defined above is disclosed, wherein the cradle, the cart or both, comprise life support equipment for the neonate.

According to another embodiment of the present invention, an MRI system as defined above is disclosed, wherein the cradle, the cart or both comprise means for maintaining the position of the neonate.

According to another embodiment of the present invention, an MRI system as defined above is disclosed, wherein the cradle comprises an envelope surrounding an internal environment in which the neonate is accommodated.

According to another embodiment of the present invention, an MRI system as defined above is disclosed, wherein the maneuverable mechanism is configured to allow movement of the RF coil assembly within the internal environment, external to the internal environment or both.

According to another embodiment of the present invention, an MRI system as defined above is disclosed, wherein the RF coil is configured to have at least one position forming a close environment incubator.

According to another embodiment of the present invention, an MRI system as defined above is disclosed, wherein the cradle is selected from a group consisting of: an incubator, a deployed incubator, a transport incubator, a treatment table, a countertop, an operating table, a bed, a baby cradle, a basket, a mattress, a stretcher, a gurney, and any combination thereof.

According to another embodiment of the present invention, an MRI system as defined above is disclosed, wherein the RF coil is configured to close an opening of an incubator when in at least one position.

According to another embodiment of the present invention, an MRI system as defined above is disclosed, wherein the RF coil assembly is connected to at least a portion of a selected from a group consisting of: the cart, the incubator, the MRD, the cradle, and any combination thereof.

According to another embodiment of the invention, an MRI system as defined above is disclosed, wherein the RF coil connection is reversible.

According to another embodiment of the present invention, an MRI system as defined above is disclosed, wherein the cradle comprises a selected from a group consisting of: at least one sensor, at least one indicator, at least one medical equipment tubing placement, at least one opening fitted for the insertion of a handlers hand, at least one opening for the passage of life supporting equipment, and any combination thereof. Further, the sensor is connected to an indicator selected from a group consisting of: auditable, visual, sensual, and any combination thereof, and configured to transmit data thereto.

According to another embodiment of the present invention, an MRI system as defined above is disclosed, wherein the cradle comprises a user interface configured to monitor or control a selected from a group consisting of: life supporting equipment, MRI operation, position of RF coil, RF coil maneuvering mechanism, opening or closing the cradle, and any combination thereof.

According to another embodiment of the present invention, an MRI system as defined above is disclosed, wherein the RF coil assembly comprises at least one sensor configured to sense a selected from a group consisting of: structural integrity of the RF coil, structural integrity of the maneuvering mechanism, position of RF coil, proximity of the neonate to the coil, RF signal received, RF signal transmitted, and any combination thereof. Further, the sensor is connected to an indicator selected from a group consisting of: auditable, visual, sensual, and any combination thereof, and configured to transmit data thereto.

According to another embodiment of the present invention, an MRI system as defined above is disclosed, wherein the assembly comprises a handle configured for maneuvering the RF coil assembly by a handler.

According to another embodiment of the present invention, an MRI system as defined above is disclosed, wherein the maneuvering mechanism selected from a group consisting of: automated, manual, semi-automated, remote controlled, and any combination thereof.

According to another embodiment of the present invention, an MRI system as defined above is disclosed, wherein the maneuverable mechanism comprises means selected from a group consisting of: sliding mechanism, pivot point mechanism, hinge, telescopic mechanism, hydraulic mechanism, turning mechanism, and any combination thereof.

According to another embodiment of the present invention, an MRI system as defined above is disclosed, wherein at least a portion of the assembly, cradle, and cart are made of a material selected from a group consisting of: a MRI safe material, at least partially transparent material, a sterilizable material, a fire retardant material, and any combination thereof.

According to another embodiment of the present invention, an MRI system as defined above is disclosed, wherein the assembly comprises a least one latch configured to secure at least one position of the RF coil assembly.

According to another embodiment of the present invention, an MRI system as defined above is disclosed, wherein the RF coil is reversibly detachable from the cradle.

According to another embodiment of the present invention, an MRI system as defined above is disclosed, wherein the RF coil is configured to connect to at least a second RF coil.

According to another embodiment of the present invention, an MRI system as defined above is disclosed, wherein the RF coil is connected to at least a second RF coil by a maneuverable connection.

According to another embodiment of the present invention, an MRI system as defined above is disclosed, wherein at least a portion of the RF coil is integrated into MRI-safe material.

According to another embodiment of the present invention, an MRI system as defined above is disclosed, wherein the cradle is supported by a cart.

According to another embodiment of the present invention, an MRI system as defined above is disclosed, wherein at least a portion of the cart is made of MRI safe material.

According to another embodiment of the present invention, an MRI system as defined above is disclosed, wherein at least a portion of the cart is insertable to a selected from a group consisting of: into an MRD bore, into a transport device, into a treatment device, into a storage device and any combination thereof.

According to another embodiment of the present invention, an MRI system as defined above is disclosed, wherein the cart comprises means for maneuvering the cradle providing movement selected from a group consisting of: rotational, tilt, vertical shift, horizontal shift, and any combination thereof.

According to another embodiment of the present invention, an MRI system as defined above is disclosed, wherein the RF assembly, in connection with the cradle and cart is configured to be at least partially insertable into an MRD bore.

According to another embodiment of the present invention, an MRI system as defined above is disclosed, wherein the RF assembly and cradle are sized and shaped to be accommodated within an MRD bore.

According to another embodiment of the present invention, an MRI system as defined above is disclosed, wherein the RF coil assembly comprises a hinge mechanism configured to enable maneuvering of the RF coil in an axis perpendicular to the linearly reciprocating axis.

According to another embodiment of the present invention, an MRI system as defined above is disclosed, wherein the RF coil assembly comprises a plurality of RF coils.

According to another embodiment of the present invention, an MRI system as defined above is disclosed, wherein the RF coil is a transmitting coil, a receiving coil, or both.

According to another embodiment of the present invention, an MRI system as defined above is disclosed, wherein the RF coil is selected from a group consisting of: solenoid, planar, volume, surface, quadrature, and any combination thereof. According to another embodiment of the present invention, an MRI system as defined above is disclosed, wherein the RF coil is a multiply tuned RF coil.

Additionally or alternatively, the RF coil assembly includes a multi-channel RF coil transceiver and a multi-channel RF coil assembly. Further, the RF coil system is structured for reconfiguration between a plurality of operational modes.

Additionally or alternatively, the multi-channel RF coil assembly is configured to enable parallel imaging.

According to another embodiment of the present invention, an MRI system as defined above is disclosed, wherein the RF coil assembly comprises at least one shim coil.

According to another embodiment of the present invention, an MRI system as defined above is disclosed, wherein the maneuvering mechanism is configured to accept different RF coil assemblies as modular pieces.

According to another embodiment of the present invention, an MRI system as defined above is disclosed, wherein the maneuverable mechanism is configured to accept more than one RF coil assembly, and maneuver the assemblies in a manner selected from a group consisting of: all together, each separately, one following the other, maintaining a predetermined spatial interaction between the assemblies, coordinated movement configured to best fit neonate, movement configured to respond to feedback from MR signal received of the neonate, and any combination thereof.

According to one embodiment of the invention, a method of providing an MRI-compatible neonate's cradle with a maneuverable RF coil, comprising at least two different steps of maneuvering an RF coil: a step of (i) linearly reciprocating an RF coil assembly for approaching or otherwise drawing away at least one coil to and from a neonate to be MR imaged; and then (ii) tilting the RF coil assembly for placing at least one coil away from the neonate when the neonate is not MR imaged.

According to another embodiment of the present invention, a method as defined above is disclosed, additionally comprising a step of selecting the assembly to be sized and shaped to fit over at least a portion of the neonate.

According to another embodiment of the present invention, a method as defined above is disclosed, additionally comprising a step of selecting the assembly is sized and shaped to accommodate at least a portion of the neonate.

According to another embodiment of the present invention, a method as defined above is disclosed, additionally comprising a step of connecting the cradle to the RF coil by a maneuverable mechanism thereby enabling the RF coil to be positioned in a plurality of positions adjacent to the neonate.

According to another embodiment of the present invention, a method as defined above is disclosed, additionally comprising a step of selecting the cradle having an emergency release mechanism, and configuring the mechanism to immediately release the neonate from the cradle when in need.

According to another embodiment of the present invention, a method as defined above is disclosed, additionally comprising a step of selecting the RF coil having an emergency release mechanism, and configuring the mechanism for immediately releasing the RF coil from the cradle.

According to another embodiment of the present invention, a method as defined above is disclosed, additionally comprising a step of connecting neonate life support equipment to the cradle, the neonate or both.

According to another embodiment of the present invention, a method as defined above is disclosed, additionally comprising a step of selecting the cradle having means for maintaining the position of the neonate and utilizing the means for maintaining the body position of the neonate.

According to another embodiment of the present invention, a method as defined above is disclosed, additionally comprising a step of selecting the cradle having an envelope surrounding an internal environment in which the neonate is accommodated.

According to another embodiment of the present invention, a method as defined above is disclosed, additionally comprising a step of selecting the maneuverable mechanism configured to allow movement of the RF coil assembly within the internal environment, external to the internal environment or both.

According to another embodiment of the present invention, a method as defined above is disclosed, additionally comprising a step of moving the RF coil assembly within the internal environment, external to the internal environment or both.

According to another embodiment of the present invention, a method as defined above is disclosed, additionally comprising a step of selecting the RF coil configured to have at least one position forming a close environment incubator.

According to another embodiment of the present invention, a method as defined above is disclosed, additionally comprising a step of selecting the cradle from a group consisting of: an incubator, a deployed incubator, a transport incubator, a treatment table, a countertop, an operating table, a bed, a baby cradle, a basket, a mattress, a stretcher, a gurney, and any combination thereof.

According to another embodiment of the present invention, a method as defined above is disclosed, additionally comprising a step of selecting the RF coil configured for closing an opening of an incubator when in at least one position.

According to another embodiment of the present invention, a method as defined above is disclosed, additionally comprising a step of selecting the cradle having a selected from a group consisting of: at least one sensor, at least one indicator, at least one medical equipment tubing placement, at least one opening fitted for the insertion of a handlers hand, at least one opening for the passage of life supporting equipment, and any combination thereof.

According to another embodiment of the present invention, a method as defined above is disclosed, additionally comprising a step of selecting the cradle having a user interface configured for monitoring or controlling a selected from a group consisting of: life supporting equipment, MRI operation, position of RF coil, RF coil maneuvering mechanism, opening or closing the cradle, and any combination thereof.

According to another embodiment of the present invention, a method as defined above is disclosed, additionally comprising at least one of the following steps: (a) monitoring a selected from a group consisting of: life supporting equipment, MRI operation, position of RF coil, RF coil maneuvering mechanism, opening or closing the cradle, and any combination thereof; or, (b) controlling a selected from a group consisting of: life supporting equipment, MRI operation, position of RF coil, RF coil maneuvering mechanism, opening or closing the cradle, and any combination thereof.

According to another embodiment of the present invention, a method as defined above is disclosed, additionally comprising a step of selecting the RF coil assembly having at least one sensor configured to sense a selected from a group consisting of: structural integrity of the RF coil, structural integrity of the maneuvering mechanism, position of RF coil, proximity of the neonate to the coil, RF signal received, RF signal transmitted, and any combination thereof.

According to another embodiment of the present invention, a method as defined above is disclosed, additionally comprising a step of selecting the sensor connected to at least one indicator, and receiving an indication from the sensor.

According to another embodiment of the present invention, a method as defined above is disclosed, additionally comprising a step of selecting the assembly having a handle configured for operation by a handler, and maneuvering the handle, thereby maneuvering a selected from a group consisting of: the RF coil, the cradle, neonate restraining means, neonate mattress, a cart connected to the cradle, and any combination thereof.

According to another embodiment of the present invention, a method as defined above is disclosed, additionally comprising a step of selecting the maneuvering mechanism from a group consisting of: automated, manual, semi-automated, remote controlled, and any combination thereof, and operating the mechanism.

According to another embodiment of the present invention, a method as defined above is disclosed, additionally comprising a step of selecting the maneuverable mechanism having maneuverable means selected from a group consisting of: sliding mechanism, pivot point mechanism, hinge, telescopic mechanism, hydraulic mechanism, turning mechanism, and any combination thereof.

According to another embodiment of the present invention, a method as defined above is disclosed, additionally comprising a step of selecting a cradle in connection with an RF assembly having at least a portion of the assembly and/or cradle are made of a material selected from a group consisting of: a MRI safe material, at least partially transparent material, a sterilizable material, a fire retardant material, and any combination thereof.

According to another embodiment of the present invention, a method as defined above is disclosed, additionally comprising a step of selecting the RF coil assembly having a least one latch configured to secure at least one position of the RF coil assembly, and securing or releasing the RF coil assembly.

According to another embodiment of the present invention, a method as defined above is disclosed, additionally comprising a step of reversibly detaching the RF coil from the cradle.

According to another embodiment of the present invention, a method as defined above is disclosed, additionally comprising a step of selecting the RF coil configured to connect to at least a second RF coil, and connecting at least a second RF coil.

According to another embodiment of the present invention, a method as defined above is disclosed, additionally comprising a step of selecting the RF coil connected to at least a second RF coil by a maneuverable connection, and maneuvering the RF coil relative to at least a second RF coil.

According to another embodiment of the present invention, a method as defined above is disclosed, additionally comprising a step of selecting the RF coil of which at least a portion of is integrated into MRI-safe material.

According to another embodiment of the present invention, a method as defined above is disclosed, additionally comprising a step of supporting the cradle in connection with an RF coil assembly by a cart.

According to another embodiment of the present invention, a method as defined above is disclosed, additionally comprising a step of selecting the cart in which at least a portion of is made of MRI safe material.

According to another embodiment of the present invention, a method as defined above is disclosed, additionally comprising a step of selecting the cart in which at least a portion of is insertable to a selected from a group consisting of: into an MRD bore, into a transport device, into a treatment device, into a storage device, and any combination thereof.

According to another embodiment of the present invention, a method as defined above is disclosed, additionally comprising a step of selecting the cart having means for maneuvering the cradle providing movement selected from a group consisting of: rotational, tilt, vertical shift, horizontal shift, and any combination thereof, and maneuvering the cradle.

According to another embodiment of the present invention, a method as defined above is disclosed, additionally comprising a step of selecting the RF assembly, in connection with the cradle and the cart configured to be at least partially insertable into an MRD bore.

According to another embodiment of the present invention, a method as defined above is disclosed, additionally comprising a step of selecting the RF assembly and cradle are sized and shaped to be accommodated within an MRD bore.

According to another embodiment of the present invention, a method as defined above is disclosed, additionally comprising a step of selecting the RF coil assembly having a hinge mechanism, thereby enabling maneuvering of the RF coil in an axis perpendicular to the linearly reciprocating axis.

According to another embodiment of the present invention, a method as defined above is disclosed, additionally comprising a step of selecting the RF coil assembly having a plurality of RF coils.

According to another embodiment of the present invention, a method as defined above is disclosed, additionally comprising a step of transmitting, receiving, or both with the RF coil.

According to another embodiment of the present invention, a method as defined above is disclosed, additionally comprising a step of selecting the RF coil from a group consisting of: solenoid, planar, volume, surface, quadrature, and any combination thereof.

According to another embodiment of the present invention, a method as defined above is disclosed, additionally comprising a step of selecting the RF coil configured to be a multiply tuned RF coil.

According to another embodiment of the present invention, a method as defined above is disclosed, additionally comprising a step of selecting the RF coil assembly having a multi-channel RF coil transceiver and a multi-channel RF coil, and reconfiguring the RF coil system between pluralities of operational modes.

According to another embodiment of the present invention, a method as defined above is disclosed, additionally comprising a step of parallel imaging.

According to another embodiment of the present invention, a method as defined above is disclosed, additionally comprising a step of selecting the RF coil assembly comprising at least one shim coil.

According to another embodiment of the present invention, a method as defined above is disclosed, additionally comprising a step of selecting the maneuvering mechanism is configured to accept different RF coil assemblies as modular pieces, and connecting at least one modular RF coil assembly. Additionally or alternatively, the RF coil is a multiply tuned RF coil thereby enabling parallel imaging.

According to another embodiment of the present invention, a method as defined above is disclosed, additionally comprising a step of parallel imaging.

According to another embodiment of the present invention, a method as defined above is disclosed, additionally comprising a step of selecting the RF coil assembly comprising at least one shim coil.

According to another embodiment of the present invention, a method as defined above is disclosed, additionally comprising a step of selecting the maneuverable mechanism configured to accept more than one RF coil assembly, and maneuvering the assemblies in a manner selected from a group consisting of: all together, each separately, one following the other, maintaining a predetermined spatial interaction between the assemblies, coordinated movement configured to best fit neonate, movement configured to respond to feedback from MR signal received of the neonate, and any combination thereof.

Reference is now made to FIG. 1 schematically illustrating, in an out of scale manner, an embodiment of the invention. A side view of an MRI-compatible neonate's cradle (200) according to one embodiment of the invention, having a maneuverable RF coil assembly (100) in its CLOSE configuration, i.e., within-the-MRI configuration, namely an arrangement where the coil assembly covers the infant's face or head, or body (e.g., infant's chest, hand, leg etc.). The infant is immobilized to his cradle's or his tray (101) by means of immobilization suite such as a hugger, straps, harness, an ergonomic placement, etc., thereof.

The cradle disclosed here comprise, in one of its embodiments, a plurality (namely one or more) maneuverable flaps (105) which provides the cradle with a non-capsulated (de-encapsulated) or non-enveloped configuration, were the neonate is laying on his/her support (105) providing free access to the neonate; and an capsulated (encapsulated), enveloped configuration where the neonate's environment is an incubator's controlled environment, effectively isolated/barriered from the ambient (room's- or MRI's-) environment. Additionally or alternatively, the neonate resides in a cradle enveloped as an incubator and closed to the external environment by the RF coil assembly, when in at least one configuration.

In one embodiment of the invention, at least a portion of the cradle is made of a at least a portion of a material such as an MRI safe material, a sterilizable material, a transparent material, an MRI permeable material, a fire retardant material and etc.

The RF coil assembly (100) is maneuverable, in at least two movement vectors, a linear motion and a circular motion. The linear motion can be a reciprocating reversible movement of the RF coil assembly enabled by a maneuverable mechanism such as a sliding mechanism, wheels on/in a track, wire guided, telescopic arms, and etc., as non-limiting examples. The second movement can be an oscillating or rotary movement, in a vector in a plurality of angles relative to the cradle, or specifically as a non-limiting example in a 90 degree vertical angle to the first linear movement vector. Additionally or alternatively this movement is reversible. According to an embodiment of the invention the RF coil is maneuverable by means such as a lever, handle, bar, knob, switch, applicator, etc., (150). The handle, lever, or applicator is fitted for the handler's hands (60). The maneuver is provided manually, automatically or semi-automatically, mechanically, hydraulically, oil pressure system, electrically powered, telescopic mechanism, or in a combination thereof.

The maneuvers are provided by various means, such as by sliding mechanism (tracks, paths, grooves, train-like tracks etc.), rotation mechanism (oscillating, tilting, and providing a screw-like motion and the like, around a pivot point, turning on a hinge, folding around a hinge, collapsing mechanism (folding, plaiting, plication, replication; folding, corrugation, jointing, articulation etc.). The maneuver can be applicable also by remote control. The linear reciprocation in one step and tilting motion in second step as defined herein and after are one embodiment which is presented as an example of providing a maneuverable RF coil mechanism disclosed and claimed in the present invention.

Maneuvering the RF coil (100) is of at least two steps. The linear reciprocation in one step and tilting motion in second step as defined herein and after are one embodiment which is presented as an example of providing a maneuverable RF coil mechanism disclosed and claimed in the present invention.

Additionally or alternatively, the RF coil assembly is configured to enable a set of reciprocal consequential maneuvers. This will enable fine tuning the position of the RF coil in reference to a best imaging result obtainable in each specific case/patient.

Additionally or alternatively, the RF coil is configure to at least partially surround at least a portion of the neonate.

Additionally or alternatively the RF coil assembly comprises a system of at least one sensor and at least one indicator configured to sense and indicate such as the configuration of the RF coil assembly, the proximity of RF coil assembly to the neonate's head, the structural integrity of RF coil assembly, and etc.

Reference is now made to FIG. 2A schematically illustrating, in an out of scale manner, an embodiment of the invention. A rear perspective view of the RF coil assembly (100) when in a CLOSE CONFIGURATION, having the RF coil close to the neonate's head. Also presented is an embodiment of a handle (150) useful for maneuvering the RF coil assembly by a handler.

Reference is now made to FIG. 2B schematically illustrating in an out of scale manner, an embodiment of the invention. A rear schematic view showing when in a CLOSE CONFIGURATION, meaning the RF coil is in a position near the neonate's head. The RF coil assembly has a protrusion (108) situated between rails or tracks of the neonate's cradle on either side (107). Additionally or alternatively, the tracks or rails can be at least partially be connected to a portion of an MRI-safe cart, an MRD, a cradle/incubator, or any combination thereof. Additionally or alternatively, the tracks, rails or sliding mechanism can be reversibly detachable from the place it is installed (e. g. the cradle, cart, etc.)

Reference is now made to FIG. 2C schematically illustrating, in an out of scale manner, an embodiment of the invention. A rear view of the RF coil assembly (100), having the RF coil away from the neonate's head, and after being tilted or turned upside-down below the cradle. The RF coil assembly has a protrusion (108) situated between rails or tracks of the neonate's cradle on either side (107). Additionally or alternatively, the sliding mechanism is at least partly embedded within the cradle or cart. Further, in yet another embodiment of the invention, the RF coil assembly can be at least partially embedded in a designated location below or aside of the neonate within the cradle or cart when in a position away from the neonate.

Reference is now made to FIG. 3A-G schematically illustrating, in an out of scale manner, an embodiment of an implementation of a method of the present invention. The linear reciprocal and rotation motions, as presented in FIG. 3, exemplify one of embodiments of the present invention; the rotation or tilting motion in the following description is by non-limiting example performed to the left. Additionally or alternatively, the rotation is clockwise or anti clockwise. A method of magnetic resonance imaging of a neonate or a patient that includes placing the neonate in a cradle, this step can further include connecting the neonate to life supporting equipment or in an embodiment the neonate is moved to the cradle still connected to the same life support equipment that he had in his prior position and only the tubing and wiring are transfer to the current position within the cradle. Further, maintaining the position of the neonate by embracing him with constraint means, and connecting the neonate to life supporting equipment if needed. Then, tilting the RF assembly from a position away from the patient neonate to an angle parallel to the tray on which the neonate resides, and to a right-side up position. Then linearly reciprocating the RF coil assembly towards the neonate's head. Following inserting the neonate within the cradle having an RF coil assembly into an MRI bore and imaging. When imaging is concluded, the RF coil assembly can be retracted linearly away from the neonate and then turned around a pivot point placed in the axes of the tray on which the neonate resides. This allows for easy access to the neonate head and to the life support equipment and monitoring equipment that are connected to him/her. In another embodiment the RF coil assembly is maneuvered to be in proximity to any portion of the neonate's body. In an embodiment the RF coil assembly can be comprised of multiple pieces interconnected therebetween. The RF coil assembly can be comprised of a plurality of RF coils.

Figure 3A:
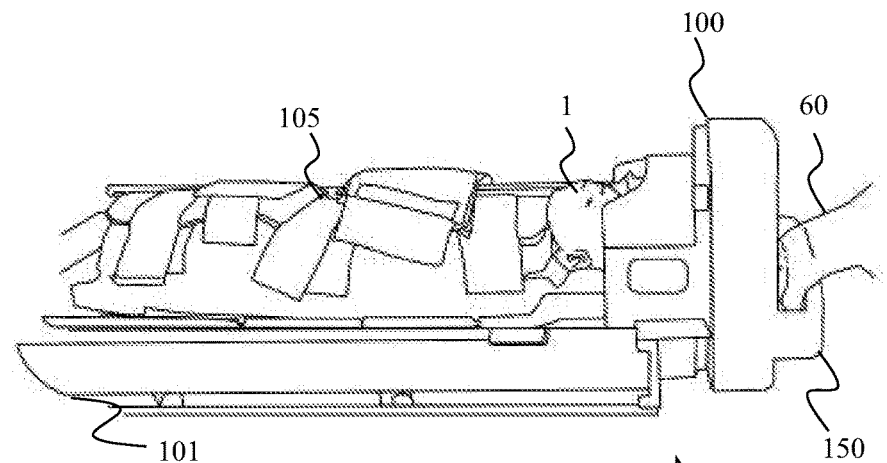
FIG. 3A is a schematic illustration of an installable RF coil, in a perspective view, showing in a non-limiting manner the RF coil maneuvered by a handler.

Reference is now made to FIG. 3A schematically illustrating, in an out of scale manner, an embodiment of the invention. A neonate's cradle (101) and an installable RF coil assembly (100) shown accommodating a neonate (1). Further the neonate is held in position with multiple straps (105). The maneuverable RF coil assembly (100) is shown in a partially CLOSE CONFIGURATION having the RF coil near the neonate's head (1), and partially in its OPEN configuration, namely when the RF coil is retracted, pulled or otherwise maneuvered such that RF coil only partially cover the infant's face (1), additionally or alternatively covering at least a portion of the neonates' head. The RF coil assembly comprises means for maneuvering the RF coil, such as a handle (150). The handler's hand (60) is pulling the handle (150) in the direction indicated by the arrow (10) to achieve a linear motion of the RF coil, the linear motion could also be reciprocated contrariwise.

Figure 3B:
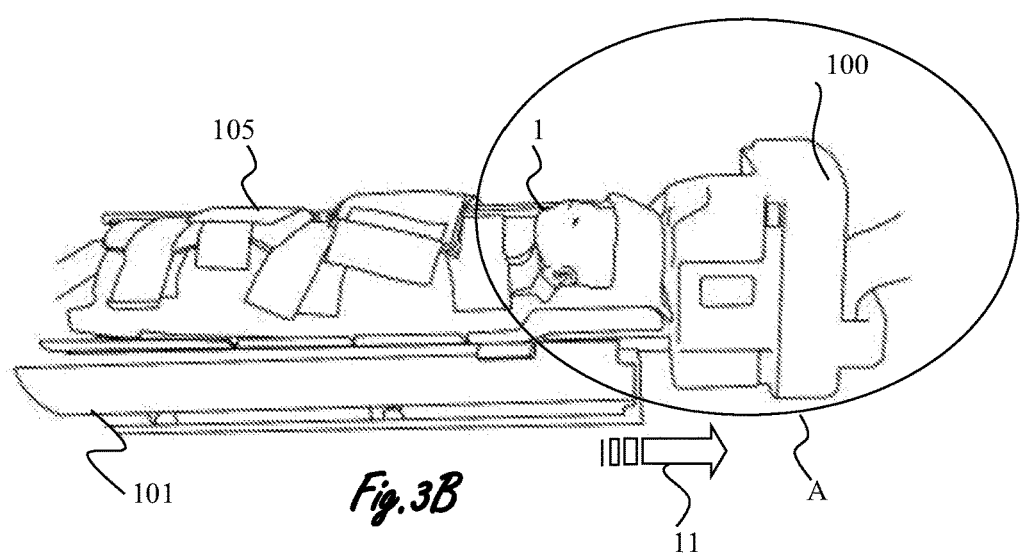
FIG. 3B is a schematic illustration of an installable RF coil, in a perspective view, showing in a non-limiting manner the RF coil maneuvered by a handler.

Reference is now made to FIG. 3B schematically illustrating, in an out of scale manner, an embodiment of the invention. A neonate's cradle (101) and an installable RF coil assembly (100) shown accommodating a neonate (1). The neonate is held in position with multiple straps (105). The RF coil assembly (100) is shown having the RF coil away from the neonate's head (1) following a linear motion in the direction signified by the arrow (11). The RF coil assembly comprises means for maneuvering the RF coil, such as a handle, configured for enabling a manual movement, a preconfigured automated movement triggered by the handler, a remote control movement, a movement triggered by entering a magnetic resonance device, an adjustment movement for fine tuning the signal transmitted or received, and etc. The handler's hand (60) is pulling the handle (105) in the direction indicated by the arrow (11) achieving a linear motion of the RF coil. The RF coil is being retracted along the cradle.

Figure 3C:
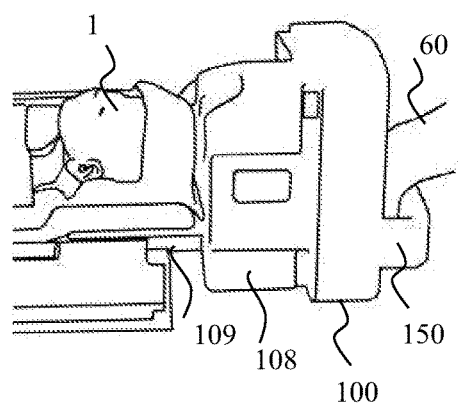
FIG. 3C is a schematic illustration of an installable RF coil, showing a part of FIG. 3B presented by circle A.

Reference is now made to FIG. 3C schematically illustrating, in an out of scale manner, an embodiment of the invention. This figure is an enlargement of the encircled portion 'A' in FIG. 3B. An RF coil assembly shown in a configuration following a linear movement away from the neonate's head, as indicated by the arrow (11). The neonate (1) remains constrained in the same position in the cradle (101), while the installable RF coil is being maneuvered. In this configuration the RF coil assembly protrusion (108), configured to be situated between rails or tracks of the cradle. In this embodiment the RF coil assembly is rotatable or tiltable along a shaft (109), providing a second step maneuvering of the RF coil assembly. The handler represented by a hand (60) is pulling the handle (150) of the Installable RF coil.

Figure 3D:
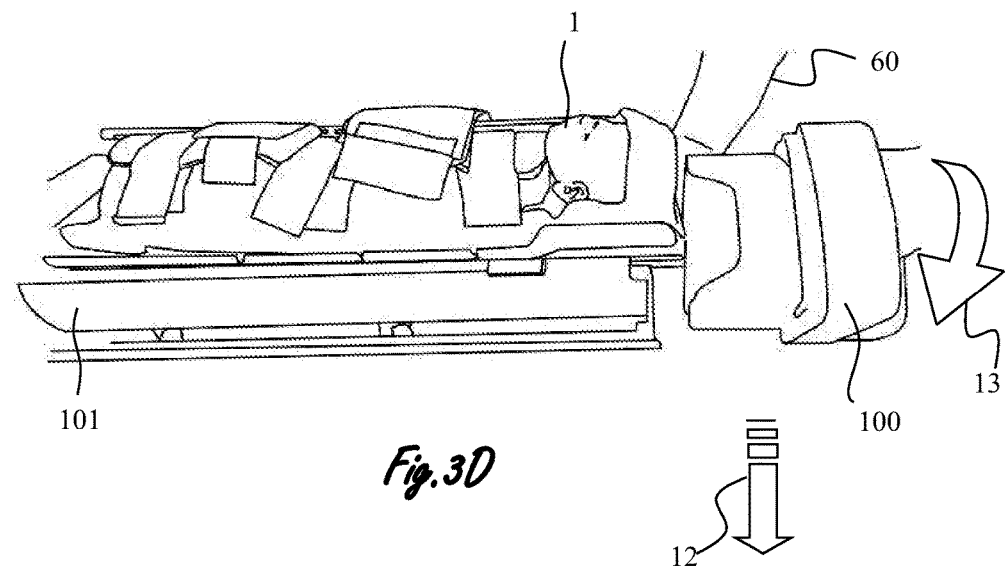
FIG. 3D is a schematic illustration of an installable RF coil, in a perspective view, showing in a non-limiting manner the RF coil maneuvered by a handler.

Reference is now made to FIG. 3D schematically illustrating in an out of scale manner an embodiment of the invention. Exemplified is the second maneuver of the RF coil assembly (100), tilting in reference to a pivot point along an axis parallel to the ground or cradle, or rotating along the axis parallel to the cradle, in a general downward direction away from the neonate (arrow 12). In a non-limiting manner, one embodiment the tilting is in direction of the arrow (13), and can be alternatively or additionally be clock wise, anti-clockwise, having a smooth motion or a resistant motion along steps. This is done by the handler represented by the handler's hand (60). The neonate (1) remains in position although the RF coil is being maneuvered.

Figure 3E:
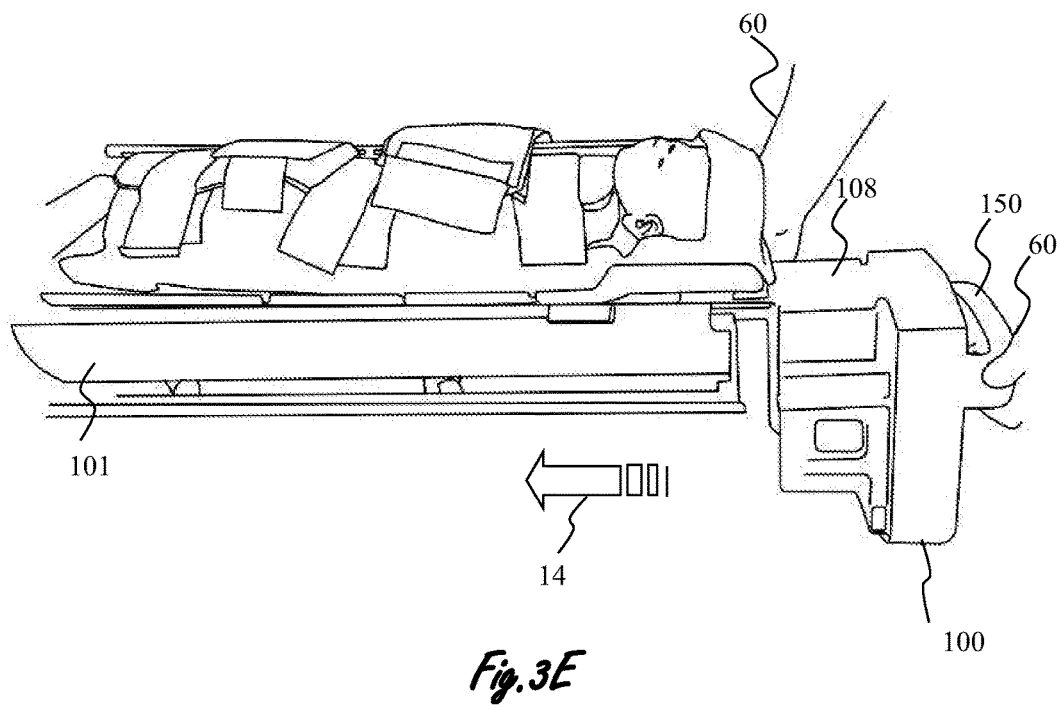
FIG. 3E is a schematic illustration of an installable RF coil, in a perspective view, showing in a non-limiting manner the RF coil maneuvered by a handler.

Reference is now made to FIG. 3E schematically illustrating in an out of scale manner an embodiment of the invention. Exemplified is the consequence of the second maneuver of the RF coil assembly (100), after being rotated along the axis parallel to the cradle or parallel to the ground, in a general downward direction away from the neonate, it now resides in an upside-down position with the majority of the RF coil below the cradle. The RF coil assembly is in its OPEN (partially tilted) configuration, i.e., out-of-the-MRI configuration, namely when the RF coil is retracted, pulled or otherwise maneuvered such that RF coil does not cover the infant's face. The protrusion (108) insertable in a track or recess in the cradle is extracted and rotated to 180 degrees. The following maneuver is moving the RF coil assembly under the cradle in the direction indicated by the arrow (14).

Figure 3F:
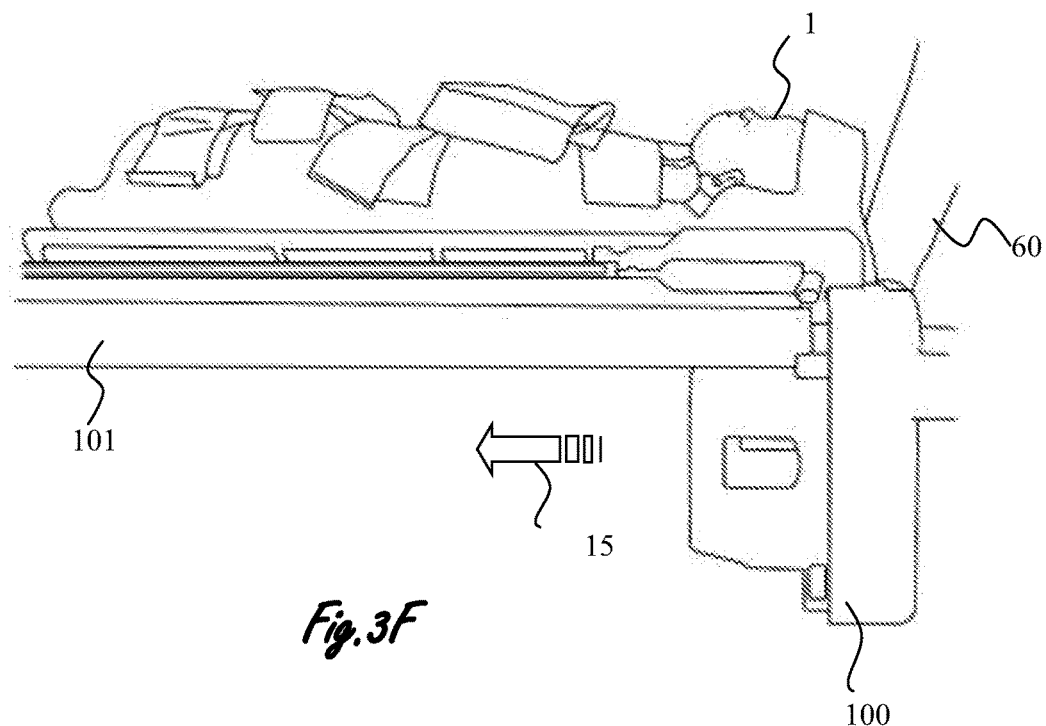
FIG. 3F is a schematic illustration of an installable RF coil, in a perspective view, showing in a non-limiting manner the RF coil maneuvered by a handler.

Reference is now made to FIG. 3F schematically illustrating in an out of scale manner an embodiment of the invention. Exemplified is the RF coil assembly (100) inserted into a position away from the neonate, below the cradle in an upside-down formation. The maneuverable RF coil assembly (100) is in its OPEN (totally tilted) configuration, i.e., out-of-the-MRI configuration, arranged in a manner that it does not disturb medical personal treating the infants immobilized in his cradle.

Figure 3G:
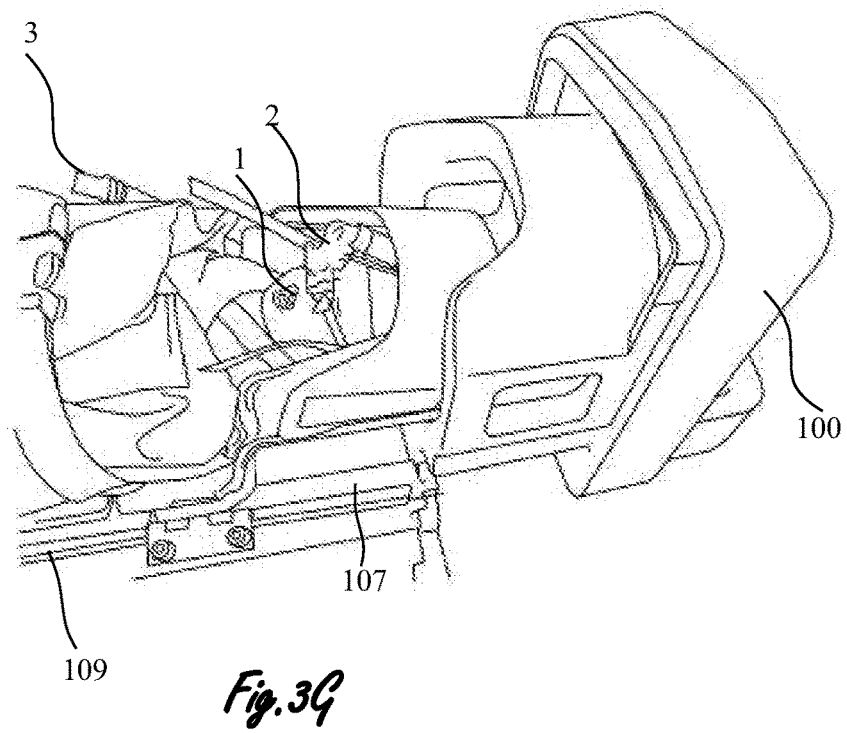
FIG. 3G is a schematic illustration of an installable RF coil, in a perspective view, showing in a non-limiting manner a neonate accommodated in the cradle connected to life support equipment.

Reference is now made to FIG. 3G schematically illustrating, in an out of scale manner, an embodiment of the invention. In this embodiment the cradle (101) and installable RF coil arrangement (100) are provided with life supporting equipment for the neonate (1) such as a breathing mask (2), a respirator, medical equipment tubing (3), a sensor, an indicator, environmental control means such as humidifier, temperature regulating means, ventilating means, etc.

Figure 4A:
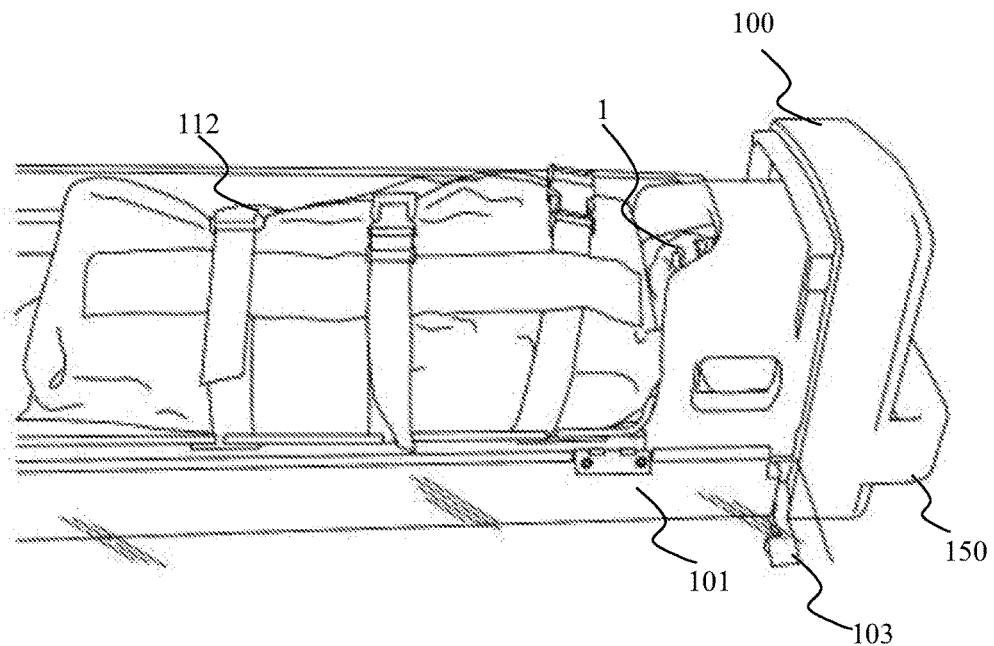
FIG. 4A is a schematic illustration of a cradle accommodated by a neonate, with an installable RF coil having a latching mechanism.

Reference is now being made to FIG. 4A schematically illustrating, in an out of scale manner, an embodiment of the invention. The RF coil is presented in a CLOSE CONFIGURATION partially covering the neonate's head. Further the neonate is shown encapsulated and held with straps or movable flaps to a specific position. In this embodiment the assembly comprises a lock or latch (103) to secure the position of the installable RF coil. The secured position can be any location the RF coil assembly can be maneuvered into, and specifically for example when the RF coil is in the CLOSE CONFIGURATION, or when the RF coil assembly is positioned away from the neonate, below the cradle. The latch (103) is switched to secure the RF coil fixation so that it is temporarily not maneuverable; the assembly is now ready to be moveable or inserted into an MRD, such as a closed-bore or open bore MRI device. The latch can be further utilized to release the locked position of the RF coil, allowing for maneuvering of the RF coil.

Figure 4B:
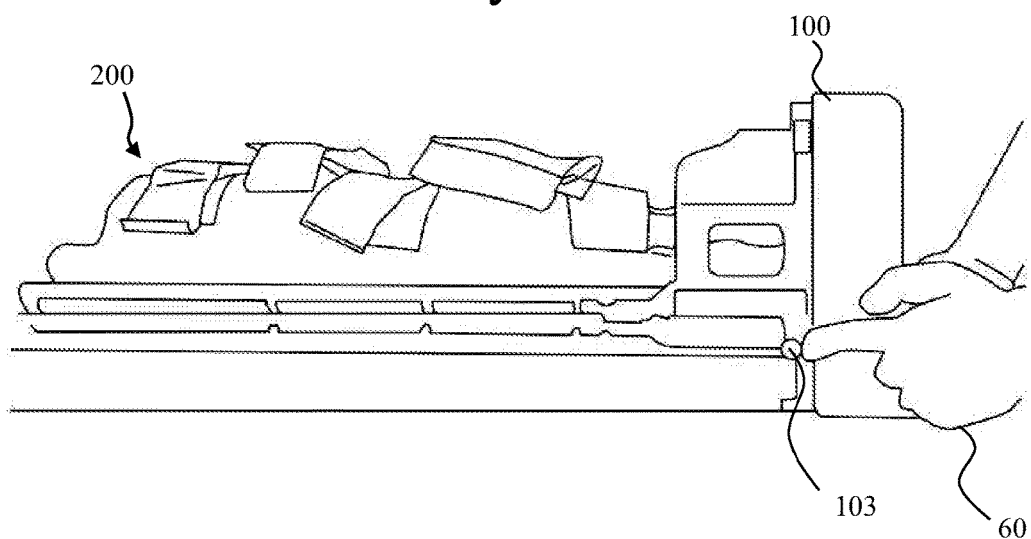
FIG. 4B is a schematic illustration of a cradle with an installable RF coil having a latching mechanism.

Reference is now being made to FIG. 4B schematically illustrating, in an out of scale manner, an embodiment of the invention. Illustrated is a side view of an MRI-compatible neonate's cradle according to the embodiment of the invention, wherein maneuverable RF coil assembly (100) is in its CLOSE configuration, configuration, and incubator/cradle movable flaps (105) are turned OFF or straps disconnected, so a neonate could be either inserted or released from the cradle. The MRI compatible cradle is shown without a neonate. Further the latch (103) is not secured so that the RF coil is temporarily mobile.

Figure 5:
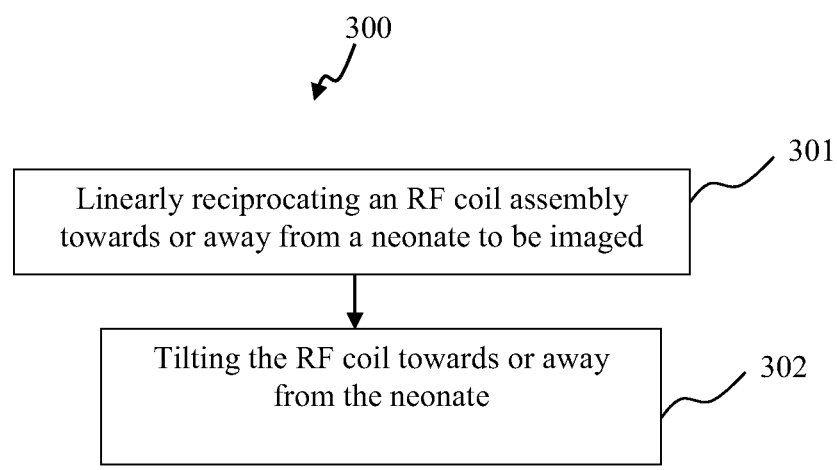
FIG. 5 is a schematic diagram of a method for applying at least one RF coil over a neonate in a cradle, and removing the coil when not required.

Reference is now made to FIG. 5 schematically illustrating a flow diagram describing a method of the invention (300). Described is a method for both (i) applying at least one RF coil, at least partially over a neonate immobilized within his/her cradle and (ii) conveniently removing the RF coil from the neonate and safely placing it when it is not required for imaging. The method comprises at least two different steps of maneuvering an RF coil. The first step (301) is linearly reciprocate an RF coil assembly, thereby approaching or otherwise drawing away at least one coil to and from a neonate to be MR imaged. The second step (302) is tilting/turning/pivoting/bending/shifting/angling/reclining the RF coil assembly for placing at least one coil away from the neonate when the neonate is not MR imaged. Additionally or alternatively, at least the second step comprises a maneuvering of the RF coil in a vector different from the vector maneuvered in the first step.

Additionally or alternatively, the method disclosed above additionally comprises a plurality of consequential maneuvering steps, each step applying a different movement vector of the RF coil, relative to the neonate or cradle.

According to another embodiment of the present invention, a method as defined above is disclosed, additionally comprising at least one of the following steps: (a) selecting the assembly to be sized and shaped to fit over at least a portion of the neonate; (b) selecting the assembly is sized and shaped to accommodate at least a portion of the neonate; or (c) connecting the cradle to the RF coil by a maneuverable mechanism thereby enabling the RF coil to be positioned in a plurality of positions adjacent to the neonate.

According to another embodiment of the present invention, a method as defined above is disclosed, additionally comprising a step of selecting the cradle having an emergency release mechanism, and configuring the mechanism to immediately release the neonate from the cradle when in need.

According to another embodiment of the present invention, a method as defined above is disclosed, additionally comprising a step of selecting the RF coil having an emergency release mechanism, and configuring the mechanism for immediately releasing the RF coil from the cradle.

According to another embodiment of the present invention, a method as defined above is disclosed, additionally comprising a step of connecting neonate life support equipment to the cradle, the neonate or both.

According to another embodiment of the present invention, a method as defined above is disclosed, additionally comprising a step of selecting the cradle having means for maintaining the position of the neonate and utilizing the means for maintaining the body position of the neonate.

According to another embodiment of the present invention, a method as defined above is disclosed, additionally comprising a step of selecting the cradle having an envelope surrounding an internal environment in which the neonate is accommodated.

According to another embodiment of the present invention, a method as defined above is disclosed, additionally comprising a step of selecting the maneuverable mechanism configured to allow movement of the RF coil assembly within the internal environment, external to the internal environment or both.

According to another embodiment of the present invention, a method as defined above is disclosed, additionally comprising a step of moving the RF coil assembly within the internal environment, external to the internal environment or both.

According to another embodiment of the present invention, a method as defined above is disclosed, additionally comprising a step of selecting the RF coil configured to have at least one position forming a close environment incubator.

According to another embodiment of the present invention, a method as defined above is disclosed, additionally comprising a step of selecting the cradle from a group consisting of: an incubator, a deployed incubator, a transport incubator, a treatment table, a countertop, an operating table, a bed, a baby cradle, a basket, a mattress, a stretcher, a gurney, and any combination thereof.

According to another embodiment of the present invention, a method as defined above is disclosed, additionally comprising a step of selecting the RF coil configured for closing an opening of an incubator when in at least one position.

According to another embodiment of the present invention, a method as defined above is disclosed, additionally comprising a step of selecting the cradle having a selected from a group consisting of: at least one sensor, at least one indicator, at least one medical equipment tubing placement, at least one opening fitted for the insertion of a handlers hand, at least one opening for the passage of life supporting equipment, and any combination thereof.

According to another embodiment of the present invention, a method as defined above is disclosed, additionally comprising a step of selecting the cradle having a user interface configured for monitoring or controlling a selected from a group consisting of: life supporting equipment, MRI operation, position of RF coil, RF coil maneuvering mechanism, opening or closing the cradle, and any combination thereof.

According to another embodiment of the present invention, a method as defined above is disclosed, additionally comprising at least one of the following steps: (a) monitoring a selected from a group consisting of: life supporting equipment, MRI operation, position of RF coil, RF coil maneuvering mechanism, opening or closing the cradle, and any combination thereof; or, (b) controlling a selected from a group consisting of: life supporting equipment, MRI operation, position of RF coil, RF coil maneuvering mechanism, opening or closing the cradle, and any combination thereof.

According to another embodiment of the present invention, a method as defined above is disclosed, additionally comprising a step of selecting the RF coil assembly having at least one sensor configured to sense a selected from a group consisting of: structural integrity of the RF coil, structural integrity of the maneuvering mechanism, position of RF coil, proximity of the neonate to the coil, RF signal received, RF signal transmitted, and any combination thereof.

According to another embodiment of the present invention, a method as defined above is disclosed, additionally comprising a step of selecting the sensor connected to at least one indicator, and receiving an indication from the sensor.

According to another embodiment of the present invention, a method as defined above is disclosed, additionally comprising a step of selecting the assembly having a handle configured for operation by a handler, and maneuvering the handle, thereby maneuvering a selected from a group consisting of: the RF coil, the cradle, neonate restraining means, neonate mattress, a cart connected to the cradle, and any combination thereof.

According to another embodiment of the present invention, a method as defined above is disclosed, additionally comprising a step of selecting the maneuvering mechanism from a group consisting of: automated, manual, semi-automated, remote controlled, and any combination thereof, and operating the mechanism.

According to another embodiment of the present invention, a method as defined above is disclosed, additionally comprising a step of selecting the maneuverable mechanism having maneuverable means selected from a group consisting of: sliding mechanism, pivot point mechanism, hinge, telescopic mechanism, hydraulic mechanism, turning mechanism, and any combination thereof.

According to another embodiment of the present invention, a method as defined above is disclosed, additionally comprising a step of selecting a cradle in connection with an RF assembly having at least a portion of the assembly and/or cradle are made of a material selected from a group consisting of: a MRI safe material, at least partially transparent material, a sterilizable material, a fire retardant material, and any combination thereof.

According to another embodiment of the present invention, a method as defined above is disclosed, additionally comprising a step of selecting the RF coil assembly having a least one latch configured to secure at least one position of the RF coil assembly, and securing or releasing the RF coil assembly.

According to another embodiment of the present invention, a method as defined above is disclosed, additionally comprising a step of reversibly detaching the RF coil from the cradle.

According to another embodiment of the present invention, a method as defined above is disclosed, additionally comprising a step of selecting the RF coil configured to connect to at least a second RF coil, and connecting at least a second RF coil.

According to another embodiment of the present invention, a method as defined above is disclosed, additionally comprising a step of selecting the RF coil connected to at least a second RF coil by a maneuverable connection, and maneuvering the RF coil relative to at least a second RF coil.

According to another embodiment of the present invention, a method as defined above is disclosed, additionally comprising a step of selecting the RF coil of which at least a portion of is integrated into MRI-safe material.

According to another embodiment of the present invention, a method as defined above is disclosed, additionally comprising a step of supporting the cradle in connection with an RF coil assembly by a cart.

According to another embodiment of the present invention, a method as defined above is disclosed, additionally comprising a step of selecting the cart in which at least a portion of is made of MRI safe material.

According to another embodiment of the present invention, a method as defined above is disclosed, additionally comprising a step of selecting the cart in which at least a portion of is insertable to a selected from a group consisting of: into an MRD bore, into a transport device, into a treatment device, into a storage device, and any combination thereof.

According to another embodiment of the present invention, a method as defined above is disclosed, additionally comprising a step of selecting the cart having means for maneuvering the cradle providing movement selected from a group consisting of: rotational, tilt, vertical shift, horizontal shift, and any combination thereof, and maneuvering the cradle.

According to another embodiment of the present invention, a method as defined above is disclosed, additionally comprising a step of selecting the RF assembly, in connection with the cradle and the cart configured to be at least partially insertable into an MRD bore.

According to another embodiment of the present invention, a method as defined above is disclosed, additionally comprising a step of selecting the RF assembly and cradle are sized and shaped to be accommodated within an MRD bore.

According to another embodiment of the present invention, a method as defined above is disclosed, additionally comprising a step of selecting the RF coil assembly having a hinge mechanism, thereby enabling maneuvering of the RF coil in an axis perpendicular to the linearly reciprocating axis.

According to another embodiment of the present invention, a method as defined above is disclosed, additionally comprising a step of selecting the RF coil assembly having a plurality of RF coils.

According to another embodiment of the present invention, a method as defined above is disclosed, additionally comprising a step of transmitting, receiving, or both with the RF coil.

According to another embodiment of the present invention, a method as defined above is disclosed, additionally comprising a step of selecting the RF coil from a group consisting of: solenoid, planar, volume, surface, quadrature, and any combination thereof.

According to another embodiment of the present invention, a method as defined above is disclosed, additionally comprising a step of selecting the RF coil configured to be a multiply tuned RF coil.

According to another embodiment of the present invention, a method as defined above is disclosed, additionally comprising a step of selecting the RF coil assembly having a multi-channel RF coil transceiver and a multi-channel RF coil, and reconfiguring the RF coil system between pluralities of operational modes. Additionally or alternatively, the RF coil is a multiply tuned RF coil thereby enabling parallel imaging.

According to another embodiment of the present invention, a method as defined above is disclosed, additionally comprising a step of selecting the maneuvering mechanism is configured to accept different RF coil assemblies as modular pieces, and connecting at least one modular RF coil assembly.

According to another embodiment of the present invention, a method as defined above is disclosed, additionally comprising a step of selecting the maneuverable mechanism configured to accept more than one RF coil assembly, and maneuvering the assemblies in a manner selected from a group consisting of: all together, each separately, one following the other, maintaining a predetermined spatial interaction between the assemblies, coordinated movement configured to best fit neonate, movement configured to respond to feedback from MR signal received of the neonate, and any combination thereof.

Figure 6:
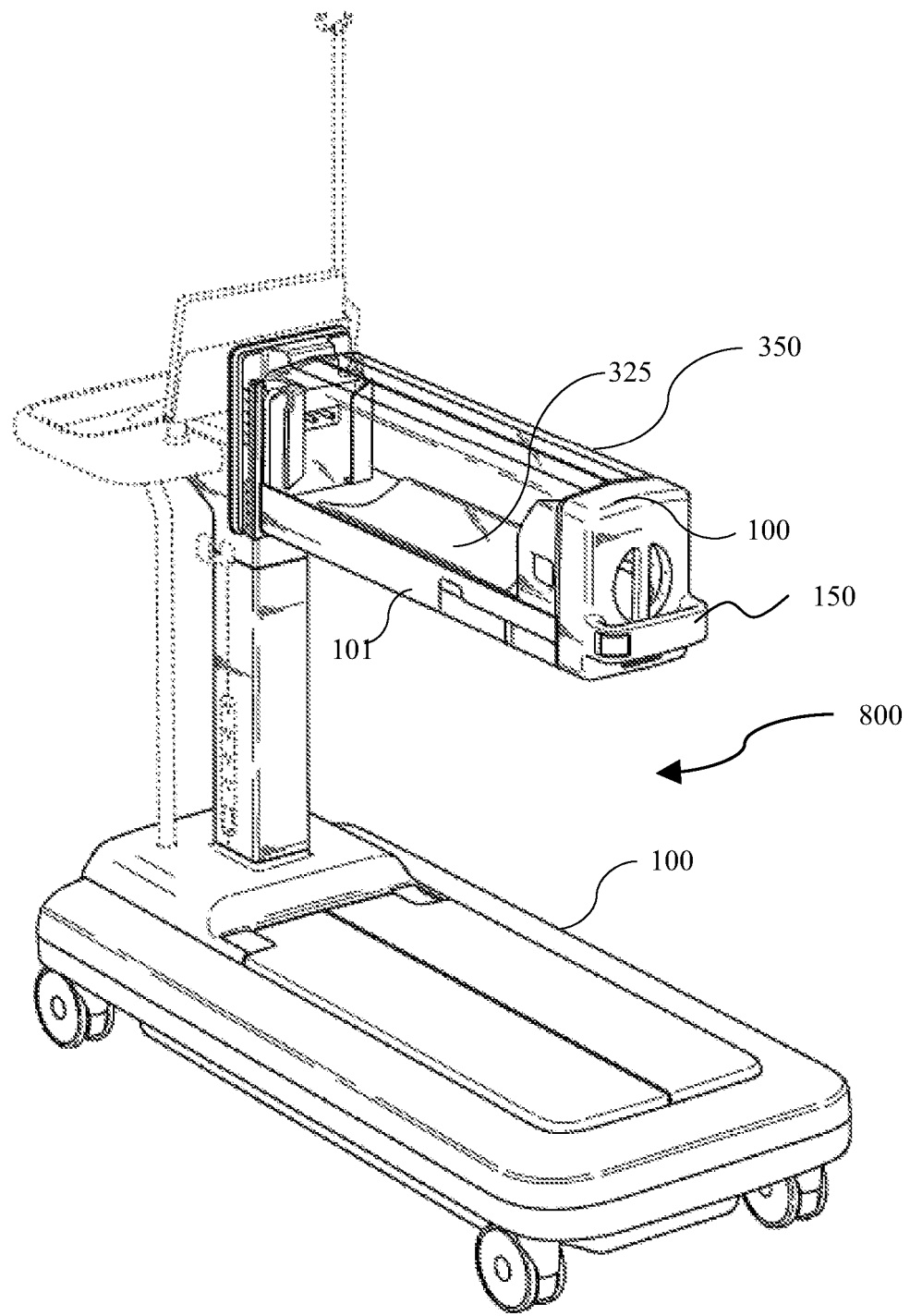
FIG. 6 is a schematic illustration of an MRI safe cart comprising an incubator having an installable RF coil assembly.

Reference is now being made to FIG. 6 schematically illustrating, in an out of scale manner, an embodiment of the invention. An assembly (800) of an RF coil (100) installable on an incubator (101) connected and supported by a cart (300). Illustrated is a cradle/incubator (101) assembly with a maneuverable, installable, RF coil (100), integrated into an MRI safe cart. In this embodiment the neonate is further encapsulated by a cover forming the incubator (350). The incubator is further provided with a mattress or neonate placement within (325), and connections and openings configured to allow the passage of life supporting equipment and/or the passage of a handlers hand. The incubator is connected to a mobile cart (300) by an interconnecting pillar. The installable RF coil (100) is equipped with a handle (150), and is functional as one of the incubators walls when in position proximal to the neonate's head. The cart with the incubator and the connected RF coil assembly are configured to be at least partly housed in an MRD bore. In this embodiment, the RF coil assembly closes the envelope (350) around the neonate's placement (325 to form a closed environment incubator. In this embodiment, the cart is mobile, allowing transport of the residing neonate straight into an MRD bore without having to disconnect him/her from life support equipment, and/or expose the neonate to the external environment.

Figure 7:
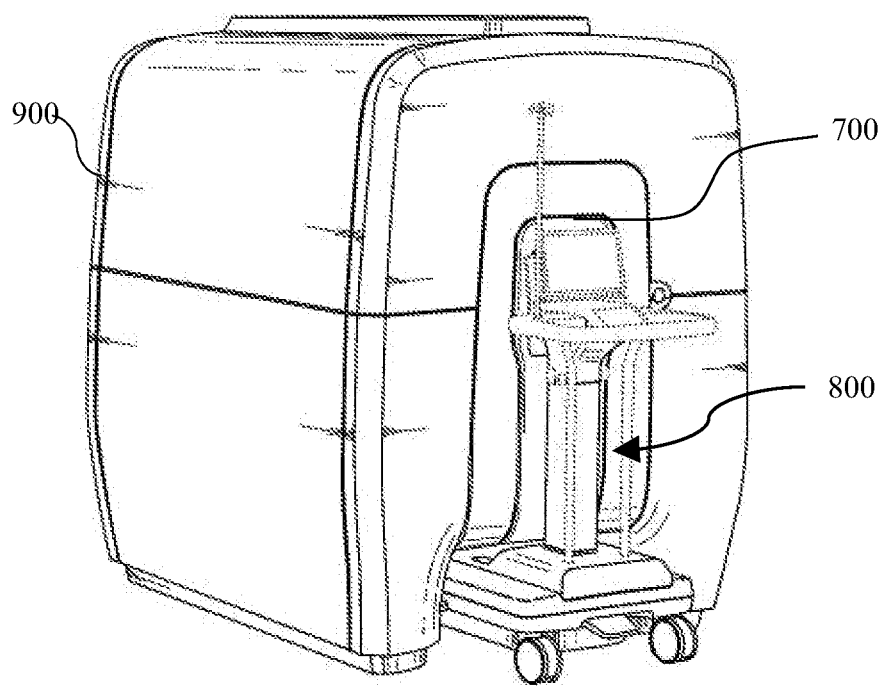
FIG. 7 is a schematic illustration of an MRD housing at least a portion of a cart accommodating a neonate and connected to an RF coil assembly.

Reference is now being made to FIG. 7 schematically illustrating, in an out of scale manner, an embodiment of the invention. Illustrated is a perspective view of an MRI system, comprising an MRD (900), having an open bore (700) such as the commercially available Aspect Imaging M2-type MRD. The assembly (800) of the cradle/incubator with an installable RF coil, containing the infant to be imaged, is supported by an MRI safe mobile cart, wherein the cart base (200) supporting the cradle is reversibly housed under the MRD, and the cradle/incubator, connected to an RF coil assembly is at least partially reversibly residing within the MRD bore (700).

Reference is now being made to FIG. 8A-E schematically illustrating in an out of scale manner, an embodiment of the invention. Illustrated is a perspective view of a neonate's cradle (101) with an installable RF coil assembly (100) that is maneuverable to at least two positions: over a neonate accommodated in a cradle and below or aside the cradle when it is not required for imaging. In reference to FIG. 8A, the RF coil assembly is maneuverable along a sliding mechanism (120) to be situated in any location above the neonate's body in the direction indicated by the arrow (A) and contrariwise. The sliding mechanism permits at least a linear movement along the neonate's body longitudinal axis, additionally or alternatively, provides movement along the track circling in a path leading under the cradle. Additionally or alternatively, the sliding mechanism (120) comprises a latching device configured for locking the position of the RF coil is the desired location. The cradle comprises means to confine the patient (e. g. neonate) such as a belt (112) having a buckle (113), or straps, hugger, restraint, etc. The cradle is only partly displayed, in a non-limiting manner, and can further be connected to a cart, an incubator, a treatment device, an imaging device, a patient bed, etc.

Figure 8A:
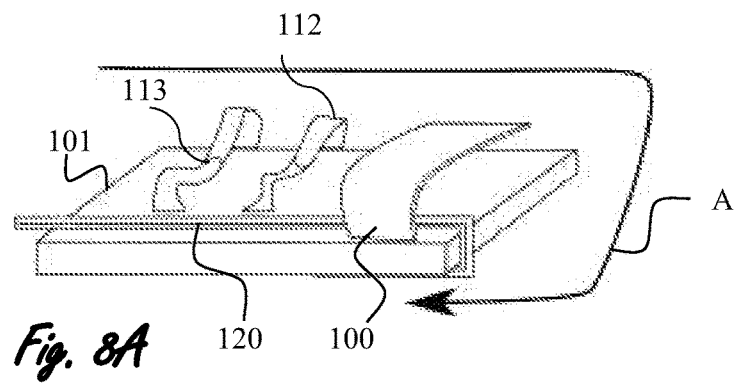
FIG. 8A is a schematic illustration of an installable RF coil assembly, in a perspective view, connected to a neonate's cradle showing the RF coil as being maneuverable along a sliding mechanism.
Figure 8B:
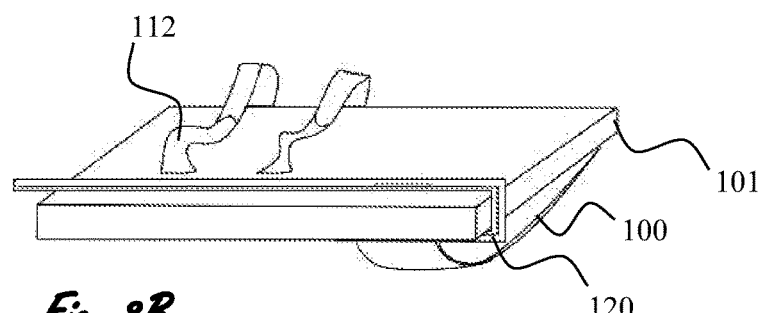
FIG. 8B is a schematic illustration of an installable RF coil assembly, in a perspective view, connected to a neonate's cradle showing the RF coil in a closed position below the neonate's cradle.

Reference is now being made to FIG. 8B schematically illustrating in an out of scale manner, an embodiment of the invention. Illustrated is a perspective view of a neonate's cradle (101) with an installable RF coil assembly (100) as embodied in FIG. 8A. The RF coil is presented in a position below the cradle, allowing direct access to a neonate positioned in the cradle from all sides. Further the neonate can be maintained in position by straps or belts (112). The RF coil can be further maneuvered along the sliding mechanism (120) back to a position on top the cradle (101).

Figure 8C:
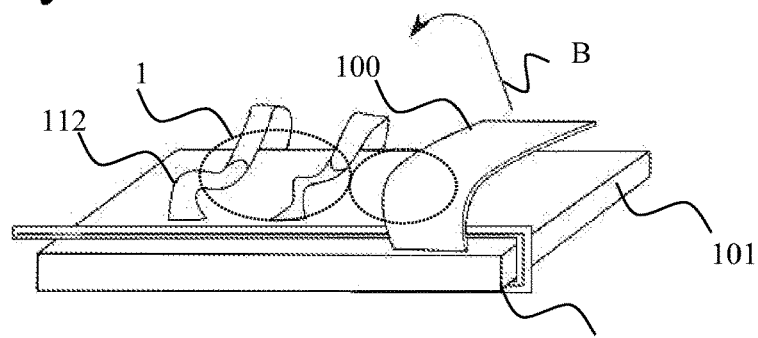
FIG. 8C is a schematic illustration of an installable RF coil assembly, in a perspective view, connected to a neonate's cradle showing the RF coil in a closed position proximate to a neonates head.

Reference is now being made to FIG. 8C schematically illustrating in an out of scale manner, an embodiment of the invention. Illustrated is a perspective view of a neonate's cradle (101) with an installable RF coil assembly (100). The RF coil is presented in a position at least partially above a neonate (1) positioned in the cradle and constrained in position by straps (112). The RF coil can be further maneuvered in the direction of the arrow (B) in a tilting motion opening and closing the RF coil in a proximal or distal position, aside position, relative to the neonate (1). The sliding mechanism (120) provides linear reciprocating movement to achieve position proximal and distal to the neonate, while the sliding mechanism further comprises a hinge mechanism (or a turning mechanism, a pivot point, tilting mechanism, etc.) enabling moving the RF coil assembly to a position beside the neonate, as embodied in FIG. 8D.

Figure 8D:
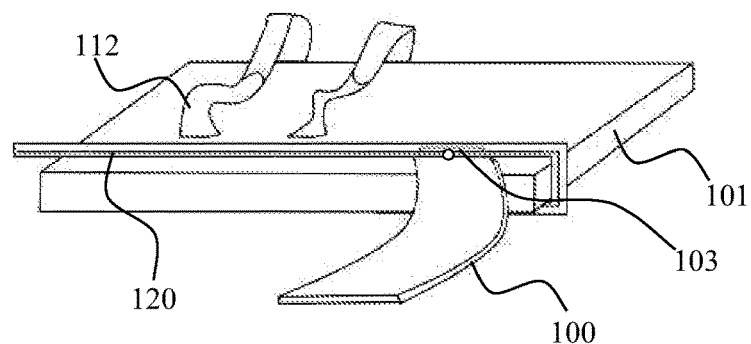
FIG. 8D is a schematic illustration of an installable RF coil assembly, in a perspective view, with two RF coil assemblies.

Reference is now being made to FIG. 8D schematically illustrating in an out of scale manner, an embodiment of the invention. Illustrated is a perspective view of a neonate's cradle (101) with an installable RF coil assembly (100). The RF coil is shown in an open position after being tilted, rotated, hinged, turned or maneuvered from a position proximal to the neonate portrayed in FIG. 8D to a position aside the neonate. In this illustration a maneuverable hinge (103) is displayed enabling the tilting movement.

Figure 8E:
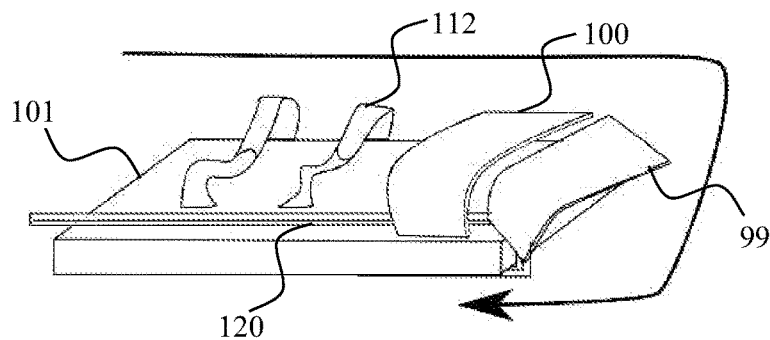

Reference is now being made to FIG. 8E schematically illustrating in an out of scale manner, an embodiment of the invention. Illustrated is a perspective view of a neonate's cradle (101) with two installable RF coil assemblies (100 and 99). The plurality of RF coil assemblies can be maneuvered along the track of the sliding mechanism (120) along the arrow, and also tilted to opened and closed positions.

Figure 9A:
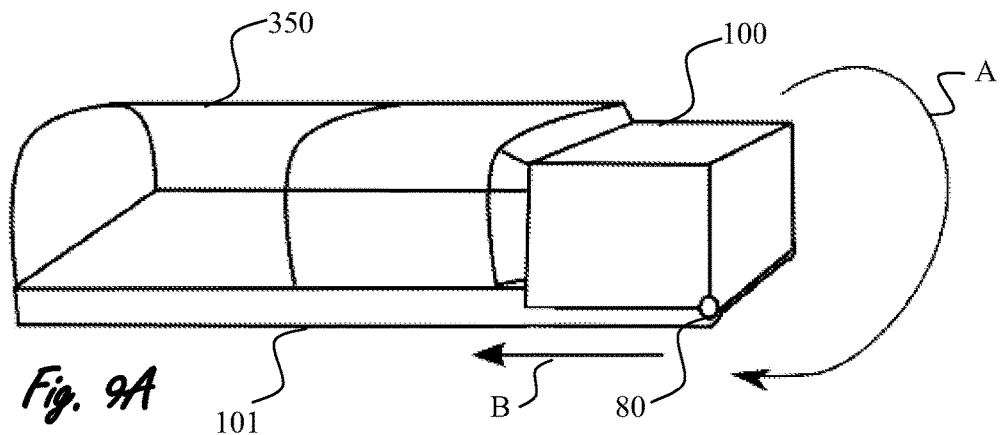
FIG. 9A is a schematic illustration of an installable RF coil assembly, in a perspective view, in closed position closing an internal environment for the neonate.
Figure 9B:
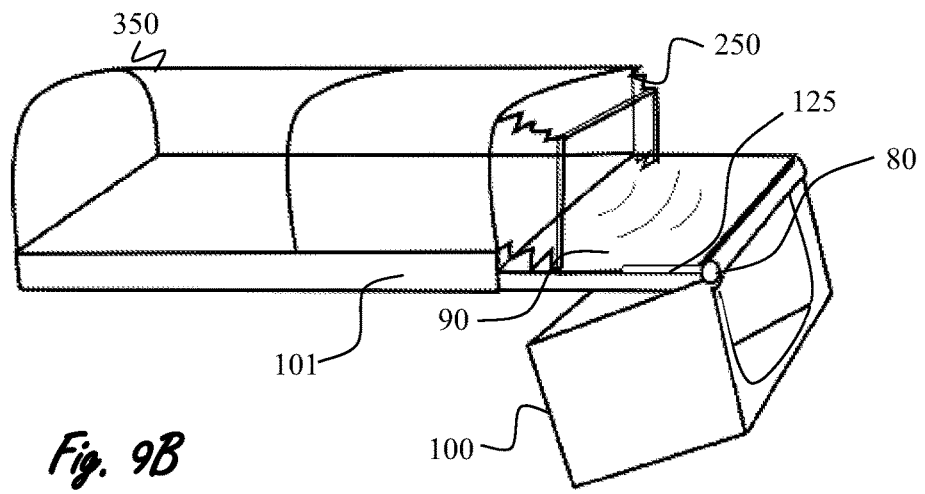
FIG. 9B is a schematic illustration of an installable RF coil assembly, in a perspective view, in an open position enabling access to the neonate's head.

Reference is now being made to FIG. 9A-B schematically illustrating in an out of scale manner, an embodiment of the invention. Illustrated is a perspective view of a neonate's cradle (101) with an installable RF coil assemblies (100) that is maneuverable to at least two positions: over a neonate accommodated in a cradle and below or aside the cradle when it is not required for imaging. The plurality of RF coil assemblies can be maneuvered along the track of the sliding mechanism (125) in a reciprocating linear motion along the arrow B and contrariwise, and in a tilting motion along the arrow (A), to a closed position at least partially over a neonates head as in FIG. 9A, or at least one open position as in FIG. 9B away from the neonate's head (e.g. below the cradle). The tilting motion is provided by the maneuverable connection (80), which can be such as a hinge, joint, flexible material, a pivot point mechanism, a turning mechanism, etc. When in a closed position, the RF coil assembly (100) closes an envelope (350) that is connected to the cradle (101), forming a closed environment incubator that is sized and shaped to accommodate a neonate. In FIG. 9B is illustrated a headrest for the neonate (90). This headrest can be for example ergonomic or have a concave shape to further support the head position of the neonate accommodated within. The connection (250) between the RF coil assembly (100) and the envelope (350) can be a of a flexible material such as nylon, plastic, rubber, fabric, polyester, an MRI-safe material, a transparent material, a sterilizable material, etc. or flexible construction such as an unfolding sheet, an accordion, a spring like construction, a spiral, etc. The flexible connection enables fine tuning of the location of the RF coil relative to the neonate's head while the closed environment incubator, formed when closing the RF coil assembly (100), is maintained. The entire apparatus comprised of an RF coil assembly, a cradle, and an envelope can be made of an MRI safe material, at least a partially transparent material, a sterilizable material, integrated with a fire retardant, a recyclable material, a disposable material, or any combination thereof.

Figure 10:
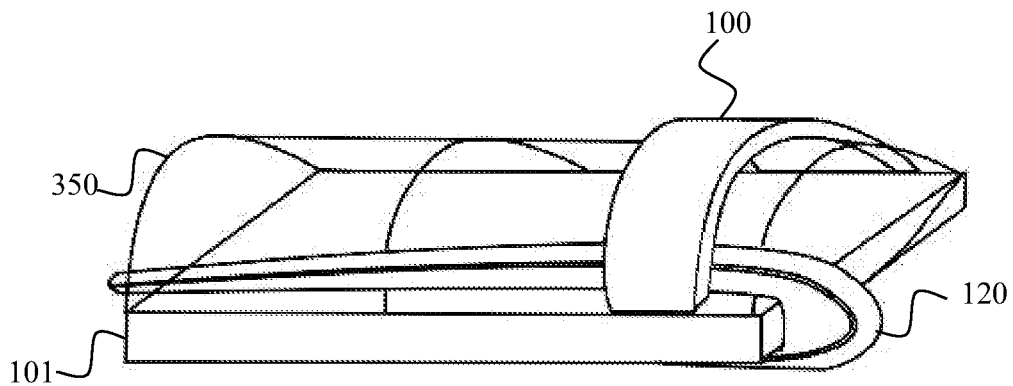
FIG. 10 is a schematic illustration of an installable RF coil assembly, in a perspective view. The RF coil is maneuverable external to an internal environment of an incubator.

Reference is now being made to FIG. 10 schematically illustrating in an out of scale manner, an embodiment of the invention. Illustrated is a perspective view of a neonate's cradle (101), connected to an envelope creating a closed environment incubator, with an installable RF coil assemblies (100) that is maneuverable to at least two positions: over a neonate accommodated in a cradle and below or aside the cradle when it is not required for imaging. The RF coil assembly is maneuverable along a sliding mechanism (120) along the longitudinal axis of the incubator and further flows the contour of the envelope and cradle around the side of the cradle to a location below the incubator. In this embodiment, the RF coil assembly (100) is an addition external to the incubator internal environment and is located on the external side of the envelope. This embodiment keeps the neonate secure within a sterile and monitored environment configured to a life supporting environment for the neonate (e.g. environment in which the temperature, humidity and gas concentration are regulated, life supporting equipment is connected and available for the neonate, etc.). The second movement vector is available through a hinge like connection providing closing and/or opening the RF assembly like a leaf or a door to the side. The entire apparatus, including the cradle, incubator, RF coil assembly, and sliding mechanism are configure by size shape and material to be inserted within an MRI bore. Further they can be fitted on an MRI safe cart, a transport device, an operating table, a treatment apparatus etc.

Figure 11A:
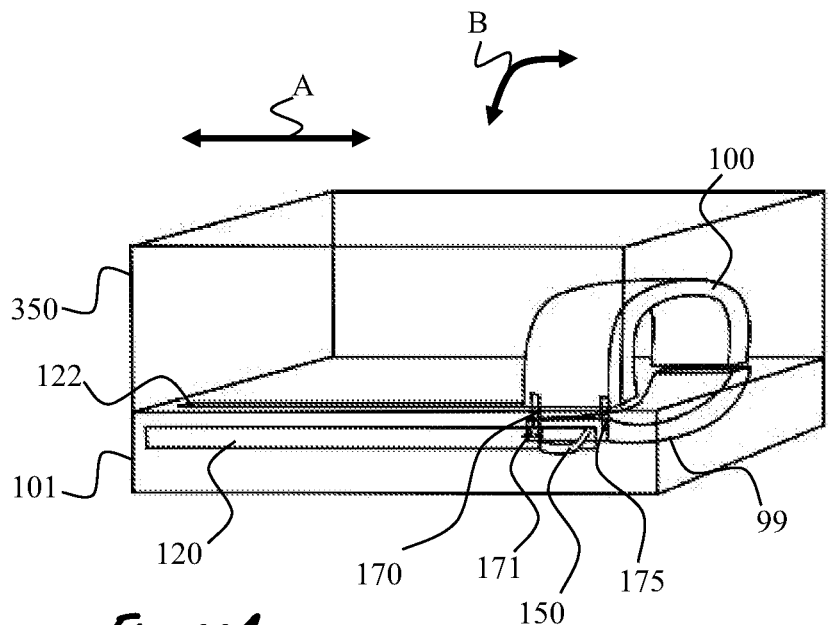
FIG. 11A is a schematic illustration of an installable RF coil assembly, in a perspective view placed within a neonate incubator.

Reference is now being made to FIG. 11A schematically illustrating in an out of scale manner, an embodiment of the invention. Illustrated is a perspective view of a neonate's cradle (101), connected to an envelope creating a closed environment incubator, with an installable RF coil assemblies (100) that is maneuverable to at least two positions: over a neonate accommodated in a cradle and below or aside the cradle when it is not required for imaging. The RF coil assembly is maneuverable along a sliding mechanism (122) along the longitudinal axis of the neonate. In this embodiment the RF coil assembly comprises at least two pieces, one is configured to be placed at least partially over a neonate (100), and at least a second RF coil (99) configured to be placed below at least a portion of the neonate. The RF coils can be connected functionally, or mechanically, and further can be configured to be moved together or separate. The lower RF coil (99) is placed within the cradle, under a thin mattress and is designated for bettering the magnetic resonance scanning of the back side of a neonate without having to change the neonate's position. The sliding mechanism (122, 120) is embedded within the cradle (101). The entire apparatus of the RF coil assemblies (100, 99) and the cradle are enveloped (350) to create an internal environment incubator fitted to life support and/or accommodate a neonate. A handle (150) is provided to manually maneuver the RF coil assemblies externally to the closed environment incubator. This handle (150) can move along an external track (120), part of the sliding mechanism, while maneuvering the RF coil assembly along the track (122) internally placed within the incubator. The maneuvering mechanism further comprises at least one latch (170) configured to secure at least one position of at least one of the RF coil assemblies (100, 99). The latch further comprises a button, a lever or a switch (171) configured to allow the handler to lock or release the latch (170). A second maneuver of the RF coil is possible by maneuvering the maneuverable connection (175) configured to allow a reversible movement of the RF coil assembly tilting or turning around a pivot point allowing the RF coil assembly to be placed either away from a residing neonate's head, or at least partially around the neonate's head and not at least partially above the neonate's head. Additionally or alternatively, the maneuverable connection (175) can be configured to act as a hinge opening the RF coil as a flap or door (not shown). The entire apparatus, including the cradle, incubator, RF coil assembly, and sliding mechanism are configure by size shape and material to be inserted within an MRI bore. Further they can be fitted on an MRI safe cart, a transport device, an operating table, a treatment apparatus etc. The entire apparatus, including the cradle, incubator, RF coil assembly, and sliding mechanisms or a portion thereof are made of MRI-safe material, transparent material, fire retardant material, sterilizable material, recyclable material, disposable material and any combination thereof. In this embodiment the neonate resides in a protected life supporting environment, while being imaged. Further there are fewer interventions like moving the neonate because the RF coil assembly is adjacent to the neonate from above the neonate, below the neonate, and around the top of the neonate's head in a reclining position.

Figure 11B:
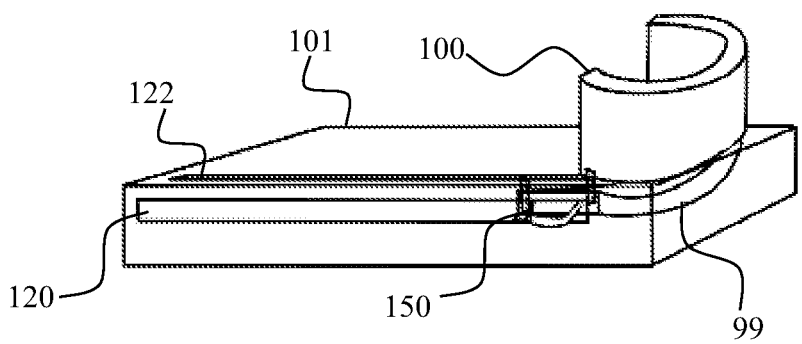
FIG. 11B is a schematic illustration of an installable RF coil assembly, in a perspective view.

Additionally or alternatively, the maneuverable mechanism for reciprocal linear movement or the tilting/turning/shifting is manual, automatic, semi-automatic or any combination thereof. Further, the RF Coil can be maneuvered by remote control. Reference is now being made to FIG. 11B schematically illustrating in an out of scale manner, an embodiment of the invention. This illustration embodies an invention having the same specifications, and same number references as in FIG. 11A, leaving out the envelope. This embodiment provides an open environment RF coil assembly having a top (100) and bottom (99) RF coil assemblies in connection to a cradle (101) sized and shaped to accommodate a neonate. The handle (150) provides means for maneuvering at least one RF coil.

FIG. 1-11 further enable a maneuverable RF coil assembly useful for being maneuvered at both positions (i) over a neonate immobilized within his/her cradle at time of MR imaging; and (ii) below or aside the cradle when it is not required for imaging, comprising at least one RF coil and maneuvering mechanism; wherein the maneuvering mechanism comprises both (i) a linear reciprocating mechanism for approaching or otherwise drawing away at least one coil to and from the neonate; and (ii) tilting mechanism for placing at least one coil away from the neonate.

FIGS. 1-11 further enable a multi-functional maneuvering mechanism for maneuvering an RF coil assembly to and from at least two positions (i) over a neonate immobilized within his/her cradle at time of MR imaging; and (ii) below or aside the cradle when it is not required for imaging, comprising at least one RF coil and maneuvering mechanism; wherein the multi-functional maneuvering mechanism comprises (i) at least one first linear reciprocating mechanism for approaching or otherwise drawing away at least one coil to and from the neonate; and (ii) at least one second tilting mechanism for placing at least one coil away from the neonate.

FIGS. 1-11 further enable an MRI-compatible neonate's cradle comprising a maneuverable RF coil; the maneuverable RF coil assembly is useful for being maneuvered at both positions (i) over a neonate immobilized within his/her cradle at time of MR imaging; and (ii) below or aside the cradle when it is not required for imaging, comprising at least one RF coil and maneuvering mechanism; wherein the maneuvering mechanism comprises both (i) a linear reciprocating mechanism for approaching or otherwise drawing away at least one coil to and from the neonate; and (ii) tilting mechanism for placing at least one coil away from the neonate.

FIGS. 1-11 further enable an MRI-compatible neonate's cradle comprising a maneuverable RF coil; comprising a multi-functional maneuvering mechanism for maneuvering an RF coil assembly to and from at least two positions (i) over a neonate immobilized within his/her cradle at time of MR imaging; and (ii) below or aside the cradle when it is not required for imaging, comprising at least one RF coil and maneuvering mechanism; wherein the multi-functional maneuvering mechanism comprises (i) at least one first linear reciprocating mechanism for approaching or otherwise drawing away at least one coil to and from the neonate; and (ii) at least one second tilting mechanism for placing at least one coil away from the neonate.

FIGS. 1-11 further enable an MRI-compatible cart in connection with an MRI-compatible neonate's cradle comprising a maneuverable RF coil; wherein the cart and the MRI-compatible neonate's cradle are adapted by means of size and shape to both (i) accommodate the cradle within an MRD open bore whilst (ii) the cart is at least partially accommodated either within the MRD infrastructure or surround the same. FIGS. 1-11 further enable an MRI-compatible cart in connection with an MRI-compatible neonate's cradle, the cradle comprises or otherwise in connection with a maneuverable RF coil assembly is useful for being maneuvered at both positions (i) over a neonate immobilized within his/her cradle at time of MR imaging; and (ii) below or aside the cradle when it is not required for imaging, comprising at least one RF coil and maneuvering mechanism; wherein the maneuvering mechanism comprises both (i) a linear reciprocating mechanism for approaching or otherwise drawing away at least one coil to and from the neonate; and (ii) tilting mechanism for placing at least one coil away from the neonate.

FIGS. 1-11 further enable an MRI-compatible cart in connection with an MRI-compatible neonate's cradle, the cradle comprises or otherwise in connection with a multi-functional maneuvering mechanism for maneuvering an RF coil assembly to and from at least two positions (i) over a neonate immobilized within his/her cradle at time of MR imaging; and (ii) below or aside the cradle when it is not required for imaging, comprising at least one RF coil and maneuvering mechanism; wherein the multi-functional maneuvering mechanism comprises (i) at least one first linear reciprocating mechanism for approaching or otherwise drawing away at least one coil to and from the neonate; and (ii) at least one second tilting mechanism for placing at least one coil away from the neonate.

FIGS. 1-11 further enable an MRI-system comprising an MRD, and a cart, insertably accommodated within or around the MRD's infrastructure, the card comprising or otherwise being in connection with an MRI-compatible neonate's cradle comprising a maneuverable RF coil.

FIGS. 1-11 further enable an MRI-system comprising an MRD, and a cart, insertably accommodated within or around the MRD's infrastructure, the card comprising or otherwise being in connection with an MRI-compatible neonate's cradle and a RF coil assembly maneuvering mechanism; wherein at least one is true: (a) the maneuvering mechanism comprises both (i) a linear reciprocating mechanism for approaching or otherwise drawing away at least one coil to and from the neonate; and (ii) tilting mechanism for placing at least one coil away from the neonate; and/or (b) the maneuvering mechanism is a multi-functional maneuvering mechanism comprises (i) at least one first linear reciprocating mechanism for approaching or otherwise drawing away at least one coil to and from the neonate; and (ii) at least one second tilting mechanism for placing at least one coil away from the neonate.

FIGS. 1-11 further enable a method of maneuvering an RF coil, comprising at least two different steps: a step of (i) linearly reciprocating an RF coil assembly for approaching or otherwise drawing away at least one coil to and from a neonate to be MR imaged; and then (ii) tilting the RF coil assembly for placing at least one coil away from the neonate when the neonate is not MR imaged.

FIGS. 1-11 further enable a method of providing an MRI-compatible neonate's cradle with a maneuverable RF coil, comprising at least two different steps of maneuvering an RF coil: a step of (i) linearly reciprocating an RF coil assembly for approaching or otherwise drawing away at least one coil to and from a neonate to be MR imaged; and then (ii) tilting the RF coil assembly for placing at least one coil away from the neonate when the neonate is not MR imaged.

FIGS. 1-11 further enable a method for both (i) applying an RF coil over a neonate immobilized within his/her cradle and (ii) conveniently removing the RF coil from the neonate and safely placing it when it is not required for imaging; comprising at least two different steps of maneuvering an RF coil: a step of (i) linearly reciprocating an RF coil assembly for approaching or otherwise drawing away at least one coil to and from a neonate to be MR imaged; and then (ii) tilting the RF coil assembly for placing at least one coil away from the neonate when the neonate is not MR imaged.

The invention claimed is:

1. A maneuverable radio frequency coil assembly (MRCA) adaptable for use with a neonate cradle, the MRCA comprising:
   a radio frequency (RF) coil disposed within a housing;
   a sliding mechanism, wherein the sliding mechanism is coupled to or formed within the housing, the sliding mechanism configured to allow the housing to slide linearly along an axis that is parallel to a longitudinal axis of the neonate cradle between a first linear position and a second linear position when the housing is coupled to the neonate cradle, wherein the first linear position is located substantially at the same location as the end of the neonate cradle associated with the head of a neonate, and the second linear position is located at a predetermined linear position away from the first linear position in a direction away from the neonate cradle; and
   a rotating mechanism, wherein the rotating mechanism is coupled to or formed within the housing, the rotating mechanism configured allow the housing to rotate about the axis between a first rotation position and a second rotation position when the housing is coupled to the neonate cradle, wherein the first rotation position is a position such that were the housing to also be in the first linear position the housing would be capable of receiving at least a portion of the head of a neonate position on the neonate cradle, and the second rotation position is a predetermined rotatable position about the axis.

2. The MCRA according to claim 1, wherein said housing is capable of being moved in a plurality of consecutively maneuverable movements.

3. The MCRA according to claim 1, wherein said housing is capable of being positioned in a plurality of positions.

4. The MCRA according to claim 1, wherein at least one of:
   a. said MCRA comprises a handle configured for maneuvering the housing by a MCRA handler;
   b. each of said sliding mechanisms and rotating mechanisms is comprises one of: an automated mechanism, a manual mechanism, a semi-automated mechanism, and a remote controlled mechanism;
   c. said MCRA comprises a least one latch configured to secure at least one position of the housing; and
   d. said MCRA comprises at least one sensor configured to sense one or more of: a structural integrity of said RF coil, a structural integrity of said maneuvering mechanisms, a position of said RF coil, a proximity of said neonate to said RF coil, a received RF signal, and a transmitted RF signal.

5. The MCRA according to claim 1, wherein at least one of:
   a. said RF coil comprises a plurality of RF coils;
   b. said RF coil is configured to connect to at least a second RF coil; and,
   c. said RF coil is connected to at least a second RF coil by a maneuverable connection.

6. The MCRA according to claim 1, wherein at least one of:
   a. said RF coil is one or more of a: solenoid coil, a planar coil, a volume coil, a surface coil, and a quadrature coil;
   b. said RF coil is a multi-tuned RF coil; and, c. said RF coil comprises a multi-channel RF coil reconfigurable between a plurality of operational modes.

7. The MCRA according to claim 1 wherein said housing is configured to close an opening of an incubator when in the first linear position and first rotation position.

8. The MCRA according to claim 1, wherein said RF coil is a solenoid coil.

9. The MCRA according to claim 1, wherein the housing is not rotatable unless the housing is in a linear position such that when a neonate is located on the neonate cradle, rotation does not interfere with the head of the neonate.

10. The MCRA according to claim 1 wherein:
the housing is a structure having a base and a wall, such that when the housing is in the first linear position and the first rotation position, the base is configured to receive at least the portion of the head of the neonate and the wall extends from the base along the axis;

the housing has a recess located along the wall, said recess extending from the base of the structure along at least a portion of the length of the wall, wherein the size of the recess is configured to permit life support equipment to extend to the head of a neonate position on the neonate cradle without the life support equipment being inside the RF coil.

11. The MCRA of claim 10, wherein the structure has a substantially cylindrical shape and wherein the wall is a curved wall.

12. The MCRA of claim 1, wherein the sliding mechanism is configured to mate with a sliding mechanism associated with the neonate cradle.

13. The MCRA of claim 1, wherein the rotating mechanism of the housing is configured to mate with a rotating mechanism associated with the neonate cradle.

* * * * *